US006603012B2

(12) United States Patent
Belloni et al.

(10) Patent No.: US 6,603,012 B2
(45) Date of Patent: Aug. 5, 2003

(54) RAR SELECTIVE RETINOID AGONISTS

(75) Inventors: Paula Nanette Belloni, Half Moon Bay, CA (US); Synese Jolidon, Blauen (CH); Michael Klaus, Weil am Rhein (DE); Jean-Marc Lapierre, Mountain View, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/840,486

(22) Filed: Apr. 23, 2001

(65) Prior Publication Data

US 2002/0026060 A1 Feb. 28, 2002

(30) Foreign Application Priority Data

May 2, 2000 (EP) .............................. 00109346

(51) Int. Cl.$^7$ ..................... C07D 213/06; C07D 271/06
(52) U.S. Cl. ................. 546/342; 548/131; 548/204; 548/376.1; 548/562; 549/499; 560/10; 560/58; 562/427; 562/466; 562/473
(58) Field of Search ................. 546/342; 548/131, 548/204, 376.1, 562; 549/499; 560/10, 58; 562/427, 486, 473

(56) References Cited

U.S. PATENT DOCUMENTS

| | | | |
|---|---|---|---|
| 5,006,550 A | | 4/1991 | Chandraratna |
| 5,238,683 A | | 8/1993 | Crystal |
| 5,292,499 A | | 3/1994 | Evans et al. |
| 5,364,615 A | | 11/1994 | Debs et al. |
| 5,387,594 A | | 2/1995 | Bernardon et al. |
| 5,607,915 A | | 3/1997 | Patton |
| 5,654,331 A | * | 8/1997 | Bernardon ............ 514/532 |

FOREIGN PATENT DOCUMENTS

| | | |
|---|---|---|
| DE | 40 33 567 A1 | 4/1992 |
| EP | 661 258 | 7/1995 |
| EP | 661 260 | 7/1995 |
| WO | WO 92/06948 | 4/1992 |
| WO | WO 96/30009 | 10/1996 |
| WO | WO 97/33856 | 9/1997 |

OTHER PUBLICATIONS

Charpentier, Bruno et al: Bioorg. Med. Chem. Lett. (1995). 5(23), 2801–4.
Douguet, Dominique et al: Quant. Struct.–Act. Relat. (1999), 18(2), 107–123.
Rossi, R. et al, Tetrahedron 55 (1999) pp. 11343–11364.
Teng, M. et al., J. Med. Chem. (1997) 40:2445–2451.
Massaro et al, A. J. Physiol. (1996) 270, pp. L305–L310.
Apfel, C. et al, Proc. Nat. Sci. Acad. (1992) 89:7129–7133.
Nishizawa, M., Tetrahedron Letters (1994) 35:4367–4370.
Seager, H., Pharmaceutical Tech. (1985) 9:84–104.
Massaro, D. et al, Nature Medicine (1997) 3:675–677.
Hintermann, T., et al, Helv. Chim. Acta, (1998) 81:2093–2126.
Waugh, K. et al, J. Med. Chem. (1985) 28:116–124.

* cited by examiner

*Primary Examiner*—Charanjit S. Aulakh
(74) *Attorney, Agent, or Firm*—George W. Johnston; Patricia S. Rocha-Tramaloni; Bernard Lau

(57) ABSTRACT

New compounds containing bicyclic fused rings, one of which being a phenyl moiety connected by an aliphatic chain to a cycloalkyl or aryl moiety, and pharmaceutically active salts thereof are useful as RAR selective retinoid agonists. Furthermore, such retinoic acid receptor agonists, particularly retinoic acid receptor γ (RARγ) selective agonists, are useful for the treatment of emphysema and associated pulmonary diseases, as well as for the therapy and prophylaxis of dermatological disorders, for the therapy and prophylaxis of malignant and premalignant epithelial lesions, tumors and precancerous changes of the mucous membrane in the mouth, tongue, larynx, esophagus, bladder, cervix and colon.

25 Claims, No Drawings

RAR SELECTIVE RETINOID AGONISTS

BACKGROUND OF THE INVENTION

This invention relates to new RAR selective retinoid agonists and to the use of such retinoic acid receptor agonists, particularly retinoic acid receptor γ (RARγ) selective agonists for the treatment of emphysema.

Chronic obstructive pulmonary disease (COPD) is a major cause of morbidity and mortality, ranking third and fourth as the leading cause of death in the European Union and North America respectively. COPD is characterized by reduced maximum expiratory flow, which does not change over several months and which persists for 2 or more consecutive years. Patients with the most severe form of COPD generally present with a significant degree of emphysema. Emphysema is defined anatomically by permanent airspace enlargement distal to the terminal bronchioles. It is characterized by gradual loss of lung recoil, alveolar destruction, decreased alveolar surface area and gas exchange, leading to a reduced FEV1. These two features, impaired gas exchange and reduction in expiratory flow, are characteristic physiological abnormalities from which patients with emphysema suffer. The main symptom of patients with severe emphysema is shortness of breath during minimal physical activity.

The most common cause of emphysema is cigarette smoking although other potential environmental toxins may also contribute. These various insulting agents activate destructive processes in the lung including release of active proteases and free radical oxidants in excess of protective mechanisms. The imbalance in protease/anti-protease levels leads to destruction of the elastin matrix, loss of elastic recoil, tissue damage and continuous decline in lung function. Removing the injurious agents (i.e. quit smoking) slows the rate of damage, however, the damaged alveolar structures do not repair and lung function is not regained.

Retinoic acid is a multifunctional modulator of cellular behavior, having the potential to alter both extracellular matrix metabolism and normal epithelial differentiation. In lung, retinoic acid has been shown to modulate various aspects of lung differentiation by interacting with specific retinoic acid receptors (RAR) that are selectively expressed temporally and spatially. Coordinated activation of RARβ and RARγ has been associated with lung branching and alveolization/septation. During alveolar septation, retinoic acid storage granules increase in the fibroblastic mesenchyme surrounding alveolar walls and RARγ expression in the lung peaks. Depletion of these retinyl-ester stores parallels the deposition of new elastin matrix and septation. In support of this concept, (Massaro et al., Am. J. Physiol., 1996, 270, L305–L310) demonstrated that postnatal administration of retinoic acid increases the number of alveoli in rats. Furthermore, the capacity of dexamethasone to prevent the expression of CRBP and RARβ mRNA and subsequent alveolar septation in developing rat lungs was abrogated by all-trans retinoic acid.

Recent studies demonstrated that all-trans retinoic acid can induce formation of new alveoli and return elastic recoil to near normal in animal models of emphysema (D. Massaro et al. Nature Medicine, 1997, 3, 675). However, the mechanism by which this occurs remains unclear.

Retinoids are a class of compounds structurally related to vitamin A, comprising natural and synthetic compounds. Several series of retinoids have been found clinically useful in the treatment of dermatological and oncological diseases.

Retinoic acid and its other naturally occurring retinoid analogs (9-cis retinoic acid, all-trans 3,4-didehydro retinoic acid, 4-oxo retinoic acid and retinol) are pleiotropic regulatory compounds that modulate the structure and function of a wide variety of inflammatory, immune and structural cells. They are important regulators of epithelial cell proliferation, differentiation and morphogenesis in lungs. Retinoids exert their biological effects through a series of hormone nuclear receptors that are ligand inducible transcription factors belonging to the steroid/thyroid receptor superfamily. The retinoid receptors are classified into two families, the retinoic acid receptors (RARs) and the retinoid X receptors (RXRs), each consisting of three distinct subtypes (α, β, and γ). Each subtype of the RAR gene family encodes a variable number of isoforms arising from differential splicing of two primary RNA transcripts. All-trans retinoic acid is the physiological hormone for the retinoic acid receptors and binds with approximately equal affinity to all the three RAR subtypes, but does not bind to the RXR receptors for which 9-cis retinoic acid is the natural ligand.

In many non-pulmonary tissues, retinoids have anti-inflammatory effects, alter the progression of epithelial cell differentiation, and inhibit stromal cell matrix production. These properties have led to the development of topical and systemic retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis. A limitation in the therapeutic use of retinoids outside of cancer has stemmed from the relative toxicity observed with the naturally occurring retinoids, all-trans retinoic acid and 9-cis retinoic acid. These natural ligands are non-selective and therefore have pleiotropic effects throughout the body, which are often toxic. Recently various retinoids have been described that interact selectively or specifically with the RAR or RXR receptors or with specific subtypes (α, β, γ) within a class.

Thus the retinoids according to the invention can further be used for the therapy and prophylaxis of dermatological disorders which are accompanied by epithelial lesions, e.g. acne and psoriasis, light- and age-damaged skin; as well as for the promotion of wound healing, for example of incised wounds, such as surgical wounds, wounds caused by burns and other wounds caused by cutaneous trauma; and for the therapy and prophylaxis of malignant and premalignant epithelial lesions, tumours and precancerous changes of the mucous membrane in the mouth, tongue, larynx, oesophagus, bladder, cervix and colon. In particular, the retinoids according to the invention promote repair of damaged alveoli.

SUMMARY OF THE INVENTION

This invention provides new RAR selective retinoid agonists of formula I

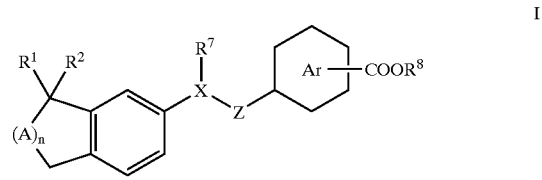

wherein
  $R^1$ and $R^2$ independently of each other are hydrogen or lower alkyl;

A is C(R$^5$R$^6$),
n is an integer 1, 2 or 3,
B is C(R$^3$R$^4$), oxygen, S(O)$_m$ or N-alkyl and
m is 0, 1 or 2; or
A is oxygen,
n is 1 and
B is C(R$^3$R$^4$);
X is —CR$^7$— or nitrogen;
R$^3$, R$^4$, R$^5$ and R$^6$ independently of each other are hydrogen or lower alkyl;
R$^7$ and R$^{7'}$ independently of each other are hydrogen, alkyl, alkenyl, alkoxy, alkoxyalkyl, substituted alkyl, phenyloxy or substituted phenyloxy, or R$^7$ and R$^{7'}$ together are —(CH$_2$)$_p$—, where p is 2–6, with the proviso that when X is nitrogen then R$^7$ is alkyl, alkoxyalkyl or substituted alkyl;
Z is —COO—, —OCO—, —CH$_2$—CH$_2$—, —CH=CH—, —C≡C—, —CH$_2$O—, —CH$_2$S—, —OCH$_2$—, —SCH$_2$—, —COCH$_2$— or —CH$_2$CO—, with the provisos that when Z is —OCH$_2$—, or —SCH$_2$—, then X is —CR$^{7'}$—, and that when Z is —C≡C— then X is CR$^7$ and R$^7$ is phenoxy or substituted phenoxy;
Ar is phenyl, substituted phenyl or a heteroarylic ring; and
R$^8$ is hydrogen, lower alkyl or benzyl;
and pharmaceutically acceptable salts of carboxylic acids of formula I.

DETAILED DESCRIPTION OF PREFERRED EMBODIMENTS

In one aspect, this invention provides new RAR selective retinoid agonists of formula I

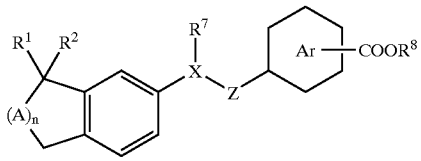

wherein
R$^1$, R$^2$ are independently of each other hydrogen or lower alkyl;
A represents C(R$^5$R$^6$) and
n is an integer 1, 2 or 3; or
A is oxygen and
n is 1;
B represents C(R$^3$R$^4$), oxygen, S(O)$_m$ or N-alkyl, with the proviso that when A is oxygen, then B is C(R$^3$R$^4$);
m is 0, 1 or 2;
X is —CR$^7$— or nitrogen;
R$^3$, R$^4$, R$^5$, R$^6$ are independently of each other hydrogen or lower alkyl;
R$^7$ and R$^{7'}$ are independently of each other hydrogen, alkyl, alkenyl, alkoxy, alkoxyalkyl, substituted alkyl, phenyloxy or substituted phenyloxy, or R$^7$ and R$^{7'}$ together are —(CH$_2$)$_p$—, where p is 2–6, with the proviso that when X is nitrogen then R$^7$ is alkyl, alkoxyalkyl or substituted alkyl;
Z is —COO—, —OCO—, —CH$_2$—CH$_2$—, —CH=CH—, —C≡C—, —CH$_2$O—, —CH$_2$S—, —OCH$_2$—, —SCH$_2$—, —COCH$_2$— or —CH$_2$CO—, with the provisos that when Z is —OCH$_2$—, or —SCH$_2$—, then X is —CR$^{7'}$—, and that when Z is —C≡C— then X is CR$^7$ and R$^7$ is phenoxy or substituted phenoxy;
Ar is phenyl, substituted phenyl or a heteroarylic ring; and
R$^8$ is hydrogen, lower alkyl or benzyl;
and pharmaceutically active salts of carboxylic acids of formula I.

Especially preferred compounds of formula I are the compounds wherein
B represents C(R$^3$R$^4$), oxygen, S(O)$_m$ or N—CH$_3$, with the proviso that when A is oxygen, then B is C(R$^3$R$^4$);
R$^7$ and R$^{7'}$ are, independently of each other, hydrogen, alkyl, alkoxy, alkoxyalkyl, substituted alkyl or phenyloxy or substituted phenyloxy, with the proviso that when X is nitrogen then R$^7$ is alkyl, alkoxyalkyl or substituted alkyl;
Z is —COO—, —OCO—, —CH=CH—, —CH≡CH—, —CH$_2$O—, —CH$_2$S—, —OCH$_2$—, —SCH$_2$—, —COCH$_2$— or —CH$_2$CO—, with the proviso that when Z is —OCH$_2$— or —SCH$_2$—, then X is —CH—.

The term "alkyl" as used herein denotes straight or branched chain alkyl residues containing 1 to 10, preferably 1 to 7 carbon atoms, such as methyl, ethyl, isobutyl, pentyl, amyl, 3-pentyl, hexyl or heptyl. The term "lower alkyl" as used herein denotes alkyl residues as defined above, however, with 1 to 5 carbon atoms.

As used herein, the term "alkoxy" refers to a straight or branched chain hydrocarbonoxy group wherein the "alkyl" portion is an alkyl group as defined above. Examples include methoxy, ethoxy, n-propyloxy and the like.

As used herein, the term "alkoxyalkyl" refers to an ether group wherein the "alkyl" portion is an alkyl group as defined above, examples of such groups are methoxymethyl, ethoxymethyl, propyloxymethyl, butyloxymethyl, methoxyethyl and the like.

As used herein the term "substituted alkyl" refers to an alkyl group as defined above substituted by one or more substituents such as hydroxy, halogen, mercapto, sulfanyl, trihalomethyl, phenyl, substituted phenyl, heterocyclyl, substituted heterocyclyl, or C$_3$–C$_7$-cycloalkyl.

As used herein the term "alkenyl" refers to an unsaturated alkyl group having at least one double bond.

As used herein "substituted phenyl" refers to a phenyl group substituted by one or more substituents such as alkyl, alkoxy, hydroxy, amino, halogen, trihalomethyl and the like.

The term "substituted phenyloxy" refers to a phenyloxy group wherein the substituents of the phenyl group are as defined above.

The term "halogen" refers to fluorine, chlorine, iodine or bromine.

The term "heterocyclyl" refers to a 5 or 6-membered ring containing at least one hetero atom selected from oxygen, sulfur and nitrogen, e.g. tetrahydrofuran, pyrrolidinyl, piperidinyl, morpholinyl and the like.

The term "heteroarylic ring" as used herein refers to a 5 or 6-membered heteroaryl ring containing at least one hetero atom selected from oxygen, sulfur, and nitrogen for example to pyridinyl, furanyl, thiophenyl, pyrazolyl, pyrrolyl, isoxazolyl, thiazolyl, oxadiazolyl and the like; the heteroarylic ring may be substituted by alkyl.

The compounds of formula I, wherein R$^8$ is hydrogen, form salts with pharmaceutically acceptable bases such as alkali salts, e.g. Na— and K-salts, and ammonium or substituted ammonium salts such as trimethylammonium or triethylammonium salts which are within the scope of this invention.

Preferred compounds of formula I are compounds, wherein X is $CR^{7'}$ ($R^{7'}$ being preferably hydrogen) or nitrogen and $R^7$ is $C_2$–$C_8$-alkyl, alkoxy, alkoxyalkyl, substituted alkyl, phenyloxy or substituted phenyloxy, i.e. compounds of formulae:

I-A
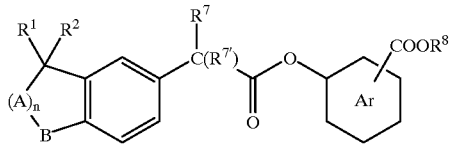

I-B
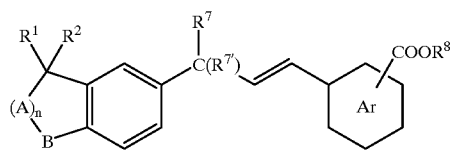

I-C
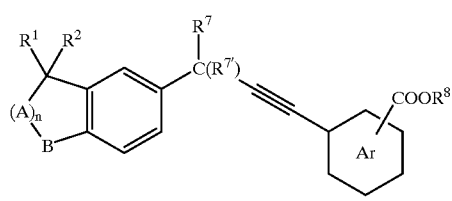

I-D
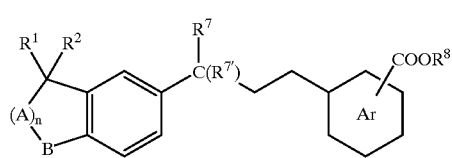

I-E
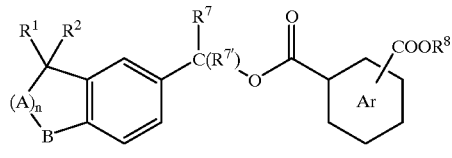

I-F
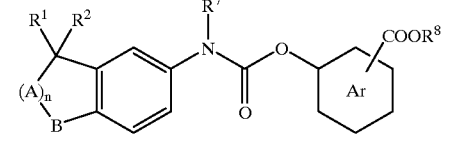

I-G
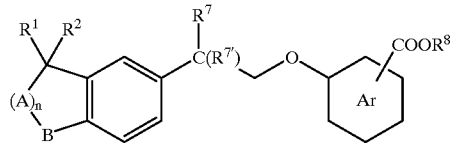

I-H
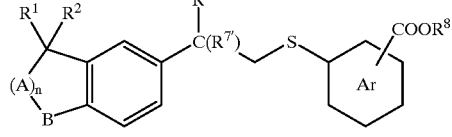

wherein the symbols are as defined above.

Compounds of formula I, wherein X is —CH— can be in the racemic form or in the (R) or (S) form.

Preferred are compounds of formula I and I–A–I–H, wherein A is —(CH$_2$)—, n is 2, B is a group $C(R^3R^4)$ and wherein Ar is phenyl with the —COOR$^8$ group in position 4.

An especially preferred embodiment of the invention are the compounds of formula I–A, wherein A is —(CH$_2$)—, n is 2, B is a group $C(R^3R^4)$, Ar is phenyl with the —COOR$^8$ group is in position 4 and $R^{7'}$ is $C_2$–$C_8$-alkyl, alkyloxy, alkoxyalkyl or substituted alkyl such as phenyl-methyl (=benzyl), 2-phenyl-ethyl, p-trifluoromethylphenyl-methyl, p-chlorophenyl-methyl and the like; or phenyloxy or substituted phenyloxy.

Such especially preferred compounds are e.g.

(RS)-4-[2-(5,5,8,8-tetramethyl-5,6,7,8-tetrahydronaphthalen-2-yl)-heptanoyloxy]-benzoic acid;

(RS)-4-[3-phenyl-2-(5,5,8,8-tetramethyl-5,6,7,8-tetrahydronaphthalen-2-yl)-propanoyloxy]-benzoic acid;

(RS)-4-[4-phenyl-2-(5,5,8,8-tetramethyl-5,6,7,8-tetrahydronaphthale-2-yl)-butanoyloxy]-benzoic acid;

(RS)-4-[2-(5,5,8,8-tetramethyl-5,6,7,8-tetrahydronaphthalen-2-yl)-3-(4-trifluoromethylphenyl)-propanoyloxy]-benzoic acid;

(RS)-4-[4-ethoxy-2-(5,5,8,8-tetramethyl-5,6,7,8-tetrahydronaphthalen-2-yl)-butanoyloxy]-benzoic acid;

(RS)-4-[3-(4-chlorophenyl)-2-(5,5,8,8-tetramethyl-5,6,7,8-tetrahydro-naphthalen-2-yl)-propanoyloxy]-benzoic acid;

(RS)-4-[butoxy-(5,5,8,8-tetramethyl-5,6,7,8-tetrahydro-naphthalen-2-yl)-acetoxy]-benzoic acid;

(RS)-4-[methoxy-(5,5,8,8-tetramethyl-5,6,7,8-tetrahydro-naphthalen-2-yl)-acetoxy]-benzoic acid;

(RS)-4-[ethoxy-(5,5,8,8-tetramethyl-5,6,7,8-tetrahydro-naphthalen-2-yl)-acetoxy]-benzoic acid;

(RS)-4-[propoxy-(5,5,8,8-tetramethyl-5,6,7,8-tetrahydro-naphthalen-2-yl)-acetoxy]-benzoic acid;

(R)- and (S)-4-[butoxy-(5,5,8,8-tetramethyl-5,6,7,8-tetrahydro-naphthalen-2-yl)-acetoxy]-benzoic acid;

R,S)-4-[(5,5,8,8-tetramethyl-5,6,7,8-tetrahydro-naphthalen-2-yl)-p-tolyloxy-acetoxy]-benzoic acid;

(RS)-4-[3-(4-fluorophenyl)-2-(5,5,8,8-tetramethyl-5,6,7,8-tetrahydronaphthalen-2-yl)-propanoyloxy]-benzoic acid; and RS)-4-[3-(3-fluorophenyl)-2-(5,5,8,8-tetramethyl-5,6,7,8-tetrahydronaphthalen-2-yl)-propanoyloxy]-benzoic acid.

Further preferred are compounds of formula I–A wherein A is —(CH$_2$)— and B is oxygen, e.g., (R,S)-4-[2-(4,4-dimethyl-chroman-6-yl)-heptanoyloxy]-benzoic acid.

A further preferred embodiment are compounds of formula I–B, wherein A is —(CH$_2$)—, n is 2, B is a group $C(R^3R^4)$, Ar is phenyl with the —COOR$^8$ group in position 4 and $R^7$ is alkyl, alkyloxy, alkoxyalkyl or substituted alkyl such as phenyl-methyl (benzyl), 2-phenyl-ethyl, p-trifluoromethylphenyl-methyl, p-chlorophenyl-methyl and the like; or phenyloxy or substituted phenyloxy. Such especially preferred compounds are (RS)-(E)-4-[3-(5,5,8,8-tetramethyl-5,6,7,8-tetrahydronaphthalen-2-yl)-oct-1-enyl]-benzoic acid;

(RS)-(E)-4-[3-(5,5,8,8-tetramethyl-5,6,7,8-tetrahydronaphthalen-2-yl)-but-1-enyl]-benzoic acid;

(RS)-(E)-4-[3-(5,5,8,8-tetramethyl-5,6,7,8-tetrahydronaphthalen-2-yl)-hex-1-enyl]-benzoic acid;

(RS)-(E)-4-[3-(5,5,8,8-tetramethyl-5,6,7,8-tetrahydronaphthalen-2-yl)-hepta-1,5-dienyl]-benzoic acid;

(RS)-(E)-4-[3-(5,5,8,8-tetramethyl-5,6,7,8-tetrahydronaphthalen-2-yl)-hept-1-enyl]-benzoic acid;

(RS)-(E)-4-[3-(5,5,8,8-tetramethyl-5,6,7,8-tetrahydronaphthalen-2-yl)-undec-1-enyl]-benzoic acid;

(RS)-(E)-4-[5-methyl-3-(5,5,8,8-tetramethyl-5,6,7,8-tetrahydronaphthalen-2-yl)-hex-1-enyl]-benzoic acid;

(RS)-(E)-4-[4-phenyl-3-(5,5,8,8-tetramethyl-5,6,7,8-tetrahydronaphthalen-2-yl)-but-1-enyl]-benzoic acid;

(RS)-(E)-4-[4-(4-chlorophenyl)-3-(5,5,8,8-tetramethyl-5,6,7,8-tetrahydronaphthalen-2-yl)-but-1-enyl]-benzoic acid;

(RS)-(E)-4-[3-(5,5,8,8-tetramethyl-5,6,7,8-tetrahydronaphthalen-2-yl)-4-(4-trifluoromethylphenyl)-but-1-enyl]-benzoic acid;

(RS)-(E)-4-[5-phenyl-3-(5,5,8,8-tetramethyl-5,6,7,8-tetrahydronaphthalen-2-yl)-pent-1-enyl]-benzoic acid;

(RS)-(E)-5-[3-(5,5,8,8-tetramethyl-5,6,7,8-tetrahydronaphthalen-2-yl)-oct-1-enyl]-thiophene-2-carboxylic acid;

(RS)-4-[3-butoxy-3-(5,5,8,8-tetramethyl-5,6,7,8-tetrahydro-naphthalen-2-yl)-propenyl]-benzoic acid;

(RS)-4-[3-benzyloxy-3-(5,5,8,8-tetramethyl-5-6-7-8-tetrahydro-naphthalen-2-yl)-propenyl]-benzoic acid;

(RS)-(E)-4-[4-(4-fluorophenyl)-3-(5,5,8,8-tetramethyl-5,6,7,8-tetrahydro-naphthalen-2-yl)-but-1-enyl]-benzoic acid;

(RS)-(E)-4-[4-(3-chlororophenyl)-3-(5,5,8,8-tetramethyl-5,6,7,8-tetrahydro-naphthalen-2-yl)-but-1-enyl]-benzoic acid;

(RS)-(E)-4-[4-(4-methoxyphenyl)-3-(5,5,8,8-tetramethyl-5,6,7,8-tetrahydro-naphthalen-2-yl)-but-1-enyl]-benzoic acid;

(RS)-(E)-3-fluoro-4-[3-(5,5,8,8-tetramethyl-5,6,7,8-tetrahydronaphthalen-2-yl)-oct-1-enyl]-benzoic acid;

(E)-4-[3-methyl-3-(5,5,8,8-tetramethyl-5,6,7,8-tetrahydronaphthalen-2-yl)-but-1-enyl]-benzoic acid;

(E)-4-[3-ethyl-3-(5,5,8,8-tetramethyl-5,6,7,8-tetrahydronaphthalen-2-yl)-pent-1-enyl]-benzoic acid;

(E)-4-[3-propyl-3-(5,5,8,8-tetramethyl-5,6,7,8-tetrahydronaphthalen-2-yl)-hex-1-enyl]-benzoic acid;

(R,S)-4-[3-(4-chloro-phenoxy)-3-(5,5,8,8-tetramethyl-5,6,7,8-tetrahydro-naphthalen-2-yl)-propenyl]-benzoic acid;

(R,S)-4-[3-(5,5,8,8-tetramethyl-5,6,7,8-tetrahydro-naphthalen-2-yl)-3-(4-trifluoromethyl-phenoxy)-propenyl]-benzoic acid;

(R,S)-4-[3-(5,5,8,8-tetramethyl-5,6,7,8-tetrahydro-naphthalen-2-yl)-3-p-tolyloxy-propenyl-benzoic acid; and (R,S)-4-[3-(5,5,8,8-tetramethyl-5,6,7,8-tetrahydro-naphthalen-2-yl)-3-(4-methoxy-phenoxy)-propenyl]-benzoic acid.

Further preferred are compounds of fomula I–B wherein A is —(CH$_2$)—, n is 2 and B is sulfur, —S(O)$_2$— or oxygen, e.g.,

[(RS)-(E)-4-[3-(4,4-dimethyl-thiochroman-6-yl)-oct-1-enyl]-benzoic acid];

(RS)-(E)-4-[3-(4,4-dimethyl-thiochroman-6-yl)-4-phenylbut-1-enyl]-benzoic acid;

(RS)-(E)-4-[3-(4,4-dimethyl-1,1-dioxide-thiochroman-6-yl)-oct-1-enyl]-benzoic acid;

(RS)-(E)-4-[3-(4,4-dimethyl-thiochroman-6-yl)-5-phenylpent-1-enyl]-benzoic acid; and (R,S)-4-[3-(4,4-dimethyl-chroman-6-yl)-oct-1-ethyl]-benzoic acid.

A further preferred embodiment are compounds of formula I–D, wherein A is —(CH$_2$)—, n is 2 and B is —(CR$^3$R$^4$)—, for example, (RS)-4-[3-(5,5,8,8-tetramethyl-5,6,7,8-tetrahydronaphthalen-2-yl)-oct-1-yl]-benzoic acid.

Further preferred are compounds of fomula I–G, wherein A is —(CR$^5$R$^6$)—, n is 2 and B is —(CR$^3$R$^4$)— for example, 4-[2-(5,5,8,8-tetramethyl-5,6,7,8-tetrahydronaphthalen-2-yl)-ethyloxy]-benzoic acid;

(R)-4-[2-(5,5,8,8-tetramethyl-5,6,7,8-tetrahydronaphthalen-2-yl)-heptyloxy]-benzoic acid;

(S)-4-[2-(5,5,8,8-tetramethyl-5,6,7,8-tetrahydronaphthalen-2-yl)-heptyloxy]-benzoic acid;

4-[2-methyl-2-(5,5,8,8-tetramethyl-5,6,7,8-tetrahydronaphthalen-2-yl)-propyloxy]-benzoic acid;

4-[2-propyl-2-(5,5,8,8-tetramethyl-5,6,7,8-tetrahydronaphthalen-2-yl)-pentyloxy]-benzoic acid;

4-[1-(5,5,8,8-tetramethyl-5,6,7,8-tetrahydronaphthalen-2-yl)-cyclopentyl-methoxy]-benzoic acid;

4-[1-(5,5,8,8-tetramethyl-5,6,7,8-tetrahydronaphthalen-2-yl)-cyclohexyl-methoxy]-benzoic acid;

(RS)-4-[3-(pyridin-2-yl)-2-(5,5,8,8-tetramethyl-5,6,7,8-tetrahydronaphthalen-2-yl)-propyloxy]-benzoic acid;

(RS)-4-[3-(pyridin-3-yl)-2-(5,5,8,8-tetramethyl-5,6,7,8-tetrahydronaphthalen-2-yl)-propyloxy]-benzoic acid;

(RS)-4-[3-(pyridin-4-yl)-2-(5,5,8,8-tetramethyl-5,6,7,8-tetrahydronaphthalen-2-yl)-propyloxy]-benzoic acid;

(RS)-4-[4-(pyridin-2-yl)-2-(5,5,8,8-tetramethyl-5,6,7,8-tetrahydronaphthalen-2-yl)-butyloxy]-benzoic acid;

RS)-4-[4-(pyridin-3-yl)-2-(5,5,8,8-tetramethyl-5,6,7,8-tetrahydronaphthalen-2-yl)-butyloxy]-benzoic acid;

(RS)-4-[4-(pyridin-4-yl)-2-(5,5,8,8-tetramethyl-5,6,7,8-tetrahydronaphthalen-2-yl)-butyloxy]-benzoic acid;

(RS)-4-[3-(1-pyrazol-1-yl)-2-(5,5,8,8-tetramethyl-5,6,7,8-tetrahydronaphthalen-2-yl)-propyloxy]-benzoic acid;

(RS)-4-[4-(pyrazol-1-yl)-2-(5,5,8,8-tetramethyl-5,6,7,8-tetrahydronaphthalen-2-yl)-butyloxy]-benzoic acid;

(RS)-4-[4-(pyrrol-1-yl)-2-(5,5,8,8-tetramethyl-5,6,7,8-tetrahydronaphthalen-2-yl)-butyloxy]-benzoic acid;

(RS)-4-[3-(5-methyl-isoxazol-2-yl)-2-(5,5,8,8-tetramethyl-5,6,7,8-tetrahydronaphthalen-2-yl)-propyloxy]-benzoic acid;

(RS)-4-[3-(2-methyl-thiazol-4-yl)-2-(5,5,8,8-tetramethyl-5,6,7,8-tetrahydronaphthalen-2-yl)-propyloxy]-benzoic acid;

(RS)-4-[3-(1,2,4-oxadiazol-3-yl)-2-(5,5,8,8-tetramethyl-5,6,7,8-tetrahydronaphthalen-2-yl)-propyloxy]-benzoic acid;

(RS)-4-[3-(furan-2-yl)-2-(5,5,8,8-tetramethyl-5,6,7,8-tetrahydronaphthalen-2-yl)-propyloxy]-benzoic acid;

(RS)-4-[3-(tetrahydrofuran-2-yl)-2-(5,5,8,8-tetramethyl-5,6,7,8-tetrahydronaphthalen-2-yl)-propyloxy]-benzoic acid;

(RS)-4-[3-(cyclohexyl)-2-(5,5,8,8-tetramethyl-5,6,7,8-tetrahydronaphthalen-2-yl)-propyloxy]-benzoic acid;

(RS)-4-[6-hydroxy-2-(5,5,8,8-tetramethyl-5,6,7,8-tetrahydronaphthalen-2-yl)-hexyloxy]-benzoic acid; and (RS)-4-[4-thioethyl-2-(5,5,8,8-tetramethyl-5,6,7,8-tetrahydronaphthalen-2-yl)-butyloxy]-benzoic acid;

and compounds of formula I–G, wherein A is —($CR^5R^6$)—, n is 2 and B is oxygen, N-alkyl or $S(O)_m$, m being 0 or 1, such compounds as for example, (RS)-4-[2-(N-ethyl-4,4-dimethyl-1,2,3,4-tetrahydroquinolin-6-yl)-heptyloxy]-benzoic acid;

(RS)-4-[2-(4,4-dimethyl-thiochroman-6-yl)-heptyloxy]-benzoic acid;

(RS)-4-[2-(4,4-dimethyl-1-oxide-thiochroman-6-yl)-heptyloxy]-benzoic acid; and (RS)-4-[2-(2,2,4,4-tetramethyl-chroman-6-yl)-heptyloxy]-benzoic acid.

A further preferred embodiment are compounds of formula I–C, wherein A is —($CH_2$)—, n is 2, B is a group $C(R^3R^4)$, Ar is phenyl with the —$COOR^8$ group is in position 4 and $R^7$ is phenyloxy or substituted phenyloxy.

A further preferred embodiment are compounds of formula I–F, wherein A is —($CH_2$)—, n is 2, B is a group $C(R^3R^4)$, Ar is phenyl with the $COOR^8$ group is in position 4 and $R^7$ is alkyl, alkoxyalkyl or substituted alkyl such as phenyl-methyl (benzyl), 2-phenyl-ethyl, p-trifluoromethylphenyl-methyl, p-chlorophenyl-methyl and the like.

A further preferred embodiment are compounds of formula I–H, wherein A is —($CH_2$)—, n is 2, B is a group $C(R^3R^4)$, Ar is phenyl with the —$COOR^8$ group is in position 4 and $R^7$ is alkyl, alkyloxy, alkoxyalkyl or substituted alkyl such as phenyl-methyl (benzyl), 2-phenyl-ethyl, p-trifluoromethylphenyl-methyl, p-chlorophenyl-methyl and the like or substituted alkoxy such as phenylmethoxy; or 2-phenylethoxy, or phenyloxy or substituted phenyloxy.

The compounds of formula I–A, wherein X is —CH—, Z is —COO— and $R^7$ is alkyl, alkoxyalkyl or substituted alkyl can be prepared according to the method depicted in reaction scheme 1:

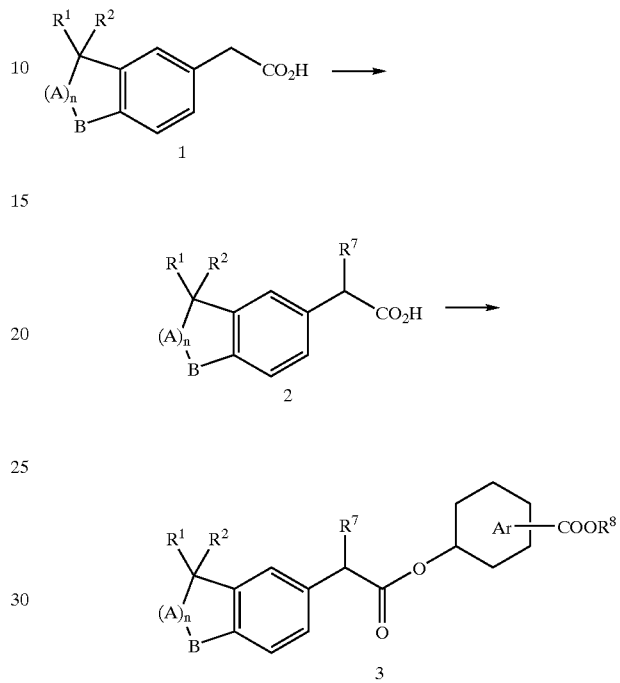

wherein the symbols are as defined above.

The compounds of formula 3 are readily accessible through the general synthetic route depicted in Scheme 1. The acid 1 can be prepared according to previous published procedures (WO 92/06948). The acid 1 can be doubly deprotonated with lithiumdiisopropylamide (LDA) and the resulting dianion can be reacted with a variety of electrophiles to give alkylated products of the type 2. A coupling using N,N'-dicyclohexylcarbodiimide (DCC) and 4-dimethylamino-pyridine (DMAP) with the appropriate functionalized 4-hydroxy-benzoate leads to compounds 3. Hydrolysis of the ester ($R^8$=alkyl) or hydrogenolysis ($R^8$=benzyl) provides the acid ($R^8$=H).

The compounds of formula I–A, wherein X is —CH—, Z is —COO— and $R^7$ is alkoxy can be prepared according to the method depicted in reaction scheme 1a:

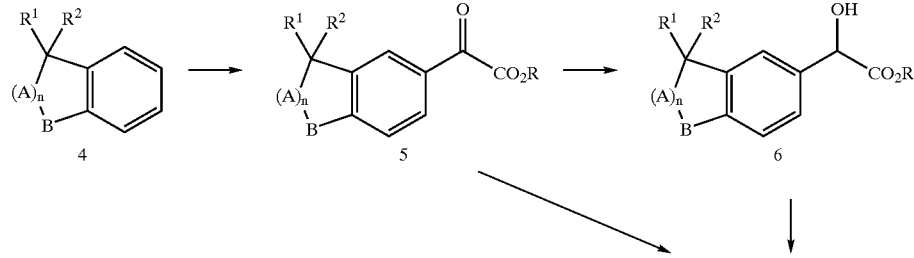

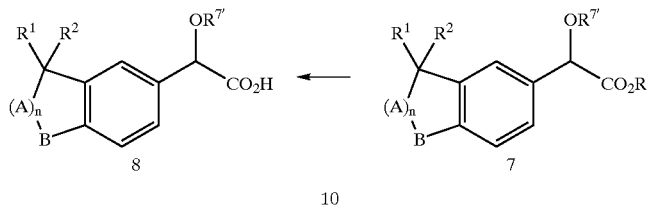

wherein A, B, n, $R^1$ and $R^2$ are as defined above and

R and $R^{7'}$ are, independently from each other, alkyl or substituted alkyl.

Starting compounds of formula 4 are known can be prepared by methods known in the art. The α-keto-ester 5 can be synthesized by Friedel-Crafts reaction of compound 4 with ethyl oxalyl chloride/$AlCl_3$. Other methods are described in Tetrahedron 55, 11343 (1999) by R. Rossi et al. Reduction of the ketogroup in 5 with sodium borohydride yields the 2-hydroxy-ester 6, which can be alkylated with various alkylhalogenides using silver oxide or cesium carbonate as a base to give compound 7. Another route to compound 7 is reductive alkylation of 5 according to M. Nishizawa, Tetrahedron Letters 35, 4367 (1994), using alkoxy-trimethylsilane and triethylsilane as reagents and trimethylsilyl triflate as catalyst. Hydrolysis of the ester 7 affords the acid 8, which can be transformed into compounds of formula I–A as shown in scheme 1.

Compounds of formula I–A, wherein X=—CH—, Z=—COO— and $R^7$=phenyloxy or substituted phenyloxy can be prepared according to scheme 1b:

Scheme 1b

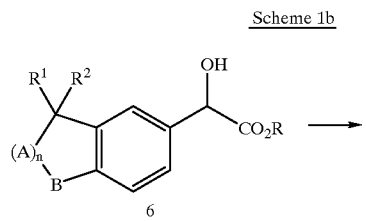

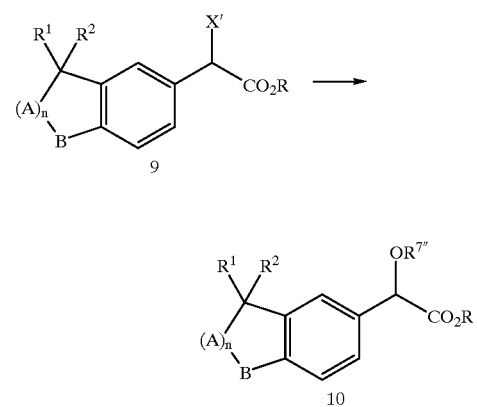

wherein A, B, n, R, $R^1$ and $R^2$ are as defined above;

X' is halogen; and $R^{7''}$ is unsubstituted phenyloxy or substituted phenyloxy.

The α-hydroxy-ester 6 can be transformed into the α-chloro- or α-bromo-ester 9 using $SOCl_2$ or $SOBr_2$. Reaction with a sodium phenolate affords the phenyloxy-ester 10, which can be transformed into compounds of formula I–A as shown in scheme 1.

The compounds of formula I–B, wherein X is —CH— and Z is —CH=CH— can be prepared according to the method depicted in reaction scheme 2:

Scheme 2

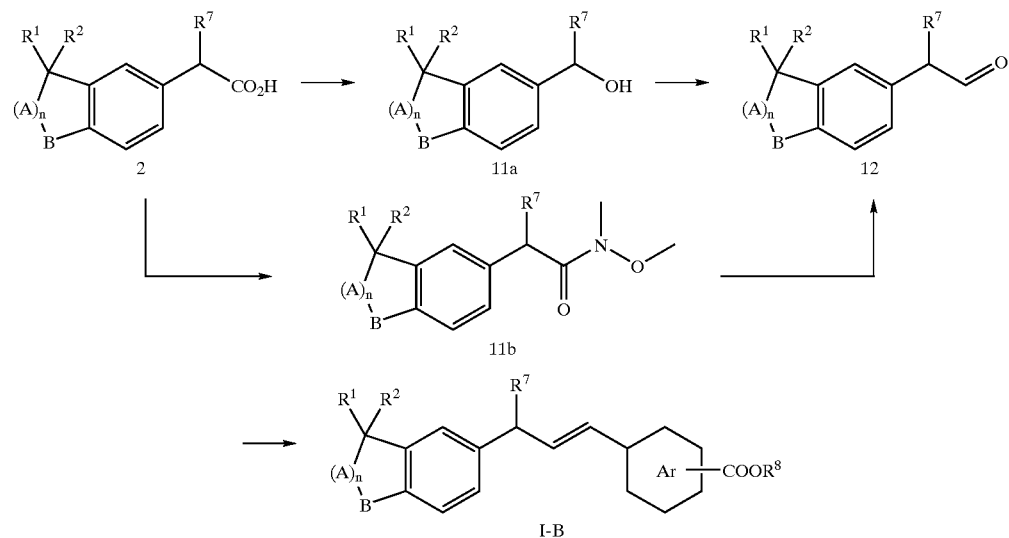

wherein A, B, n, $R^1$, $R^2$, $R^7$, Ar and $R^8$ are as defined above.

The acid 2 is being reduced to the alcohol 11a then reoxydated to the aldehyde 12 in high yields ($BH_3$·THF (tetrahydrofuran) followed by Swern oxydation). An alternative route with high yields consists of transforming the acid 2 to the Weinreb amide 11b and then reducing it with $LiAlH_4$ to the aldehyde 12. A Wittig-Horner with the appropriate phosphonate leads to the olefin I–B. Hydrolysis of the ester then gives the corresponding acid ($R^8$=H).

Compounds of the formula I–D can be obtained from intermediate I–B ($R^8$=alkyl or H) by hydrogenation of the olefin. Hydrolysis (where $R^8$=alkyl) under standard procedures provides the corresponding acids ($R^8$=H), see Scheme 3:

Scheme 3

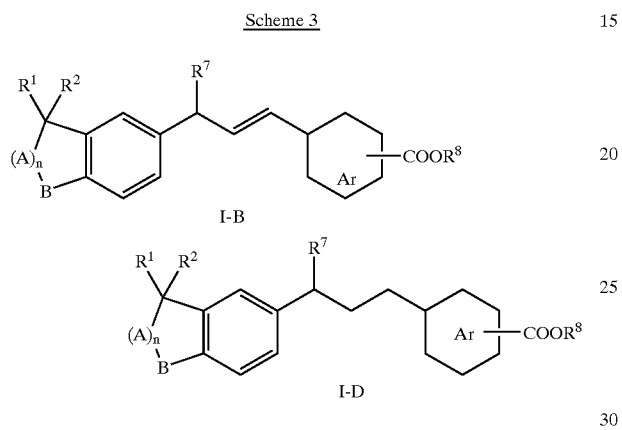

wherein the symbols are as defined above.

Compounds of formula I–G and I–H can be prepared according to the method depicted in reaction scheme 4.

Scheme 4

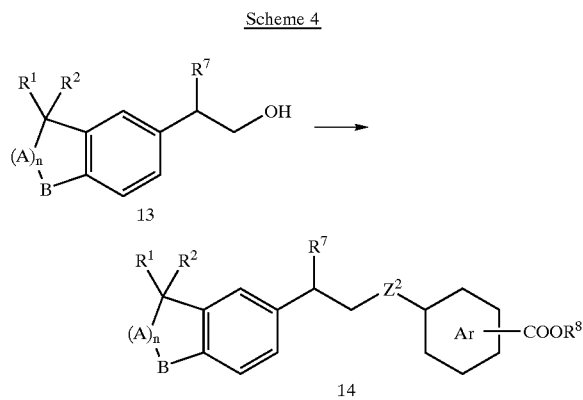

wherein
$Z^2$ is oxygen or sulfur, and the remaining symbols are as defined above.

Compound 13 can be produced analogously to compound 11a, wherein $R^7$ is defined as in formula I. The compounds 14 (where $Z^2$ is O or S) can be synthesized by a Mitsunobu type coupling (diethyl azodicarboxylate (DEAD), $Ph_3P$) using the appropriate phenol or thiophenol coupling partner and compound 13. Hydrolysis of the esters 14 can be accomplished using standard procedures to give the corresponding acids ($R^8$=H).

Reaction scheme 5 outlines the method for the preparation of compounds of formula I–C:

Scheme 5

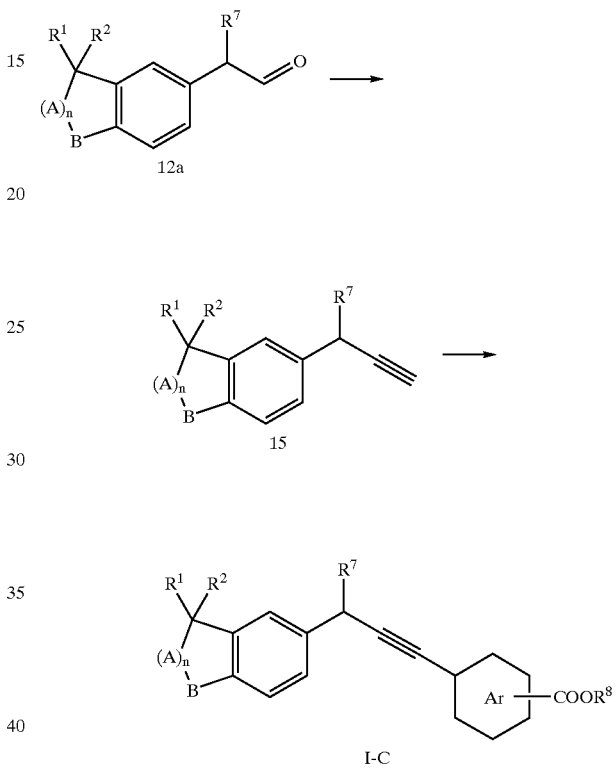

wherein the symbols are as defined above.

The aldehyde 12a is synthesized in the same manner as aldehyde 12, except that $R^7$ is phenoxy or substituted phenoxy. Aldehyde 12a can be transformed into the acetylenic derivatives 15, using the method of Corey and Fuchs by reaction with $Ph_3P/CBr_4$ then subsequently with butyllithium (BuLi). The intermediate 15 can then be coupled with an appropriate halo aromatic ester in a Pd(0) catalyzed reaction. The resulting compounds I–C can be hydrolyzed to the acids I–C ($R^8$=H) in the usual way.

Preparation of compounds of formula I–E:

Scheme 6

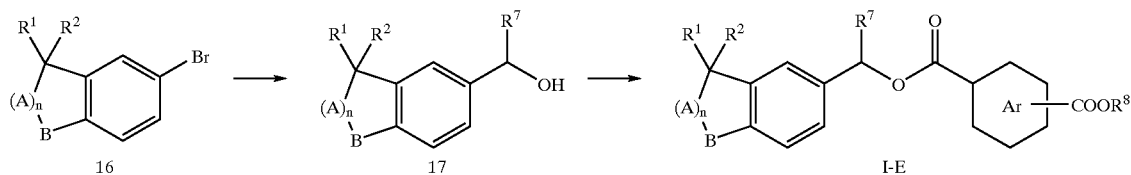

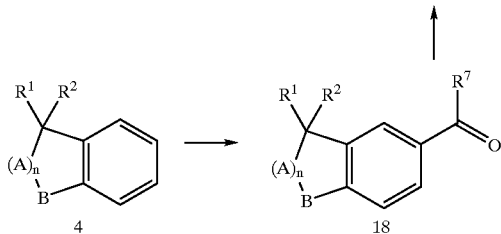

wherein the symbols are as defined above.

Compounds of the formula I–E can be synthesized according to Scheme 6, via two routes leading to intermediate 17. Bromide 16 is formed by the bromination of compound 4. The bromide 16 can be transformed into the Grignard reagent with Mg and then reacted with an aldehyde of formula $R^7CHO$. In a second way, compound 4 can be reacted with an acid chloride ($R^7COCl$)/AlCl$_3$ to give the ketone 18. Reduction of the carbonyl by BH$_3$.THF or LiAlH$_4$ yields the alcohol 17. Coupling of the alcohol 17 with a half ester of terephthalic acid provides the compounds of formula I–E ($R^8$=alkyl or benzyl). Hydrogenolysis ($R^8$=benzyl) provides the corresponding acid ($R^8$=H).

The compounds of formula I, wherein X is —CH— and Z is —CH$_2$CO— (formula 21 in scheme 7) can be prepared from the starting bromide 16, by formylation using lithium-halogen exchange/DMF. The aldehyde 19 can then be used in an aldol condensation with the substituted acetophenone. The enone 20 can be reacted with the appropriate cuprate or mixed cuprate to yield 21. Hydrolysis ($R^8$=alkyl) or hydrogenolysis ($R^8$=benzyl) provides the acid 21 ($R^8$=H).

Scheme 7

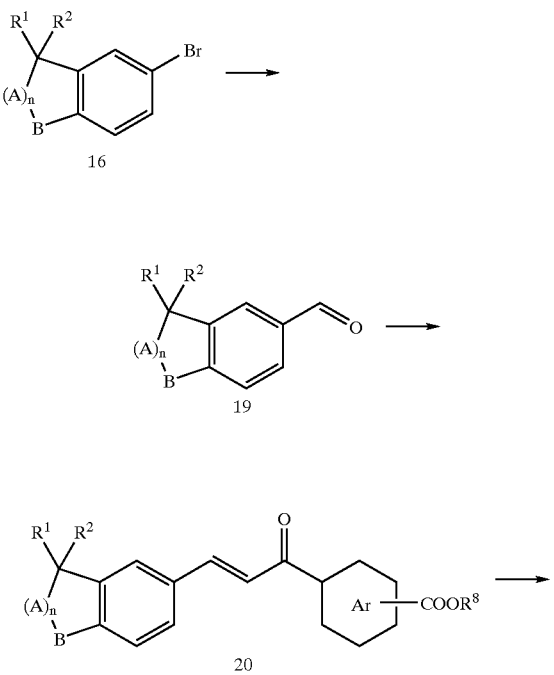

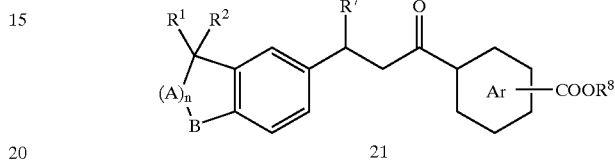

wherein the symbols are as defined above.

Compounds of formula I, wherein X is —CH— and Z is —COCH$_2$— can be prepared as described in reaction scheme 8. The aldehyde 12 can be converted to the dithiane 22 under standard procedures. The anion of 22 (from 22 and BuLi) is then trapped with the benzyl bromide bearing a protected or masked carboxyl group. Deprotection of the dithiane with Hg (ClO$_4$)$_2$ provides the carbonyl compound 23. Hydrolysis under standard conditions gives the keto acid 23, ($R^8$=H). See scheme 8:

Scheme 8

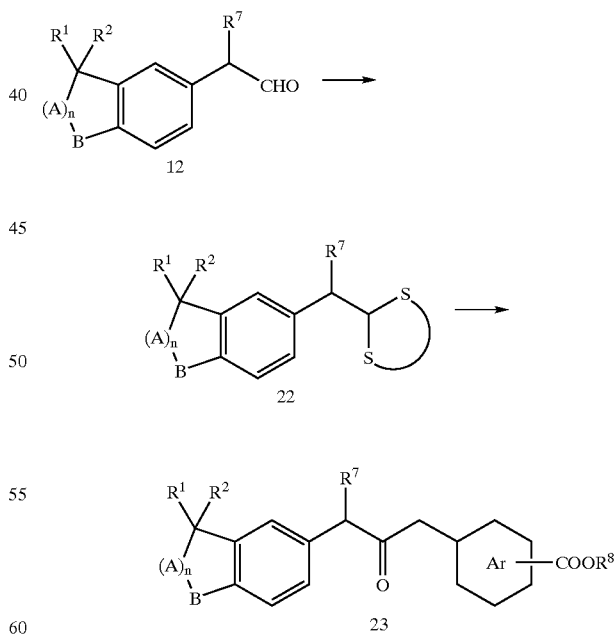

wherein the symbols are as defined above.

Compounds of formula I, wherein X is nitrogen and Z is —COO—, i.e. compounds of formula I–F can be prepared according to scheme 9:

Scheme 9

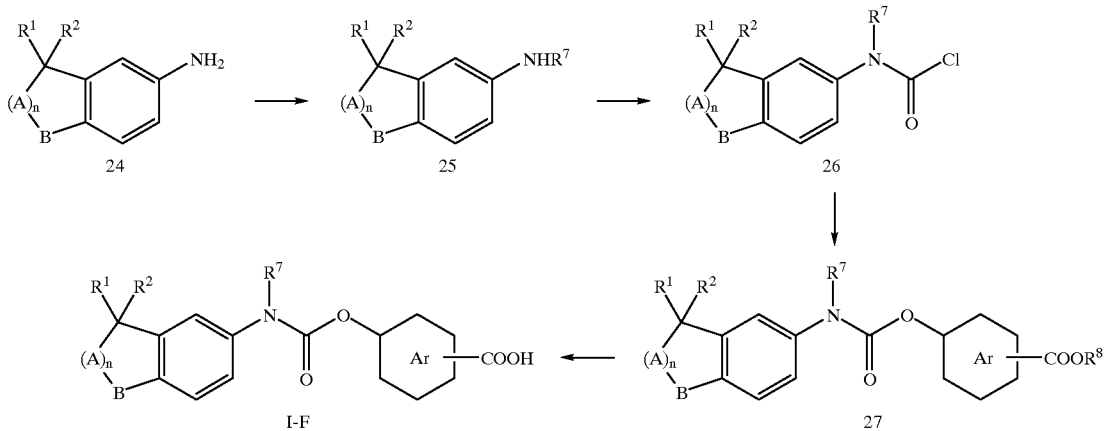

wherein the symbols are as defined above.

Compound 24 can be formed from compound 4 by methods known in the art. Monoalkylation of amine 24 (e.g. via the trifluoroacetylamide, alkylation using KOH/DMSO and hydrolysis) affords compound 25, which is chloroformylated with phosgene or triphosgene to give compound 26. Reaction with 4-hydroxy-benzoate ($R^8$=benzyl) and pyridine yields compound 27, which can be hydrogenated to give compound of formula I-F.

Further preferred compounds of formula I are those of formula I-J

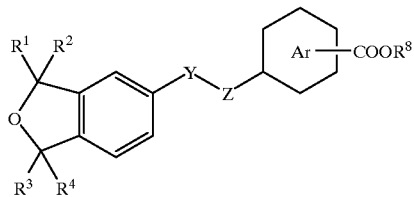

I-J wherein $R^1$, $R^2$, $R^3$ and $R^4$ independently of each other are hydrogen or lower alkyl;

Z is —OCH$_2$— or —SCH$_2$—,

Y is —CR$^{7'}$R$^{7'}$—, and
each R$^{7'}$ is independently hydrogen, alkyl, alkenyl, alkoxy, alkoxyalkyl, substituted alkyl, phenyloxy or substituted phenyloxy, or both R$^{7'}$ together are —(CH$_2$)$_p$—, where p is 2–6; or Z is —C≡C—, Y is —CR$^{7'}$R$^{7''}$, R$^{7'}$ is hydrogen, alkyl, alkenyl, alkoxy, alkoxyalkyl, substituted alkyl, phenyloxy or substituted phenyloxy, and R$^{7''}$ is phenoxy or substituted phenoxy; or Z is —COO—, —OCO—, —CH$_2$—CH$_2$—, —CH=CH—, —CH$_2$O—, —CH$_2$S—, —COCH$_2$— or —CH$_2$CO—, and Y is N—R$^7$, wherein R$^7$ is alkyl, alkoxyalkyl or substituted alkyl, or Y is —CR$^{7'}$R$^{7'}$, wherein each R$^{7'}$ is independently hydrogen, alkyl, alkenyl, alkoxy, alkoxyalkyl, substituted alkyl, phenyloxy or substituted phenyloxy, or both R$^{7'}$ together are —(CH$_2$)$_p$—, where p is 2–6;

Ar is phenyl, substituted phenyl or a heteroarylic ring; and $R^8$ is hydrogen, lower alkyl or benzyl;

and pharmaceutically acceptable salts of carboxylic acids of formula I–J.

Still further preferred compounds of formula I are those of formula I–K

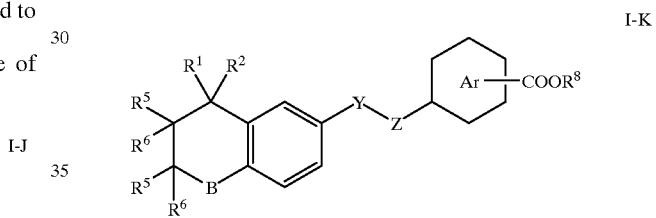

I-K wherein

B is C($R^3R^4$), oxygen, S(O)$_m$ or N-alkyl and m is 0, 1 or 2;

$R^1$, $R^2$, $R^3$, $R^4$, $R^5$ and $R^6$ independently of each other are hydrogen or lower alkyl;

Z is —OCH$_2$— or —SCH$_2$—,

Y is —CR$^{7'}$R$^{7'}$—, and
each R$^{7'}$ is independently hydrogen, alkyl, alkenyl, alkoxy, alkoxyalkyl, substituted alkyl, phenyloxy or substituted phenyloxy, or both R$^{7'}$ together are —(CH$_2$)$_p$—, where p is 2–6; or Z is —C≡C—, Y is —CR$^{7'}$R$^{7''}$, R$^{7'}$ is hydrogen, alkyl, alkenyl, alkoxy, alkoxyalkyl, substituted alkyl, phenyloxy or substituted phenyloxy, and R$^{7''}$ is phenoxy or substituted phenoxy; or Z is —COO—, —OCO—, —CH$_2$—CH$_2$—, —CH=CH—, —CH$_2$O—, —CH$_2$S—, —COCH$_2$— or —CH$_2$CO—, and Y is N—R$^7$, wherein R$^7$ is alkyl, alkoxyalkyl or substituted alkyl, or Y is —CR$^{7'}$R$^{7'}$—, wherein each R$^{7'}$ is independently hydrogen, alkyl, alkenyl, alkoxy, alkoxyalkyl, substituted alkyl, phenyloxy or substituted phenyloxy, or both R$^{7'}$ together are —(CH$_2$)$_p$—, where p is 2–6;

Ar is phenyl, substituted phenyl or a heteroarylic ring; and $R^8$ is hydrogen, lower alkyl or benzyl;

and pharmaceutically acceptable salts of carboxylic acids of formula I–K.

Preferred compounds of formula I–K are those wherein B is C($R^3R^4$), $R^5$ and $R^6$ are H, and Ar is phenyl or substituted phenyl. Within these preferred compounds of formula I–K, most preferred are those wherein Y is —$CR^{7'}R^{7'}$— and Z is selected from the group —COO—, —CH=CH— and —$CH_2O$—.

Further preferred compounds of formula I–K are those wherein B is O, $R^5$ and $R^6$ are H, and Ar is phenyl or substituted phenyl. Within these preferred compounds of formula I–K, most preferred are those wherein Y is —$CR^{7'}R^{7'}$— and Z is selected from the group —COO—, —CH=CH— and —$CH_2O$—.

Still other preferred compounds of formula I–K are those wherein B is S(O)$_m$, $R^5$ and $R^6$ are H, and Ar is phenyl or substituted phenyl. Within these preferred compounds of formula I–K, most preferred are those wherein Y is —$CR^{7'}R^{7'}$— and Z is —CH=CH— or —$CH_2O$—.

Still other preferred compounds of formula I–K are those wherein B is N-alkyl, $R^5$ and $R^6$ are H, and Ar is phenyl or substituted phenyl.

Other preferred compounds of formula I are those of formula I–L

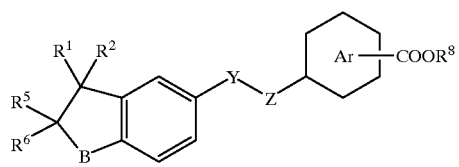

I-L wherein
$R^1$, $R^2$, $R^3$ and $R^4$ independently of each other are hydrogen or lower alkyl;
Z is —$OCH_2$— or —$SCH_2$—,
Y is —$CR^{7'}R^{7'}$—, and
each $R^{7'}$ is independently hydrogen, alkyl, alkenyl, alkoxy, alkoxyalkyl, substituted alkyl, phenyloxy or substituted phenyloxy, or both $R^{7'}$ together are —$(CH_2)_p$—, where p is 2–6; or
Z is —C≡C—,
Y is —$CR^{7'}R^{7''}$,
$R^{7'}$ is hydrogen, alkyl, alkenyl, alkoxy, alkoxyalkyl, substituted alkyl, phenyloxy or substituted phenyloxy, and
$R^{7''}$ is phenoxy or substituted phenoxy; or
Z is —COO—, —OCO—, —$CH_2$—$CH_2$—, —CH=CH—, —$CH_2O$—, —$CH_2S$—, —$COCH_2$— or —$CH_2CO$—, and
Y is N—$R^7$, wherein $R^7$ is alkyl, alkoxyalkyl or substituted alkyl, or Y is —$CR^{7'}R^{7'}$—, wherein each $R^{7'}$ is independently hydrogen, alkyl, alkenyl, alkoxy, alkoxyalkyl, substituted alkyl, phenyloxy or substituted phenyloxy, or both $R^{7'}$ together are —$(CH_2)_p$—, where p is 2–6;
Ar is phenyl, substituted phenyl or a heteroarylic ring; and
$R^8$ is hydrogen, lower alkyl or benzyl;
and pharmaceutically acceptable salts of carboxylic acids of formula I–L.

Preferred compounds of formula I–L are those wherein B is C($R^3R^4$), $R^5$ and $R^6$ are H and Ar is phenyl or substituted phenyl.

Other preferred compounds of formula I–L are those wherein B is oxygen, S(O)$_m$ or N-alkyl; $R^5$ and $R^6$ are H and Ar is phenyl or substituted phenyl.

Still other preferred compounds of formula I are those of formula I–M

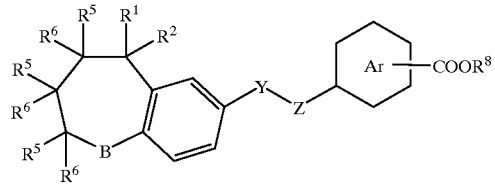

I-M wherein
B is C($R^3R^4$), oxygen, S(O)$_m$ or N-alkyl and
m is 0, 1 or 2;
$R^1$, $R^2$, $R^3$, $R^4$, $R^5$ and $R^6$ independently of each other are hydrogen or lower alkyl;
Z is —$OCH_2$— or —$SCH_2$—,
Y is —$CR^{7'}R^{7'}$—, and
each $R^{7'}$ is independently hydrogen, alkyl, alkenyl, alkoxy, alkoxyalkyl, substituted alkyl, phenyloxy or substituted phenyloxy, or both $R^{7'}$ together are —$(CH_2)_p$—, where p is 2–6; or
Z is —C≡C—,
Y is —$CR^{7'}R^{7''}$,
$R^{7'}$ is hydrogen, alkyl, alkenyl, alkoxy, alkoxyalkyl, substituted alkyl, phenyloxy or substituted phenyloxy, and
$R^{7''}$ is phenoxy or substituted phenoxy; or
Z is —COO—, —OCO—, —$CH_2$—$CH_2$—, —CH=CH—, —$CH_2O$—, —$CH_2S$—, —$COCH_2$— or —$CH_2CO$—, and
Y is N—$R^7$, wherein $R^7$ is alkyl, alkoxyalkyl or substituted alkyl, or
Y is —$CR^{7'}R^{7'}$—, wherein each $R^{7'}$ is independently hydrogen, alkyl, alkenyl, alkoxy, alkoxyalkyl, substituted alkyl, phenyloxy or substituted phenyloxy, or both $R^{7'}$ together are —$(CH_2)_p$—, where p is 2–6;
Ar is phenyl, substituted phenyl or a heteroarylic ring; and
$R^8$ is hydrogen, lower alkyl or benzyl;
and pharmaceutically acceptable salts of carboxylic acids of formula I–M.

Preferred compounds of formula I–M are those wherein B is C($R^3R^4$), $R^5$ and $R^6$ are H and Ar is phenyl or substituted phenyl.

Other preferred compounds of formula I–M are those wherein B is oxygen, S(O)$_m$ or N-alkyl; $R^5$ and $R^6$ are H and Ar is phenyl or substituted phenyl.

In another aspect, this invention is concerned with the use of RAR selective agonist with systemic administration being a preferred mode of delivery for treating emphysema and associated pulmonary diseases. It is thus concerned with a method for treating emphysema and associated pulmonary diseases by treatment of a mammal with a RAR selective agonist with systemic administration being a preferred mode of delivery.

A "therapeutically effective amount" means the amount of a compound that, when administered to a mammal for treating or preventing a disease, is sufficient to effect such treatment or prevention for the disease. The "therapeutically effective amount" will vary depending on the compound, the disease and its severity and the age, weight, etc., of the mammal to be treated.

The RARγ agonist selectivity of a compound can be determined by routine ligand binding assays known to one skilled in the art such as described in C. Apfel et al. *Proc. Nat. Sci. Acad.* (USA), 89:7129–7133 (1992); M. Teng et al., *J. Med. Chem.*, 40:2445–2451 (1997); and PCT Publication WO 96/30009.

The uses of the RAR agonists of formulae I–A through I–M disclosed herein may be used for promoting the repair of damaged alveoli and septation of new alveoli, particularly for the treatment emphysema. Treatment with RAR agonists, particularly, RARγ selective agonists is useful to promote repair of alveolar matrix and septation. As such, the methods disclosed herein are useful for treating diseases such as emphysema.

Typically, the dosage will range between about 0.01 and 1.0 mg/kg body weight per day, preferably from about 0.05 to about 0.5 mg/kg body weight per day.

In particular dosage of a RAR selective agonist required to treat lung emphysema will depend on the severity of the condition. This dosage may be delivered in a conventional pharmaceutical composition by a single administration, by multiple applications, or via controlled release, as needed to achieve the most effective results. Dosing will continue for as long as is medically indicated, which depending on the severity of the disease may range from a few weeks to several months.

Typically, a pharmaceutically acceptable composition, such as a salt, of the RAR agonist of formula I in a pharmaceutically acceptable carrier or diluent is administered. In the context of the present invention, pharmaceutically acceptable salts include any chemically suitable salt known in the art of retinoid agonists as applicable for administration to human patients. Examples of conventional salts known in the art include the alkali metal salts such as sodium and potassium salts, the alkaline earth metal salts such as calcium and magnesium salts, and ammonium and alkyl ammonium salts.

Representative delivery regimens include oral, parenteral (including subcutaneous, intramuscular and intravenous), rectal, buccal (including sublingual), transdermal, pulmonary and intranasal. One method of pulmonary administration involves aerosolization of a solution of an RAR agonist. Aerosolized compositions may include the compound packaged in reverse micelles or liposomes. Typical pulmonary and respiratory delivery systems are described in U.S. Pat. Nos. 5,607,915, 5,238,683, 5,292,499, and 5,364,615.

The treatment methods of this invention also include systemic administration of RAR agonists in simultaneous or sequential combination with a further active ingredient.

RAR agonists will typically be administered as pharmaceutical compositions in admixture with a pharmaceutically acceptable, non toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for intranasal administration, particularly in the form of powders, nasal drops or aerosols; and for rectal or transdermal administration. Any conventional carrier material can be employed. The carrier material can be any organic or inorganic carrier material, such as water, gelatin, gum arabic, lactose, starch, magnesium stearate, talc, polyalkylene glycols, petroleum jelly and the like.

Liquid formulations for parenteral administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM. For oral administration, the formulation can be enhanced by the addition of bile salts or acylcarnitines.

Formulations for nasal administration may be solid and may contain excipients, for example, lactose or dextran, or may be aqueous or oily solutions for use in the form of nasal drops or metered spray. Particular nasal formulations include dry powders suitable for conventional dry powder inhalers (DPI's), liquid solutions or suspensions suitable for nebulization and propellant formulations suitable for use in metered dose inhalers (MDI's). For buccal administration typical excipients include sugars, calcium stearate, magnesium stearate, pregelatinated starch, and the like.

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Solid forms for oral administration include tablets, hard and soft gelatin capsules, pills, sachets, powders, granules and the like. Each tablet, pill or sachet may contain from about 1 to about 50 mg, preferably from 5 to about 10 mg of RAR agonist. Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; Pharmaceutical Technology, 9, (1985). Some of the advantages of using SEG capsules are: a) dose-content uniformity is optimized in SEG capsules because the drug is dissolved or dispersed in a liquid that can be dosed into the capsules accurately b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area and c) degradation of drugs that are sensitive to oxidation during long-term storage is prevented because of the dry shell.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

The following are representative pharmaceutical formulations for using RAR selective agonists as described herein for promoting elastin mediated matrix repair and alveolar septation.

Tablet Formulation

The following ingredients are mixed intimately and pressed into single scored tablets.

| Quantity per Ingredient | tablet, mg |
|---|---|
| RAR agonist | 10 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| RAR agonist | 5 |
| lactose, spray-dried | 148 |
| magnesium stearate | 2 |

Suspension Formulation

The following ingredients are mixed to form a suspension for oral administration.

| Ingredient | Amount |
|---|---|
| RAR agonist | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| RAR agonist | 0.2 g |
| sodium acetate buffer solution, 0.4M | 2.0 ml |
| HCl (1N) or NaOH (1N) | q.s. to suitable pH |
| water (distilled, sterile) | q.s. to 20 ml |

Nasal Formulation

The following ingredients are mixed to form a suspension for nasal administration.

| Ingredient | Amount |
|---|---|
| RAR agonist | 20 mg/ml |
| citric acid | 0.2 mg/ml |
| sodium citrate | 2.6 mg/ml |
| benzalkonium chloride | 0.2 mg/ml |
| sorbitol | 35 mg/ml |
| sodium taurocholate or glycocholate | 10 mg/ml |

The following preparations and examples are given to enable those skilled in the art to more clearly understand and to practice the present invention.

EXAMPLE 1

1.1 Preparation of (R,S)-2-(5,5,8,8-tetramethyl-5,6,7,8-tetrahydro-naphthalen-2-yl)-heptanoic Acid 2.85 ml of diisopropylamine were dissolved in 80 ml THF (tetrahydrofuran) abs. and treated dropwise, at 0° C., with 12.7 ml of BuLi (butyl lithium, 1.6M in hexane). After 30 minutes at 0° C., a solution of 2.0 g of (5,5,8,8-tetramethyl-5,6,7,8-tetrahydronaphthalen-2-yl)-acetic acid in 20 ml THF was dropped in. The reaction mixture was stirred at 0° C. for 1 hour then at room temperature for 30 minutes. After cooling back to 0° C., a solution of 1.6 ml of pentyl iodide in 5 ml THF was added dropwise. The mixture was kept at 0° C. for 1 hour then at room temperature for 2 hours. The reaction was quenched with the addition of 50 ml water and the pH was adjusted to 2 with HCl 25%. The mixture was extracted with 3 portions of 50 ml diethylether. The combined organic extracts were washed with 2 portions of 25 ml of a saturated solution of sodium thiosulfate, 1 portion of 25 ml of water and 1 portion of 25 ml of saturated aqueous NaCl. The organic phase was dried over $MgSO_4$ and the solvent evaporated to yield an orange oil. Flash chromatography ($SiO_2$, 20% ethyl acetate/hexane) gave 2.37 g of a pale yellow oil, which solidified upon standing, m.p. 108–110° C.

In analogy to example 1.1., by using a corresponding alkyliodide, alkylbromide or benzyl bromide, the following compounds were synthesized:

1.1 (RS)-2-(5,5,8,8-Tetramethyl-5,6,7,8-tetrahydronaphthalen-2-yl)-propanoic acid, 1H NMR (DMSO-d6): 12.21 (s, 1H), 7.25 (d, J=8.1 Hz, 1H), 7.19 (d, J=2.0 Hz, 1H), 7.00 (dd, J=2.0, 8.0 Hz, 1H), 3.58 (q, J=13.0 Hz, 1H), 1.62 (s, 4H), 1.32 (d, J=7.1 Hz, 3H), 1.22 (s, 12H).

1.2 (RS)-2-(5,5,8,8-Tetramethyl-5,6,7,8-tetrahydronaphthalen-2-yl)-pentanoic acid, 1H NMR (DMSO-d6): 12.21 (s, 1H), 7.24 (d, J=8.2 Hz, 1H), 7.19 (d, J=1.9 Hz, 1H), 7.01 (dd, J=1.9, 8.0 Hz, 1H), 3.43 (m, 1H), 1.89 (m, 1H), 1.62 (s, 4H), 1.55 (m, 1H), 1,25 (m, 2H), 1.22 (s, 6H), 1.21 (s, 6H), 0.86 (t, J=7.3 Hz, 3H).

1.3 (RS)-(E)-2-(5,5,8,8-Tetramethyl-5,6,7,8-tetrahydronaphthalen-2-yl)-hex-4-enoic acid, 1H (DMSO-d6): 12.24 (s, 1H), 7.25 (d, J=8.2 Hz, 1H), 7.19 (d, J=1.9 Hz, 1H), 7.02 (dd, J=2.0, 8.2 Hz, 1H), 5.36 (m, 2H), 3.45 (m, 1H), 2.60 (m, 1H), 2.25 (m, 1H), 1.62 (s, 4H), 1.57 (dd, J=1.2, 4.9 Hz, 3H), 1.22 (s, 3H), 1.21 (s, 3H).

1.4 (RS)-2-(5,5,8,8-Tetramethyl-5,6,7,8-tetrahydronaphthalen-2-yl)-hexanoic acid, 1H NMR (DMSO-d6): 12.15 (s, 1H), 7.24 (d, J=8.2 Hz, 1H), 7.19 (d, J=1.9 Hz, 1H), 7.01 (dd, J=2.0, 8.0 Hz, 1H), 3.40 (m, 1H), 1.89 (m, 1H), 1.64 (m, 2H), 1.62 (s, 4H), 1.24 (m, 4H), 1.22 (s, 6H), 1.21 (s, 6H), 0.83 (t, J=7.3 Hz, 3H).

1.5 (RS)-2-(5,5,8,8-Tetramethyl-5,6,7,8-tetrahydronaphthalen-2-yl)-decanoic acid, 1H (DMSO-d6): 12.24 (s, 1H), 7.24 (d, J=8.1 Hz, 1H), 7.18 (d, J=2.2 Hz, 1H), 7.01 (dd, J=2.1, 8.1 Hz, 1H), 3.39 (m, 1H), 1.73 (m, 2H), 1.64 (m, 2H), 1.62 (s, 4H), 1.27 (m, 20H), 0.85 (t, J=6.6 Hz, 3H).

1.6 (RS)-4-Methyl-2-(5,5,8,8-tetramethyl-5,6,7,8-tetrahydronaphthalen-2-yl)-pentanoic acid, 1H NMR (DMSO-d6): 12.19 (s, 1H), 7.24 (d, J=8.2 Hz, 1H), 7.20 (d, J=1.8 Hz, 1H), 7.02 (dd, J=1.8, 8.0 Hz, 1H), 3.49 (m, 1H), 1.80 (m, 1H), 1.62 (s, 4H), 1.44 (m, 2H), 1.22 (s, 6H), 1.21 (s, 6H), 0.86 (d, J=6.5 Hz, 6H).

1.7 (RS)-3-Phenyl-2-(5,5,8,8-tetramethyl-5,6,7,8-tetrahydronaphthalen-2-yl-propanoic acid, yellow oil, 1H NMR (CDCl₃): 7.05–7.25 (m, 8H), 3.82 (dd, J=10.5, 7.3 Hz, 1H), 3.39 (dd, J=15, 10.5 Hz, 1H), 3.00 (dd, J=15, 7.3 Hz, 1H), 1.66 (s, 4H), 1.26 (s, 9H), 1.19 (s, 1H).

1.8 (RS)-3-(4-Chlorophenyl)-2-(5,5,8,8-tetramethyl-5,6,7,8-tetrahydronaphthalen-2-yl)-propanoic acid, yellow solid, 1H NMR (CDCl₃): 7.0–7.3 (m, 7H), 3.77 (t, J=9.0 Hz, 1H), 3.36 (dd, J=15.6, 9.0 Hz, 1H), 2.92 (dd, J=15.6, 9.0 Hz, 1H), 1.67 (s, 4H), 1.26 (s, 9H), 1.20 (s, 3H).

1.9 (RS)-2-(5,5,8,8-Tetramethyl-5,6,7,8-tetrahydronaphthalen-2-yl)-3-(4-trifluoromethylphenyl)-propanoic acid, yellow solid, 1H NMR (CDCl₃): 7.48 (d, J=9.6 Hz, 2H), 7.25 (m, 1H), 7.21 (d, J=9.5 Hz, 2H), 7.08 (m, 2H), 3.80 (dd, J=9.6, 9.0 Hz, 1H), 3.44 (dd, J=15.3, 9.6 Hz, 1H), 3.05 (dd, J=15.4, 9.0 Hz, 1H), 1.65 (s, 4H), 1.26 (s, 6H), 1.24 (s, 3H), 1.15 (s, 3H).

1.10 (RS)-4-Phenyl-2-(5,5,8,8-tetramethyl-5,6,7,8-tetrahydronaphthalen-2-yl)-butanoic acid, pale yellow solid, 1H NMR (CDCl₃): 7.04–7.35 (m, 8H), 3.52 (t, J=8.1 Hz, 1H), 2.61 (t, J=7.8 Hz, 2H), 2.40 (m, 1H), 2.10 (m, 1H), 1.66 (s, 4H), 1.26 (s, 12H).

1.11 (RS)-4-Ethoxy-2-(5,5,8,8-tetramethyl-5,6,7,8-tetrahydronaphthalen-2-yl)-butanoic acid, yellow oil, 1H NMR (CDCl₃): 7.23 (d, J=8.0 Hz, 1H), 7.20 (d, J=2.0 Hz, 1H), 7.07 (dd, J=8.0, 2.0 Hz, 1H), 3.74 (t, J=7.6 Hz, 1H), 3.30–3.60 (m, 4H), 2.35 (m, 1H), 1.96 (m, 1H), 1.66 (s, 4H), 1.27 (s, 3H), 1.26 (s, 3H), 1.25 (s, 6H), 1.17 (t, J=7.0 Hz, 3H).

1.12 (RS)-3-(4-Fluorophenyl)-2-(5,5,8,8-tetramethyl-5,6,7,8-tetrahydronaphthalen-2-yl)-propanoic acid, 1H NMR (DMSO): 12.28 (br s, 1H), 7.3–7.15 (m, 4H), 7.1–7.0 (m, 3H), 3.78 (dd, J=9.3, 6.3 Hz, 1H), 3.22 (dd, J=13.7, 9.3 Hz, 1H), 2.87 (dd, J=13.7, 6.3 Hz, 1H), 1.61 (s, 4H), 1.22 (s, 9H), 1.21 (s, 3H).

1.13 (RS)-3-(3-Fluorophenyl)-2-(5,5,8,8-tetramethyl-5,6,7,8-tetrahydronaphthalen-2-yl)-propanoic acid, 1H NMR (CDCl₃): 7.3–7.0 (m, 5H), 6.95–6.7 (m, 2H), 3.78 (dd, J=9.0, 6.4 Hz, 1H), 3.38 (dd, J=13.8, 9.0 Hz, 1H), 2.98 (dd, J=13.8, 6.4 Hz, 1H), 1.66 (s, 4H), 1.27 (s, 3H), 1.25 (s, 3H), 1.24 (s, 3H), 1.18 (s, 3H).

1.14 (RS)-3-(3-Chlorophenyl)-2-(5,5,8,8-tetramethyl-5,6,7,8-tetrahydronaphthalen-2-yl)-propanoic acid, 1H NMR (CDCl₃): 7.3–6.9 (m, 7H), 3.76 (dd, J=8.7, 6.7 Hz, 1H), 3.34 (dd, J=13.7, 8.7 Hz, 1H), 2.96 (dd, J=13.7, 6.7 Hz, 1H), 1.66 (s, 4H), 1.26 (s, 3H), 1.25 (s, 3H), 1.24 (s, 3H), 1.18 (s, 3H).

1.15 (RS)-3-(4-Methoxyphenyl)-2-(5,5,8,8-tetramethyl-5,6,7,8-tetrahydronaphthalen-2-yl)-propanoic acid, 1H NMR (CDCl₃): 7.24 (d, J=8.5 HZ, 1H), 7.15 (d, J=1.9 Hz, 1H), 7.10 (dd, J=8.2, 2.0 Hz, 1H), 7.04 (d, J=8.7 Hz, 2H), 6.77 (d, J=8.7 Hz, 2H), 3.76 (s, 3H), 3.755 (dd, J=9.3, 6.2 Hz, 1H), 3.32 (dd, J=13.8, 9.3 Hz, 1H), 2.93 (dd, J=13.9, 6.2 Hz, 1H), 1.66 (s, 4H), 1.26 (s, 3H), 1.25 (s, 6H), 1.20 (s, 3H).

EXAMPLE 2

2.1. Preparation of (RS)-benzyl-4-[2-(5,5,8,8-tetramethyl-5,6,7,8-tetrahydronaphthalen-2-yl)-heptanoyloxy]-benzoate 300 mg of 2-(5,5,8,8-Tetramethyl-5,6,7,8-tetrahydronaphthalen-2-yl)-heptanoic acid were dissolved in 10 ml of methylene chloride and to this solution, were added successively, 240 mg of benzyl-4-hydroxybenzoate and 116 mg of N,N-dimethylaminopyridine. The reaction mixture was cooled to 0° C. and 217 mg of 1,3-dicyclohexylcarbodiimide was added at once. The mixture was stirred at 0° C. for 2 hours then at room temperature for 2 hours. The reaction mixture was filtered and the resulting filtrate was washed with 2 portions of 25 ml of water. The organic phase was dried over MgSO₄ and the solvent evaporated. The oil/solid residue was purified by flash chromatography (SiO₂, 10% ethyl acetate/hexanes) and gave 403 mg of a colorless oil, 1H NMR (CDCl₃): 8.07 (d, J=8.8 Hz, 2H), 7.38–7.50 (m, 4H), 7.27 (m, 3H), 7.15 (m, 1H), 7.08 (d, J=8.8 Hz, 2H), 5.35 (s, 2H), 3.73 (dd, J=9.0, 7.5 Hz, 1H), 2.18 (m, 1H), 1.82 (m, 1H), 1.68 (s, 4H), 1.2–1.5 (m, 6H), 1.29 (s, 3H), 1.28 (s, 9H), 0.88 (t, J=7.5 Hz, 3H).

In analogy to example 2.1., the alkylated acids of example 1 were used for the coupling with the appropriate 4-hydroxybenzoic ester;

2.2. (RS)-Benzyl-4-[3-phenyl-2-(5,5,8,8-tetramethyl-5,6,7,8-tetrahydronaphthalen-2-yl)-propanoyloxy]-benzoate, colorless oil, 1H NMR (CDCl₃): 8.02 (d, J=8.8 Hz, 2H), 7.17–7.42 (m, 13H), 6.89 (d, J=8.7 Hz, 2H), 5.33 (s, 2H), 4.06 (dd, J=9.6, 7.2 Hz, 1H), 3.26 (dd, J=13.9, 9.6 Hz, 1H), 3.11 (dd, J=14.0, 7.2 Hz, 1H), 1.68 (s, 4H), 1.28 (s, 12H).

2.3. (RS)-Benzyl-4-[4-phenyl-2-(5,5,8,8-tetramethyl-5,6,7,8-tetrahydronaphthalen-2-yl)-butanoyloxy]-benzoate, colorless oil, 1H NMR (CDCl₃): 8.08 (d, J=8.8 Hz, 2H), 7.02–7.47 (m, 13H), 7.06 (d, J=8.8 Hz, 2H), 5.35 (s, 2H), 3.75 (t, J=9.0 Hz, 1H), 2.68 (t, J=9.0 Hz, 2H), 2.50 (m, 1H), 2.18 (m, 1H), 1.68 (s, 4H), 1.28 (s, 12H).

2.4. (RS)-Allyl-4-[3-(4-chlorophenyl)-2-(5,5,8,8-tetramethyl-5,6,7,8-tetrahydronaphthalen-2-yl)-propanoyloxy]-benzoate, yellow oil, 1H NMR (CDCl₃): 8.03 (d, J=8.4 Hz, 2H), 7.12–7.40 (m, 7H), 6.92 (d, J=8.4 Hz, 2H), 6.04 (m, 1H), 5.40 (dd, J=17.4, 1.2 Hz, 1H), 5.28 (dd, J=10.5, 1.2 Hz, 1H), 4.82 (d, J=7.2 Hz, 2H), 4.02 (dd, J=10.2, 7.5 Hz, 1H), 3.44 (dd, J=15.6, 10.5 Hz, 1H), 3.08 (dd, J=15.4, 7.4 Hz, 1H), 1.68 (s, 4H), 1.28 (s, 9H), 1.24 (s, 3H).

2.5. (RS)-Benzyl-4-[2-(5,5,8,8-tetramethyl-5,6,7,8-tetrahydronaphthalen-2-yl)-3-(4-trifluoromethylphenyl)-propanoyloxy]-benzoate, pale yellow oil, 1H NMR (CDCl₃): 8.04 (d, J=8.4 Hz, 2H), 7.52 (d, J=7.5 Hz, 2H), 7.10–7.48 (m, 10H), 6.92 (d, J=8.4 Hz, 2H), 5.34 (s, 2H), 4.04 (dd, J=9.6, 7.5 Hz, 1H), 3.52 (dd, J=1.8, 9.6 Hz, 1H), 3.15 (dd, J=13.9, 7.5 Hz, 1H), 1.68 (s, 4H), 1.28 (s, 9H), 1.20 (s, 3H).

2.6. (RS)-Benzyl-4-[4-ethoxy-2-(5,5,8,8-tetramethyl-5,6,7,8-tetrahydronaphthalen-2-yl)-butanoyloxy]-benzoate, colorless oil, 1H NMR (CDCl₃): 8.06 (d, J=8.4 Hz, 2H), 7.33–7.43 (m, 5H), 7.28 (d, J=2.0 Hz, 1H), 7.26 (d, J=2.7 Hz, 1H), 7.12 (dd, J=8.0, 2.0 Hz, 1H), 7.09 (d, J=7.2 Hz, 2H), 5.35 (s, 2H), 3.97 (t, J=7.2 Hz, 1H), 3.36–3.53 (m, 4H), 2.47 (m, 1H), 2.03 (m, 1H), 1.68 (s, 4H), 1.28 (s, 3H), 1.27 (s, 9H), 1.21 (t, J=7.2 Hz, 3H).

2.7. (RS)-Benzyl-4-[3-(4-fluorophenyl)-2-(5,5,8,8-tetramethyl-5,6,7,8-tetrahydronaphthalen-2-yl)-propanoyloxy]-benzoate, 1H NMR (CDCl₃): 8.04 (d, J=8.9 Hz, 2H), 7.45–7.20 (m, 8H), 7.20–7.10 (m, 2H), 7.05–6.85 (m, 4H), 5.34 (s, 2H), 4.00 (dd, J=9.7, 6.1 Hz, 1H), 3.42 (dd, J=13.7, 9.7 Hz, 1H), 3.07 (dd, J=13.7, 6.1 Hz, 1H), 1.68 (s, 4H), 1.28 (s, 9H), 1.23 (s, 3H).

2.8. (RS)-Benzyl-4-[3-(3-fluorophenyl)-2-(5,5,8,8-tetramethyl-5,6,7,8-tetrahydronaphthalen-2-yl)- propanoyloxy]-benzoate, 1H NMR (CDCl$_3$): 8.04 (d, J=8.9 Hz, 2H), 7.45–7.10 (m, 11H), 7.05–6.85 (m, 3H), 5.34 (s, 2H), 4.04 (dd, J=9.5, 6.0 Hz, 1H), 3.45 (dd, J=13.8, 9.7 Hz, 1H), 3.09 (dd, J=13.7, 6.0 Hz, 1H), 1.68 (s, 4H), 1.28 (s, 9H), 1.23 (s, 3H).

EXAMPLE 3

3.1. Preparation of (RS)-4-[2-(5,5,8,8-tetramethyl-5,6,7,8-tetrahydronaphthalen-2-yl)-heptanoyloxy]-benzoic Acid 403 mg of (RS)-Benzyl-4-[2-(5,5,8,8-tetramethyl-5,6,7,8-tetrahydronaphthalen-2-yl)-heptanoyloxy]-benzoate in 10 ml of ethyl acetate with 80 mg of palladium on carbon (10% w/w) was subjected to an atmospheric pressure of hydrogen for 1 hour. The mixture was filtered over Celite and washed with about 10 ml ethyl acetate. The solution was evaporated, giving a colorless oil. Trituration in pentane gave a white amorphous solid, 303 mg, m.p. 133–135° C.

In analogy to example 3.1., the benzyl esters of example 2 were used in the same way, giving:

3.2. (RS)-4-[3-Phenyl-2-(5,5,8,8-tetramethyl-5,6,7,8-tetrahydronaphthalen-2-yl)-propanoyloxy]-benzoic acid, amorphours white solid, m.p. 163–164° C.

3.3. (RS)-4-[4-Phenyl-2-(5,5,8,8-tetramethyl-5,6,7,8-tetrahydronaphthale-2-yl)-butanoyloxy]-benzoic acid, amorphous white solid, m.p. 124–125° C.

3.4. (RS)-4-[2-(5,5,8,8-Tetramethyl-5,6,7,8-tetrahydronaphthalen-2-yl)-3-(4-trifluoromethylphenyl)-propanoyloxy]-benzoic acid, amorphous white solid, m.p. 158–159° C.

3.5. (RS)-4-[4-Ethoxy-2-(5,5,8,8-tetramethyl-5,6,7,8-tetrahydronaphthalen-2-yl)-butanoyloxy]-benzoic acid, colorless solid, m.p. 133–134° C.

3.6. [(RS)-4-[3-(4-Fluorophenyl)-2-(5,5,8,8-tetramethyl-5,6,7,8-tetrahydronaphthalen-2-yl)-propanoyloxy]-benzoic acid], white solid, m.p. 164–165° C.

3.7. [(RS)-4-[3-(3-Fluorophenyl)-2-(5,5,8,8-tetramethyl-5,6,7,8-tetrahydronaphthalen-2-yl)-propanoyloxy]-benzoic acid], white solid, m.p. 171–172° C.

EXAMPLE 4

4.1 Preparation of (RS)-4-[3-(4-chlorophenyl)-2-(5,5,8,8-tetramethyl-5,6,7,8-tetrahydronaphthalen-2-yl)-propanoyloxy]-benzoic Acid 260 mg of (RS)-Allyl-4-[3-(4-chorophenyl)-2-(5,5,8,8-tetramethyl-5,6,7,8-tetrahydronaphthalen-2-yl)-propanoyloxy]-benzoate (of example 2.4.) were dissolved in 6 ml THF. The reaction flask was evacuated and ventilated with argon twice. 58 mg of tetrakis(triphenylphosphine) palladium were added, followed by 0.4 ml of morpholine. The reaction mixture was stirred at room temperature for 6 hours. The mixture was quenched by the addition of 20 ml water and the pH was adjusted to 2 with HCl 25%. The mixture was extracted with 3 portions of 25 ml of ethyl acetate. The combined organic extracts were washed with 1 portion of 25 ml of water and 1 portion of 25 ml of a saturated aqueous solution of NaCl. The organic phase was dried over MgSO$_4$ and the solvent evaporated, yielding an orange oil. The product was purified by flash chromatography (SiO$_2$, 75% ethyl acetate/hexanes) to a yellow foam. Trituration in pentane (+ drops of diethylether) gave 157 mg of a pale yellow solid, m.p. 129–130° C.

EXAMPLE 5

5.1 Preparation of (RS)-2-(5,5,8,8-tetramethyl-5,6,7,8-tetrahydronaphthalen-2-yl)-heptanol 725 mg of (RS)-2-(5,5,8,8-Tetramethyl-5,6,7,8-tetrahydronaphthalen-2-yl)-heptanoic acid were dissolved in 10 ml THF and treated dropwise, at 0° C., with 11.5 ml of BH$_3$.THF). The reaction mixture was stirred at 0° C. for 2 hours. The mixture was carefully quenched at 0° C. with a portion of 10 ml of HCl (3N). The mixture was stirred at room temperature for 30 minutes then it was extracted with 3 portions of 50 ml of ethyl acetate. The organic phase was dried over MgSO$_4$ and the solvent evaporated, giving a pale yellow oil. The product was purified by flash chromatography (SiO$_2$, 20% ethyl acetate/hexanes) to yield 556 mg of a colorless oil, 1H NMR (CDCl$_3$): 7.27 (d, J=9.6 Hz, 1H), 7.10 (d, J=1.5 Hz, 1H), 6.95 (dd, J=9.6, 1.5 Hz, 1H), 3.71 (m, 2H), 2.72 (m, 1H), 1.67 (s, 4H), 1.60 (m, 2H), 1.20–1.35 (m, 6H), 1.27 (s, 12H), 0.84 (t, J=7.5 Hz, 3H).

In analogy to example 5.1, by using the appropriate acids from example 1, the following compounds were synthesized:

5.2. (RS)-3-Phenyl-2-(5,5,8,8-tetramethyl-5,6,7,8-tetrahydronaphthalen-2-yl)-propanol, colorless oil, 1H NMR (CDCl$_3$): 6.95–7.30 (m, 8H), 3.74 (t, J=6.6 Hz, 2H), 2.97 (m, 3H), 1.66 (s, 4H), 1.26 (s, 6H), 1.25 (s, 3H), 1.21 (s, 3H).

5.3. (RS)-3-(4-Chlorophenyl)-2-(5,5,8,8-tetramethyl-5,6,7,8-tetrahydronaphthalen-2-yl)-propanol, yellow oil, 1H NMR (CDCl$_3$): 7.10–7.35 (m, 3H), 6.92–7.10 (m, 4H), 3.75 (d, J=7.2 Hz, 2H), 3.00 (m, 2H), 2.85 (m, 1H), 1.66 (s, 4H), 1.26 (s, 6H), 1.24 (s, 3H), 1.20 (s, 3H).

5.4. (RS)-2-(5,5,8,8-Tetramethyl-5,6,7,8-tetrahydronaphthalen-2-yl)-3-(4-trifluoromethylphenyl)-propanol, pale yellow oil, 1H NMR (CDCl$_3$): 7.44 (d, J=8.4 Hz, 2H), 7.27 (d, J=9.0 Hz, 1H), 7.18 (d, J=8.4 Hz, 2H), 6.96 (m, 2H), 3.76 (d, J=6.6 Hz, 2H), 2.83–3.18 (m, 3H), 1.65 (s, 4H), 1.26 (s, 6H), 1.22 (s, 3H), 1.16 (s, 3H).

5.5. (RS)-4-Phenyl-2-(5,5,8,8-tetramethyl-5,6,7,8-tetrahydronaphthalen-2-yl)-butanol, colorless oil, 1H NMR (CDCl$_3$): 7.07–7.32 (m, 7H), 6.98 (dd, J=8.4, 1.5 Hz, 1H), 3.72 (d, J=7.2 Hz, 2H), 2.75 (m, 1H), 2.52 (m, 2H), 1.95 (m, 2H), 1.68 (s, 4H), 1.29 (s, 3H), 1.28 (s, 9H).

5.6. 2-(5,5,8,8-Tetramethyl-5,6,7,8-tetrahydronaphthalen-2-yl)-ethanol, 1H NMR (CDCl$_3$): 7.24 (d, J=8.0 Hz, 1H), 7.13 (d, J=1.9 Hz, 1H), 6.98 (dd, J=8.0, 1.9 Hz, 1H), 3.79 (br. q, J=6.1 Hz, 2H), 2.79 (t, J=6.6 Hz, 2H), 1.67 (s, 4H), 1.27 (s, 6H), 126 (s, 6H).

EXAMPLE 6

6.1. Preparation of (RS)-N-methoxy-N-methyl 2-(5,5,8,8-tetramethyl-5,6,7,8-tetrahydronaphthalen-2-yl)-propanoic Amide 0.5 g of (RS)-2-(5,5,8,8-tetramethyl-5,6,7,8-tetrahydronaphthalen-2-yl)-propanoic acid was dissolved in mixture of 5 ml of DMF and 10 ml of dichloromethane, and 1.9 g of MeO(Me)NH.HCl was added followed by 3.3 ml of diisopropylethylamine and 0.72 g of 1-(3-dimethyl) aminopropyl)-3-ethylcarbodiimide hydrochloride. The reaction mixture was stirred at room temperature for 4 h, then dichloromethane was removed on rotary evaporator, and the residue was poured into ethyl acetate (200 ml), washed with water (1×100 ml), 1N HCl (1×50 ml), sat. sodium bicarbonate (1×50 ml), brine (1×50 ml). The organic layer was separated, dried over MgSO$_4$, concentrated, and a residue was used in next step without further purification. Yield 95%. 1H NMR (CDCl$_3$): 7.22 (d, J=8.2 Hz, 1H), 7.19 (d, J=2.0 Hz, 1H), 7.0 (dd, J=2.0, 8.2 Hz, 1H), 4.09 (m, 1H), 3.39 (br s, 3H), 3.15 (s, 3H), 1.66 (s, 4H), 1.42 (d, J=7.0 Hz, 3H), 1.27 (s, 3H), 1.26 (s, 3H), 1.25 (s, 3H), 1.24 (s, 3H).

In analogy to example 6.1, by using the appropriate acids from example 1, the following compounds were synthesized:

6.2. (RS)-N-Methoxy-N-methyl 2-(5,5,8,8-tetramethyl-5,6,7,8-tetrahydronaphthalen-2-yl)-pentanoic amide, 1H NMR (CDCl$_3$): 7.20 (m, 2H), 7.08 (dd, J=2.0, 8.0 Hz, 1H), 3.96 (m, 1H), 3.47 (br s, 3H), 3.15 (s, 3H), 2.03 (m, 1H), 1.65 (s, 4H), 1.67 (m, 1H), 1.27 (m, 2H), 1.26 (s, 3H), 1.25 (s, 3H), 1.24 (s, 3H), 1.23 (s, 3H), 0.90 (t, J=7.3 Hz, 3H).

6.3. (RS)-N-Methoxy-N-methyl 2-(5,5,8,8-tetramethyl-5,6,7,8-tetrahydronaphthalen-2-yl)-hexanoic amide, 1H NMR (CDCl$_3$): 7.20 (m, 2H), 7.08 (dd, J=2.0, 8.0 Hz, 1H), 3.93 (m, 1H), 3.47 (s, 3H), 3.15 (s, 3H), 2.04 (m, 1H), 1.67 (m, 1H), 1.65 (s, 4H), 1.31 (m, 4H), 1.26 (s, 3H), 1.25 (s, 3H), 1.24 (s, 3H), 1.23 (s, 3H), 0.87 (t, J=7.3 Hz, 3H).

6.4. (RS)-N-Methoxy-N-methyl 4-methyl-2-(5,5,8,8-tetramethyl-5,6,7,8-tetrahydronaphthalen-2-yl)-pentanoic amide, 1H NMR (CDCl$_3$): 7.20 (m, 2H), 7.08 (dd, J=1.8, 8.0 Hz, 1H), 4.08 (m, 1H), 3.49 (s 3H), 3.15 (s, 3H), 1.98 (m, 1H), 1.65 (s, 4H), 1.52 (m, 2H), 1.26 (s, 3H), 1.25 (s, 3H), 1.24 (s, 3H), 1.23 (s, 3H), 0.91 (d, J=6.5 Hz, 3H), 0.89 (d, J=6.5 Hz, 3H).

6.5. (RS)-N-methoxy-N-methyl 2-(5,5,8,8-tetramethyl-5,6,7,8-tetrahydronaphthalen-2-yl)-hex-4-enoic amide, 1H NMR (CDCl$_3$): 7.19 (m, 2H), 7.07 (dd, J=2.0, 8.1 Hz, 1H), 5.40 (m, 2H), 3.97 (m, 1H), 3.46 (s, 3H), 3.15 (s, 3H), 2.76 (m, 1H), 2.34 (m, 1H), 1.65 (s, 4H), 1.61 (dd, J=1.1, 4.8 Hz, 3H), 1.26 (s, 3H), 1.25 (s, 6H), 1.24 (s, 3H).

6.6. (RS)-N-Methoxy-N-methyl 2-(5,5,8,8-tetramethyl-5,6,7,8-tetrahydronaphthalen-2-yl)-decanoic amide, 1H NMR (CDCl$_3$): 7.19 (m, 2H), 7.07 (dd, J=2.1,8.1 Hz, 1H), 3.93 (m, 1H), 3.47 (s, 3H), 3.15 (s, 3H), 2.03 (m, 1H), 1.67 (m, 1H), 1.65 (s, 4H), 1.26 (s, 3H), 1.25 (s, 3H), 1.24 (s, 3H), 1.23 (s, 3H), 1.22 (m, 10H), 0.86 (t, J=6.6 Hz, 3H).

6.7. (RS)-N-methoxy-N-methyl 3-(4-fluorophenyl)-2-(5,5,8,8-tetramethyl-5,6,7,8-tetrahydronaphthalen-2-yl)-propanoic amide, 1H NMR (CDCl$_3$): 7.23 (d, J=8.9 Hz, 2H), 7.15–7.00 (m, 3H), 6.90 (t, J=8.8 Hz, 2H), 4.19 (br., 1H), 3.41 (dd, J=13.5, 9.2 Hz, 1H), 3.26 (br. s, 3H), 3.09 (s, 3H), 2.89 (dd, J=13.5, 6.1 Hz, 1H), 1.65 (s, 4H), 1.25 (s, 3H), 1.24 (s, 3H), 1.23 (s, 3H), 1.19 (s, 3H).

6.8. (RS)-N-methoxy-N-methyl 3-(3-chlorophenyl)-2-(5,5,8,8-tetramethyl-5,6,7,8-tetrahydronaphthalen-2-yl)-propanoic amide, 1H NMR (CDCl$_3$): 7.30–6.95 (m, 7H), 4.18 (br., 1H), 3.38 (dd, J=13.4, 8.7 Hz, 1H), 3.27 (br. s, 3H), 3.10 (s, 3H), 2.90 (dd, J=13.4, 6.6 Hz, 1H), 1.65 (s, 4H), 1.27 (s, 3H), 1.26 (s, 3H), 1.24 (s, 3H), 1.23 (s, 3H).

6.9. (RS)-N-methoxy-N-methyl 3-(4-methoxyphenyl)-2-(5,5,8,8-tetramethyl-5,6,7,8-tetrahydronaphthalen-2-yl)-propanoic amide, 1H NMR (CDCl$_3$): 7.35–7.10 (m, 3H), 7.05 (d, J=8.6 Hz, 2H), 6.78 (d, J=8.7 Hz, 2H), 4.20 (br., 1H), 3.76 (s, 3H), 3.42 (dd, J=13.6, 9.5 Hz, 1H), 3.26 (br. s, 3H), 3.08 (s, 3H), 2.87 (dd, J=13.3, 5.6 Hz, 1H), 1.65 (s, 4H), 1.27 (s, 3H), 1.24 (s, 6H), 1.21 (s, 3H).

EXAMPLE 7

7.1. Preparation of (RS)-2-(5,5,8,8-tetramethyl-5,6,7,8-tetrahydronaphthalen-2-yl)-heptanal A solution of 0.35 ml of oxalyl chloride in 20 ml of methylene chloride was treated, at −78° C., with 0.4 ml of DMSO absolute. The mixture was stirred at −78° C. for 5 minutes then 554 mg of (RS)-2-(5,5,8,8-tetramethyl-5,6,7,8-tetrahydronaphthalen-2-yl)-heptanol dissolved in 4 ml of methylene chloride were added dropwise. The reaction mixture was stirred at −78° C. for 15 minutes. 1.3 ml of triethylamine were added and the mixture was stirred 15 minutes at −78° C. then 2.5 hours at room temperature. The mixture was quenched with 20 ml water and extracted with 3 portions of 20 ml of methylene chloride. The combined extracts were washed with 2 portions of 5 ml of water and 1 portion of 50 ml of a saturated aqueous solution of NaCl. The organic phase was dried over MgSO$_4$ and the solvent evaporated to yield a yellow oil. The product was purified with flash chromatography (SiO$_2$, 5% ethyl acetate/hexanes), to yield 483 mg of a colorless oil, 1H NMR (CDCl$_3$): 9.64 (d, J=2.0 Hz, 1H), 7.30 (d, J=8.4 Hz, 1H), 7.08 (d, J=3.0 Hz, 1H), 6.95 (dd, J=8.4, 3.0 Hz, 1H), 3.43 (td, J=7.2, 2.0 Hz, 1H), 2.05 (m, 1H), 1.70 (m, 1H), 1.68 (s, 4H), 1.22–1.40 (m, 6H), 1.27 (s, 12H), 0.86 (m, 3H).

In analogy to example 7.1, using the appropriate alcohols from example 5, the following compounds were synthesized:

7.2. (RS)-3-Phenyl-2-(5,5,8,8-tetramethyl-5,6,7,8-tetrahydronaphthalen-2-yl)-propanal, colorless oil, 1H NMR (CDCl$_3$): 9.73 (d, J=1.7 Hz, 1H), 7.10–7.30 (m, 4H), 7.06 (m, 2H), 6.97 (d, J=2.0 Hz, 1H), 6.92 (dd, J=8.1, 2.0 Hz, 1H), 3.78 (td, J=7.1, 1.7 Hz, 1H), 3.45 (dd, J=13.8, 7.1 Hz, 1H), 2.91 (dd, J=13.8, 7.1 Hz, 1H), 1.66 (s, 4H), 1.27 (s, 3H), 1.26 (s, 3H), 1.23 (s, 3H), 1.17 (s, 3H).

7.3. (RS)-3-(4-Chlorophenyl)-2-(5,5,8,8-tetramethyl-5,6,7,8-tetrahydronaphthalen-2-yl)-propanal, colorless oil, 1H NMR (CDCl$_3$): 9.73 (d, J=1.7 Hz, 1H), 7.28 (d, J=8.4 Hz, 1H), 7.17 (d, J=8.1 Hz, 2H), 6.95 (d, J=8.1 Hz, 2H), 6.92 (d, J=3.1 Hz, 1H), 6.88 (dd, J=8.4, 3.1 Hz, 1H), 3.73 (t, J=7.5 Hz, 1H), 3.41 (dd, J=14.4, 7.5 Hz, 1H), 2.89 (dd, J=14.4, 7.5 Hz, 1H), 1.66 (s, 4H), 1.27 (s, 6H), 1.23 (s, 3H), 1.17 (s, 3H).

7.4. (RS)-2-(5,5,8,8-Tetramethyl-5,6,7,8-tetrahydronaphthalen-2-yl)-3-(4-trifluoromethylphenyl)-propanal, yellow oil, 1H NMR (CDCl$_3$): 9.75 (s, 1H), 7.47 (d, J=8.4 Hz, 2H), 7.31 (d, J=7.8 Hz, 1H), 7.15 (d, J=8.4 Hz, 2H), 6.91 (m, 2H), 3.78 (t, J=7.8 Hz, 1H), 3.49 (dd, J=13.5, 7.8 Hz, 1H), 2.97 (dd, J=13.5, 7.8 Hz, 1H), 1.66 (s, 4H), 1.27 (s, 6H), 1.22 (s, 3H), 1.13 (s, 3H).

7.5. (RS)-4-Phenyl-2-(5,5,8,8-tetramethyl-5,6,7,8-tetrahydronaphthalen-2-yl)-butanal, colorless oil, 1H NMR (CDCl$_3$): 9.64 (d, J=1.9 Hz, 1H), 7.10–7.35 (m, 6H), 7.07 (d, J=2.4 Hz, 1H), 6.9 (dd, J=9.3, 2.4 Hz, 1H), 3.45 (td, J=7.2, 1.9 Hz, 1H), 2.58(m, 2H), 2.38 (m, 1H), 2.04 (m, 1H), 1.69 (s, 4H), 1.28 (s, 9H), 1.27 (s, 3H).

EXAMPLE 8

8.1. Preparation of (RS)-2-(5,5,8,8-tetramethyl-5,6,7,8-tetrahydronaphthalen-2-yl)-propanal 0.55 g of (RS)-N-methoxy-N-methyl 2-(5,5,8,8-tetramethyl-5,6,7,8-tetrahydronaphthalen-2-yl)-propanoic amide in 2 ml of THF was added to a solution of LiAlH$_4$ (2.1 ml of 1M solution in THF) in 7 ml of THF at −40° C. over 10 minutes. The reaction mixture was stirred at −40° C. for 30 minutes, then warmed to 15° C. over 1.5 hour. The mixture was cooled down to −40° C. and was added a 20% solution of KHSO$_4$ (5 ml) slowly over 15 minutes and then stirred at room temperature for 1 hour. The reaction mixture was poured into ethyl acetate (200 ml) and water (100 ml) was added. The phases were separated and the aqueous layer was extracted with ethyl acetate (3×25 ml). The combined organic extracts were washed with water (1×50 ml), 1N HCl (1×50 ml), sat. sodium bicarbonate (1×50 ml), brine (1×50 ml), dried over $MgSO_4$ and concentrated in vacuo. The residue was used in next step without column purification. Yield 96%. 1H NMR (CDCl3): 9.66 (d, J=1.5 Hz, 1H), 7.30 (d, J=8.1 Hz, 1H), 7.11 (d, J=2.0 Hz, 1H), 6.96 (dd, J=2.0, 8.0 Hz, 1H), 3.58 (qd, J=1.6, 7.1 Hz, 1H), 1.68 (s, 4H), 1.42 (d, J=7.1 Hz, 3H), 1.27 (s, 12H).

In analogy to example 8.1, using the appropriate amides from example 6, the following compounds were synthesized:

8.2. (RS)-2-(5,5,8,8-Tetramethyl-5,6,7,8-tetrahydronaphthalen-2-yl)-pentanal, 1H NMR ($CDCl_3$): 9.64 (d, J=2.3 Hz, 1H), 7.28 (d, J=8.1 Hz, 1H), 7.08 (d, J=1.9 Hz, 1H), 6.94 (dd, J=2.0, 8.0 Hz, 1H), 3.44 (dt, J=2.3, 8.0 Hz, 1H), 2.03 (m, 1H), 1.68 (m, 1H), 1.67 (s, 4H), 1.30 (m, 1H), 1.27 (s, 12H), 0.92 (t, J=7.3 Hz, 3H).

8.3. (RS)-(E)-2-(5,5,8,8-Tetramethyl-5,6,7,8-tetrahydronaphthalen-2-yl)-hex-4-enal, 1H NMR ($CDCl_3$): 9.64 (d, J=2.2 Hz, 1H), 7.28 (d, J=8.1 Hz, 1H), 7.08 (d, J=2.1 Hz, 1H), 6.94 (dd, J=2.0, 8.1 Hz, 1H), 5.40 (m, 2H), 3.49 (dt, J=2.1, 8.4 Hz, 1H), 2.74 (m, 1H), 2.42 (m, 1H), 1.67 (s, 4H), 1.61 (dd, J=1.2, 4.9 Hz, 3H), 1.27 (s, 6H), 1.26 (s, 6H).

8.4. (RS)-2-(5,5,8,8-Tetramethyl-5,6,7,8-tetrahydronaphthalen-2-yl)-hexanal, 1H NMR ($CDCl_3$): 9.63 (d, J=2.3 Hz, 1H), 7.28 (d, J=8.1 Hz, 1H), 7.08 (d, J=2.0 Hz, 1H), 6.94 (dd, J=2.0, 8.0 Hz, 1H), 3.42(dt, J=2.3, 7.3 Hz, 1H), 2.02 (m, 1H), 1.70 (m, 1H), 1.67 (s, 4H), 1.30 (m, 4H), 1.27 (s, 6H), 1.26 (s, 6H), 0.88 (t, J=7.2 Hz, 3H).

8.5. (RS)-2-(5,5,8,8-Tetramethyl-5,6,7,8-tetrahydronaphthalen-2-yl)-decanal, 1H NMR ($CDCl_3$): 9.63 (d, J=2.4 Hz, 1H), 7.28 (d, J=8.1 Hz, 1H), 7.08 (d, J=2.0 Hz, 1H), 6.94 (dd, J=2.0, 8.1 Hz, 1H), 3.43 (dt, J=2.3, 7.3 Hz, 1H), 2.05 (m, 1H), 1.70 (m, 1H), 1.68 (s, 4H), 1.27 (s, 6H), 1.26 (s, 6H), 1.23 (m, 10H), 0.86 (t, J=6.6 Hz, 3H).

8.6. (RS)-4-Methyl-2-(5,5,8,8-tetramethyl-5,6,7,8-tetrahydronaphthalen-2-yl)-pentanal, 1H NMR ($CDCl_3$): 9.62 (d, J=2.4 Hz, 1H), 7.28 (d, J=8.2 Hz, 1H), 7.09 (d, J=2.0 Hz, 1H), 6.95 (dd, J=2.0, 8.0 Hz, 1H), 3.53 (dt, J=2.4, 7.4 Hz, 1H), 1.91 (m, 1H), 1.67 (s, 4H), 1.54 (m, 2H), 1.27 (s, 12H), 0.92 (d, J=6.3 Hz, 3H), 0.92 (d, J=6.3 Hz, 3H).

8.7. (RS)-3-(4-Fluorophenyl)-2-(5,5,8,8-tetramethyl-5,6,7,8-tetrahydronaphthalen-2-yl)-propanal, 1H NMR ($CDCl_3$): 9.72 (d, J=1.5 Hz, 1H), 7.10–6.80 (m, 7H), 3.73 (td, J=7.2, 1.5 Hz, 1H), 3.40 (dd, J=14.0, 7.1 Hz, 1H), 2.88 (dd, J=14.0, 7.4 Hz, 1H), 1.66 (s, 4H), 1.27 (s, 3H), 1.26 (s, 3H), 1.23 (s, 3H), 1.17 (s, 3H).

8.8. (RS)-3-(3-Chlorophenyl)-2-(5,5,8,8-tetramethyl-5,6,7,8-tetrahydronaphthalen-2-yl)-propanal, 1H NMR ($CDCl_3$): 9.73 (d, J=1.2 Hz, 1H), 7.35–7.25 (m, 1H), 7.20–7.10 (m, 2H), 7.00–6.80 (m, 4H), 3.74 (td, J=7.8, 1.2 Hz, 1H), 3.39 (dd, J=13.9, 6.8 Hz, 1H), 2.87 (dd, J=13.9, 7.7 Hz, 1H), 1.66 (s, 4H), 1.27 (s, 3H), 1.26 (s, 3H), 1.23 (s, 3H), 1.16 (s, 3H).

8.9. (RS)-3-(4-Methoxyphenyl)-2-(5,5,8,8-tetramethyl-5,6,7,8-tetrahydronaphthalen-2-yl)-propanal, 1H NMR ($CDCl_3$): 9.72 (d, J=1.7 Hz, 1H), 7.27 (d, J=8.0 Hz, 2H), 7.05–6.85 (m, 3H), 6.76 (d, J=8.2 Hz, 2H), 3.76 (s, 3H), 3.74 (td, J=7.3, 1.8 Hz, 1H), 3.37 (dd, J=14.0, 7.5 Hz, 1H), 2.88 (dd, J=14.0, 7.0 Hz, 1H), 1.66 (s, 4H), 1.27 (s, 3H), 1.26 (s, 3H), 1.23 (s, 3H), 1.19 (s, 3H).

EXAMPLE 9

Preparation of (RS)-(E)-ethyl 4-[3-(5,5,8,8-tetramethyl-5,6,7,8-tetrahydronaphthalen-2-yl)-oct-1-enyl]-benzoate 724 mg of ethyl 4-(diethoxyphosphorylmethyl)-benzoate were dissolved in 10 ml of THF absolute and treated, at −20° C., with 2.4 ml of a 1.0M solution of lithium bis(trimethylsilyl)amide in hexane. After 15 minutes at −20° C., a solution of 483 mg of (RS)-2-(5,5,8,8-tetramethyl-5,6,7,8-tetrahydronaphthalen-2-yl)-heptanal in 5 ml THF absolute was added. The reaction mixture was stirred at room temperature for 1 hour. The mixture was quenched by the addition of 1 portion of 10 ml of water followed by 1 portion of 10 ml of a saturated aqueous ammonium chloride solution. The mixture was extracted with 3 portions of 10 ml of ethyl acetate. The combined organic extracts were dried over $MgSO_4$ and the solvent evaporated. The yellow oil was purified by flash chromatography ($SiO_2$, 2.5% ethyl acetate/hexanes) to yield 669 mg of a colorless oil, 1H NMR ($CDCl_3$): 7.95 (d, J=8.5 Hz, 2H), 7.39 (d, J=8.5 Hz, 2H), 7.24 (d, J=8.4 Hz, 1H), 7.13 (d, J=1.8 Hz, 1H), 7.01 (dd, J=8.4, 1.8 Hz, 2H), 6.43 (m, 2H), 4.35 (q, J=7.2 Hz, 2H), 3.36 (m, 1H), 1.78 (m, 2H), 1.67 (s, 4H), 1.38 (t, J=7.2 Hz, 3H), 1.20–1.42 (m, 6H), 1.28 (s, 9H), 1.26 (s, 3H), 0.86 (m, 3H).

In analogy to example 9.1, using the appropriate aldehydes from example 7 and 8 and the proper phosphonate, the following compounds were synthesized:

9.2 (RS)-(E)-Methyl-4-[3-(5,5,8,8-tetramethyl-5,6,7,8-tetrahydronaphthalen-2-yl)-but-1-enyl]-benzoate, 7.94 (d, J=8.3 Hz, 2H), 7.40 (d, J=8.3 Hz, 2H), 7.25 (d, J=8.1 Hz, 1H), 7.17 (d, J=1.9 Hz, 1H), 7.01 (dd, J=2.0, 8.1 Hz, 1H), 6.51 (dd, J=15.9, 6.0 Hz, 1H), 6.44 (d, J=15.9 Hz, 1H), 3.89 (s, 3H), 3.60 (m, 1H), 1.67 (s, 4H), 1.46 (d, J=7.0 Hz, 3H), 1.28 (s, 6H), 1.27 (s, 6H).

9.3 (RS)-(E)-Methyl-4-[3-(5,5,8,8-tetramethyl-5,6,7,8-tetrahydronaphthalen-2-yl)-hex-1-enyl]-benzoate, 1H NMR ($CDCl_3$): 7.94 (d, J=8.4 Hz, 2H), 7.38 (d, J=8.4 Hz, 2H), 7.23 (d, J=8.2 Hz, 1H), 7.13 (d, J=2.0 Hz, 1H), 6.99 (dd, J=2.0, 8.0 Hz, 1H), 6.44 (m, 2H), 3.89 (s, 3H), 3.36 (m, 1H), 1.73 (m, 2H), 1.67 (s, 4H), 1.29 (m, 2H), 1.27 (s, 6H), 1.26 (s, 6H), 0.92 (t, J=7.3 Hz, 3H).

9.4 (RS)-(E,E)-Methyl-4-[3-(5,5,8,8-tetramethyl-5,6,7,8-tetrahydronaphthalen-2-yl)-hepta-1,5-dienyl]-benzoate, 1H NMR ($CDCl_3$): 7.94 (d, J=8.4 Hz, 2H), 7.39 (d, J=8.4 Hz, 2H), 7.53 (d, J=8.1 Hz, 1H), 7.13 (d, J=2.0 Hz, 1H), 6.98 (dd, J=2.0, 8.1 Hz, 1H), 6.45 (m, 2H), 5.45 (m, 2H), 3.89 (s, 3H), 3.42 (q, J=7.2 Hz, 1H), 2.50 (m, 2H), 1.67 (s, 4H), 1.60 (m, 3H), 1.27 (s, 6H), 1.26 (s, 6H).

9.5 (RS)-(E)-Methyl-4-[3-(5,5,8,8-tetramethyl-5,6,7,8-tetrahydronaphthalen-2-yl)-hept-1-enyl]-benzoate, 1H NMR ($CDCl_3$): 7.94 (d, J=8.5 Hz, 2H), 7.39 (d, J=8.5 Hz, 2H), 7.23 (d, J=8.1 Hz, 1H), 7.13 (d, J=1.9 Hz, 1H), 6.99 (dd, J=1.9, 8.0 Hz, 1H), 6.43 (m, 2H), 3.89 (s, 3H), 3.35 (m, 1H), 1.77 (m, 2H), 1.67 (s, 4H), 1.29 (m, 4H), 1.27 (s, 6H), 1.26 (s, 6H), 0.88 (t, J=7.1 Hz, 3H).

9.6 (RS)-(E)-Methyl-4-[3-(5,5,8,8-tetramethyl-5,6,7,8-tetrahydronaphthalen-2-yl)-undec-1-enyl]-benzoate, 1H NMR ($CDCl_3$): 7.94 (d, J=8.5 Hz, 1H), 7.39 (d, J=8.5 Hz, 1H), 7.21 (d, J=8.1 Hz, 1H), 7.13 (d, J=1.9 Hz, 1H), 6.98 (dd, J=1.9, 8.1 Hz, 1H), 6.43 (m, 2H), 3.89 (s, 3H), 3.35 (m, 1H), 1.77 (m, 2H), 1.66 (s, 4H), 1.27 (s, 6H), 1.26 (s, 6H), 1.25 (m, 10H), 0.86 (t, J=6.6 Hz, 3H).

9.7 (RS)-(E)-Methyl-4-[5-methyl-3-(5,5,8,8-tetramethyl-5,6,7,8-tetrahydronaphthalen-2-yl)-hex-1-enyl]- benzoate, 1H NMR (CDCl$_3$): 7.93 (d, J=8.6 Hz, 2H), 7.38 (d, J=8.6 Hz, 2H), 7.23 (d, J=8.1 Hz, 1H), 7.14 (d, J=2.0 Hz, 1H), 6.99 (dd, J=2.0, 8.0 Hz, 1H), 6.42 (m, 2H), 3.89 (s, 3H), 3.43 (m, 1H), 1.66 (s, 4H), 1.65 (m, 1H), 1.56 (m, 2H), 1.27 (s, 6H), 1.26 (s, 6H), 0.93 (d, J=6.4 Hz, 3H), 0.89 (d, J=6.4 Hz, 3H).

9.8 (RS)-(E)-Ethyl-4-[4-phenyl-3-(5,5,8,8-tetramethyl-5,6,7,8-tetrahydronaphthalen-2-yl)-but-1-enyl]-benzoate, pale yellow oil, 1H NMR (CDCl$_3$): 7.91 (d, J=9.0 Hz, 2H), 7.34 (d, J=9.0 Hz, 2H), 7.00–7.30 (m, 8H), 6.53 (dd, J=16.2, 7.8 Hz, 1H), 6.30 (d, J=16.2 Hz, 1H), 4.35 (q, J=7.2 Hz, 2H), 3.68 (q, J=7.8 Hz, 1H), 3.10 (d, J=7.8 Hz, 2H), 1.66 (s, 4H), 1.38 (t, J=7.2 Hz, 3H), 1.27 (s, 6H), 1.25 (s, 3H), 1.19 (s, 3H).

9.9 (RS)-(E)-Ethyl-4-[4-(4-chlorophenyl)-3-(5,5,8,8-tetramethyl-5,6,7,8-tetrahydronaphthalen-2-yl)-but-1-enyl]-benzoate, colorless oil, 1H NMR (CDCl$_3$): 7.95 (d, J=8.4 Hz, 2H), 7.35 (d, J=8.4 Hz, 2H), 7.15–7.33 (m, 3H), 6.92–7.10 (m, 4H), 6.48 (dd, J=16.5, 7.5 Hz, 1H), 6.31 (d, J=16.5 Hz, 1H), 4.36 (q, J=7.2 Hz, 2H), 3.62 (q, J=7.5 Hz, 1H), 3.07 (d, J=7.5 Hz, 2H), 1.66 (s, 4H), 1.38 (t, J=7.2 Hz, 3H), 1.27 (s, 6H), 1.24 (s, 3H), 1.18 (s, 3H).

9.10 (RS)-(E)-Ethyl-4-[3-(5,5,8,8-tetramethyl-5,6,7,8-tetrahydronaphthalen-2-yl)-4-(4-trifluoromethylphenyl)-but-1-enyl]-benzoate, colorless oil, 1H NMR (CDCl$_3$): 7.96 (d, J=8.4 Hz, 2H), 7.46 (d, J=9.0 Hz, 2H), 7.35 (d, J=8.4 Hz, 2H), 7.25 (m, 1H), 7.14 (d, J=9.0 Hz, 2H), 6.90–7.05 (m, 2H), 6.51 (dd, J=16.2, 7.5 Hz, 1H), 6.35 (d, J=16.2 Hz, 1H), 4.35 (q, J=7.2 Hz, 2H), 3.66 (m, 1H), 3.13 (m, 2H), 1.66 (s, 4H), 1.38 (t, J=7.2 Hz, 3H), 1.26 (s, 6H), 1.22 (s, 3H), 1.13 (s, 3H).

9.11 (RS)-(E)-Ethyl-4-[5-phenyl-3-(5,5,8,8-tetramethyl-5,6,7,8-tetrahydronaphthalen-2-yl)-pent-1-enyl]-benzoate, pale yellow oil, 1H NMR (CDCl$_3$): 7.97 (d, J=8.4 Hz, 2H), 7.38 (d, J=8.4 Hz, 2H), 7.12–7.35 (m, 7H), 7.02 (dd, J=8.5, 1.3 Hz, 1H), 6.44 (m, 2H), 4.37 (q, J=7.2 Hz, 2H), 3.40 (m, 1H), 2.63 (m, 2H), 2.13 (q, J=7.8 Hz, 2H), 1.68 (s, 4H), 1.38 (t, J=7.2 Hz, 3H), 1.29 (s, 3H), 1.27 (s, 9H).

9.12 (RS)-(E)-Ethyl-5-[3-(5,5,8,8,-tetramethyl-5,6,7,8-tetrahydronaphthalen-2-yl)-oct-1-enyl]-thiophene-2-carboxylate, colorless oil, 1H NMR(CDCl$_3$): 7.62 (d, J=4.5 Hz, 1H), 7.23 (d, J=8.4 Hz, 1H), 7.11 (d, J=3.0 Hz, 1H), 6.96 (dd, J=8.5, 3.0 Hz, 1H), 6.85 (d, J=4.5 Hz, 1H), 6.48 (d, J=16.2 Hz, 1H), 6.32 (dd, J=16.2, 8.4 Hz, 1H), 3.86 (s, 3H), 3.31 (q, J=8.3 Hz, 1H), 1.70–1.90 (m, 2H), 1.67 (s, 4H), 1.20–1.45 (m, 6H), 1.27 (s, 9H), 1.26 (s, 3H), 0.86 (m, 3H).

9.13 (RS)-(E)-Methyl-4-[4-(4-fluorophenyl)-3-(5,5,8,8-tetramethyl-5,6,7,8-tetrahydronaphthalen-2-yl)-but-1-enyl]-benzoate, 1H NMR (CDCl$_3$): 7.94 (d, J=8.4 Hz, 2H), 7.34 (d, J=8.5 Hz, 2H), 7.24 (d, J=8.7 Hz, 2H), 7.05–6.95 (m, 3H), 6.89 (t, J=8.7 Hz, 2H), 6.50 (dd, J=15.9, 7.7 Hz, 1H), 6.29 (d, J=15.8 Hz, 1H), 3.89 (s, 3H), 3.62 (q, J=7.9 Hz, 1H), 3.05 (d, J=7.9 Hz, 2H), 1.66 (s, 4H), 1.27 (s, 3H), 1.26 (s, 3H), 1.24 (s, 3H), 1.18 (s, 3H).

9.14 (RS)-(E)-Methyl-4-[4-(3-chlororophenyl)-3-(5,5,8,8-tetramethyl-5,6,7,8-tetrahydronaphthalen-2-yl)-but-1-enyl]-benzoate, 1H NMR (CDCl$_3$): 7.94 (d, J=8.4 Hz, 2H), 7.35 (d, J=8.4 Hz, 2H), 7.25–6.90 (m, 7H), 6.51 (dd, J=15.8, 7.6 Hz, 1H), 6.35 (d, J=15.8 Hz, 1H), 3.90 (s, 3H), 3.65 (m, 1H), 3.06 (m, 2H), 1.66 (s, 4H), 1.27 (s, 3H), 1.26 (s, 3H), 1.24 (s, 3H), 1.17 (s, 3H).

9.15 (RS)-(E)-Methyl-4-[4-(4-methoxyphenyl)-3-(5,5,8,8-tetramethyl)-5,6,7,8-tetrahydronaphthalen-2-yl)-but-1-enyl]-benzoate, 1H NMR (CDCl$_3$): 7.93 (d, J=8.4 Hz, 2H), 7.34 (d, J=8.3 Hz, 2H), 7.24 (d, J=8.1 Hz, 1H), 7.05–7.00 (m, 2H), 6.98 (d, J=8.8 Hz, 2H), 6.76 (d, J=8.7 Hz, 2H), 6.50 (dd, J=15.9, 7.8 Hz, 1H), 6.29 (d, J=15.9 Hz, 1H), 3.89 (s, 3H), 3.76 (s, 3H), 3.62 (q, J=7.6 Hz, 1H), 3.03 (d, J=7.5 Hz, 2H), 1.66 (s, 4H), 1.27 (s, 3H), 1.26 (s, 3H), 1.25 (s, 3H), 1.20 (s, 3H).

9.16 (RS)-(E)-Methyl-3-fluoro-4-[3-(5,5,8,8-tetramethyl-5,6,7,8-tetrahydronaphthalen-2-yl)-oct-1-enyl]-benzoate, 1H NMR (CDCl$_3$): 7.73 (dd, J=8.1, 1.7 Hz, 1H), 7.67 (dd, J=11.1, 1.6 Hz, 1H), 7.48 (t, J=7.8 Hz, 1H), 7.24 (d, J=8.1 Hz, 1H), 7.13 (d, J=2.0 Hz, 1H), 6.99 (dd, J=8.1, 2.0 Hz, 1H), 6.59 (d, J=16.0 Hz, 1H), 6.51 (dd, J=16.0, 7.4 Hz, 1H), 3.90 (s, 3H), 3.37 (q, J=8.3 Hz, 1H), 1.77 (m, 2H), 1.67 (s, 4H), 1.28 (s, 6H), 1.26 (s, 6H), 1.40–1.20 (m, 6H), 0.86 (t, J=6.8 Hz, 3H).

EXAMPLE 10

10.1. Preparation of (RS)-(E)-4-[3-(5,5,8,8-tetramethyl-5,6,7,8-tetrahydronaphthalen-2-yl)-oct-1-enyl]-benzoic Acid 647 mg of (RS)-(E)-ethyl-4-[3-(5,5,8,8-tetramethyl-5,6,7,8-tetrahydronaphthalen-2-yl)-oct-1-enyl]-benzoate were dissolved in 9 ml of ethanol absolute and treated with 1.63 g of potassium hydroxide in 5 ml of water. To the mixture was added 5 ml of THF and the resulting clear solution was heated to 45° C. for 1 hour. The reaction mixture was diluted with 20 ml of water and the pH was adjusted to 2 with HCl 25%. The mixture was extracted with 3 portions of 25 ml of ethyl acetate. The combined organic extracts were washed with 1 portion of 25 ml of water and 1 portion of 25 ml of a saturated aqueous NaCl solution. The organic phase was dried over MgSO$_4$ and concentrated in vacuo to give a pale yellow oil. Trituration in pentane gave 588 mg of a pale yellow solid, m.p. 108–109° C.

In analogy to example 10.1. using the appropriate esters from example 9, the following compounds were synthesized:

10.2. (RS)-(E)-4-[3-(5,5,8,8-Tetramethyl-5,6,7,8-tetrahydronaphthalen-2-yl)-but-1-enyl]-benzoic acid, m.p. 203–204° C.

10.3. (RS)-(E)-4-[3-(5,5,8,8-Tetramethyl-5,6,7,8-tetrahydronaphthalen-2-yl)-hex-1-enyl]-benzoic acid, m.p. 116–118° C.

10.4. (RS)-(E)-4-[3-(5,5,8,8-Tetramethyl-5,6,7,8-tetrahydronaphthalen-2-yl)-hepta-1,5-dienyl]-benzoic acid, m.p. 145–147° C.

10.5. (RS)-(E)-4-[3-(5,5,8,8-Tetramethyl-5,6,7,8-tetrahydronaphthalen-2-yl)-hept-1-enyl]-benzoic acid, m.p. 107–108° C.

10.6. (RS)-(E)-4-[3-(5,5,8,8-Tetramethyl-5,6,7,8-tetrahydronaphthalen-2-yl)-undec-1-enyl]-benzoic acid, viscous oil, 1H NMR (DMSO-d6):12.84 (s, 1H), 7.85 (d, J=8.4 Hz, 1H), 7.51 (d, J=8.4 Hz, 1H), 7.23 (d, J=8.2 Hz, 1H), 7.18 (d, J=1.7 Hz, 1H), 7.02 (dd, J=1.7, 8.2 Hz, 1H), 6.60 (dd, J=15.9, 8.2 Hz, 1H), 6.48 (d, J=15.9 Hz, 1H), 3.37 (q, J=7.7 Hz, 1H), 1.70 (m, 2H), 1.61 (s, 4H), 1.22 (s, 6H), 1.20 (s, 6H), 1.15 (m, 10H), 0.82 (t, J=6.5 Hz, 3H).

10.7. (RS)-(E)-4-[5-Methyl-3-(5,5,8,8-tetramethyl-5,6,7,8-tetrahydronaphthalen-2-yl)-hex-1-enyl]-benzoic acid, m.p. 61–78° C. 1H NMR (DMSO-d6): 12.81 (s, 1H), 7.85 (d, J=8.4 Hz, 2H), 7.50 (d, J=8.4 Hz, 2H), 7.24 (d, J=8.2 Hz, 1H), 7.20 (d, J=1.8 Hz, 1H), 7.03 (dd, J=1.8, 8.2 Hz, 1H), 6.58 (dd, J=15.9, 7.8 Hz, 1H), 6.49 (d, J=15.9 Hz, 1H), 3.47 (q, J=7.6 Hz, 1H), 1.62 (s, 4H), 1.60 (m, 2H), 1.43 (m, 1H), 1.23 (s, 6H), 1.21 (s, 6H), 0.90 (d, J=6.4 Hz, 3H), 0.88 (d, J=6.4 Hz, 3H).

10.8. (RS)-(E)-4-[4-Phenyl-3-(5,5,8,8-tetramethyl-5,6,7,8-tetrahydronaphthalen-2-yl)-but-1-enyl]-benzoic acid, pale yellow solid, m.p. 183–184° C.

10.9. (RS)-(E)-4-[4-(4-Chlorophenyl)-3-(5,5,8,8-tetramethyl-5,6,7,8-tetrahydronaphthalen-2-yl)-but-1-enyl]-benzoic acid, white solid, m.p. 168–169° C.

10.10. (RS)-(E)-4-[3-(5,5,8,8-Tetramethyl-5,6,7,8-tetrahydronapthalen-2-yl)-4-(4-trifluoromethylphenyl)-but-1-enyl]-benzoic acid, white solid, m.p. 188–189° C.

10.11. (RS)-(E)-4-[5-Phenyl-3-(5,5,8,8-tetramethyl-5,6,7,8-tetrahydronaphthalen-2-yl)-pent-1-enyl]-benzoic acid, pale yellow solid, m.p. 78–79° C.

10.12. (RS)-(E)-5-[3-(5,5,8,8-Tetramethyl-5,6,7,8-tetrahydronaphthalen-2-yl)-oct-1-enyl]-thiophene-2-carboxylic acid, white solid, m.p. 128–129° C.

10.13. (RS)-(E)-4-[4-(4-Fluorophenyl)-3-(5,5,8,8-tetramethyl-5,6,7,8-tetrahydronaphthalen-2-yl)-but-1-enyl]-benzoic acid, white solid, m.p. 168–169° C.

10.14. (RS)-(E)-4-[4-(3-Chlororophenyl)-3-(5,5,8,8-tetramethyl-5,6,7,8-tetrahydronaphthalen-2-yl)-but-1-enyl]-benzoic acid, white solid, m.p. 166–169° C.

10.15. (RS)-(E)-4-[4-(4-Methoxyphenyl)-3-(5,5,8,8-tetramethyl-5,6,7,8-tetrahydronaphthalen-2-yl)-but-1-enyl]-benzoic acid, white solid, m.p. 170–175° C.

10.16. (RS)-(E)-3-Fluoro-4-[3-(5,5,8,8-tetramethyl-5,6,7,8-tetrahydronaphthalen-2-yl)-oct-1-enyl]-benzoic acid, white solid, m.p. 112–113° C.

EXAMPLE 11

11.1. Preparation of (RS)-4-[2-(5,5,8,8-tetramethyl-5,6,7,8-tetrahydronaphthalen-2-yl)-heptyloxy]-benzoic Acid 400 mg of (RS)-2-(5,5,8,8-tetramethyl-5,6,7,8-tetrahydronaphthalen-2-yl)-heptanol dissolved in 25 ml of THF absolute were treated with 382 mg of triphenylphosphine, 242 mg of ethyl 4-hydroxybenzoate and 0.24 ml of diethyl azodicarboxylate. The reaction mixture was heated to reflux for 6 hours. The mixture was diluted with 1 portion of 50 ml of diethylether and washed with 2 portions of 25 ml of water and 1 portion of 50 ml of a saturated aqueous sodium chloride solution. The organic phase was dried over $MgSO_4$ and concentrated in vacuo. The resulting yellow oil was purified by flash chromatography ($SiO_2$, 3% ethyl acetate/hexanes), giving 591 mg of (RS)-ethyl 4-[2-(5,5,8,8-tetramethyl-5,6,7,8-tetrahydronaphthalen-2-yl)-heptyloxy]-benzoate as a colorless oil.

The ester (591 mg) was dissolved in 8 ml of ethanol absolute and treated with 1.47 g of potassium hydroxide in 5 ml water. To the heterogeneous mixture was added 4 ml of THF. The resulting clear solution was heated to 45° C. for 3 hours. The reaction mixture was diluted with 20 ml of water and the pH was adjusted to 2 with HCl 25%. The mixture was extracted with 3 portions of 20 ml of ethyl acetate. The combined extracts were dried over $MgSO_4$ and concentrated in vacuo, giving a yellow oil. The crude product was purified by flash chromatography ($SiO_2$, 25% ethyl acetate/hexanes), yielding 466 mg of a pale yellow solid of very low melting point, microanalysis, calc.: C 79.58%, H 9.06%;
found: C 79.50%, H 9.05%.

In analogy to example 11.1, using 2-(5,5,8,8-tetramethyl-5,6,7,8-tetrahydronaphthalen-2-yl)-ethanol (Example 5.6.) the following compound was synthesized:

11.2. 4-[2-(5,5,8,8-Tetramethyl-5,6,7,8-tetrahydronaphthalen-2-yl)-ethyloxy]-benzoic acid, white solid, m.p. 195–196° C.

In analogy to example 11.1, using methyl 4-mercaptobenzoate, the following compound was synthesized:

11.3. (RS)-4-[2-(5,5,8,8-Tetramethyl-5,6,7,8-tetrahydronaphthalen-2-yl)-heptyl-sulfanyl]-benzoic acid, as a yellow solid of low melting point, microanalysis,
calc: C 76.67%, H 8,83%;
found: C 76.79%, H 8.80%.

EXAMPLE 12

Preparation of (RS)-4-[3-(5,5,8,8-tetramethyl-5,6,7,8-tetrahydronaphthalen-2-yl)-oct-1-ynyl]-benzoic Acid 1.62 g of carbon tetrabromide were dissolved in 25 ml of methylene chloride and treated, at −20° C., with a solution of 2.56 g of triphenylphosphine in 25 ml of methylene chloride. The mixture was stirred at 0° C. for 15 minutes. To the orange solution were added 733 mg of (RS)-2-(5,5,8,8-tetramethyl-5,6,7,8-tetrahydronaphthalen-2-yl)-heptanal in 4 ml of methylene chloride, at 0° C. The reaction mixture was stirred at room temperature for 4 hours. The mixture was quenched with the addition of 50 ml of water followed by 6 ml of a saturated aqueous sodium bicarbonate solution. The phases were separated and the aqueous phase was further extracted with 2 portions of 25 ml of methylene chloride. The combined organic extracts were dried over $MgSO_4$ and concentrated in vacuo, giving a yellow solid. The residue was triturated in pentane and the solid was removed by filtration. The filtrate was concentrated in vacuo, yielding a yellow oil which was purified by flash chromatography ($SiO_2$, hexane), giving 1.03 g of (RS)-1,1-dibromo-3-(5,5,8,8-tetramethyl-5,6,7,8-tetrahydronaphthalen-2-yl)-oct-1-ene, as a colorless oil.

The dibromide (1.03 g) was dissolved in 17 ml of THF absolute and cooled to −78° C. The solution was treated with 3.0 ml of a 1.6M solution of butyl lithium in hexane. The reaction mixture was stirred at −78° C. for 1 hour then at room temperature for 2 hours. The mixture was quenched by the addition of 10 ml of water followed by 10 ml of a saturated aqueous ammonium chloride solution. The mixture was extracted with 3 portions of 20 ml of diethylether. Combined organic extracts were dried over $MgSO_4$ and concentrated in vacuo. The resulting yellow oil was purified by flash chromatography ($SiO_2$, hexanes), yielding 591 mg of (RS)-3-(5,5,8,8-tetramethyl-5,6,7,8-tetrahydronaphthalen-2-yl)-oct-1-yne as a colorless oil.

653 mg of methyl 4-iodobenzoate were dissolved in 15 ml of dimethylformamide absolute and treated successively with 1.4 ml of triethylamine, 70 mg of dichloro-bis (triphenylphosphine)palladium and 38 mg of cuprous iodide. The solution was twice evacuated and ventilated with argon then the alkyne (591 mg) in 4 ml of dimethylformamide absolute was added. The reaction mixture was stirred at room temperature for 4 hours then diluted with 50 ml of water. The mixture was extracted with 3 portions of 30 ml of diethylether. The combined organic extracts were washed with 2 portions of 20 ml of HCl 1N, 1 portion of 20 ml of water and 1 portion of 20 ml of a saturated aqueous sodium chloride solution. The organic phase was dried over $MgSO_4$ and concentrated in vacuo. The resulting brown oil was purified by flash chromatography ($SiO_2$, 5% tertbutylmethyl ether/hexanes), yielding 609 mg of (RS)-methyl-4-[3-(5,5,8,8-tetramethyl-5,6,7,8-tetrahydronaphthalen-2-yl)-oct-1-ynyl]-benzoate as a pale yellow oil.

The ester (609 mg) was dissolved in 9 ml of ethanol and treated with 1.59 g of potassium hydroxide in 6 ml of water. The heterogeneous mixture was further treated with 4 ml of THF and the resulting clear solution was heated to 45° C. for 1.5 hour. The mixture was diluted with 20 ml of water and the pH was adjusted to 2 with HCl 25%. The mixture was extracted with 3 portions of 25 ml of ethyl acetate. The combined organic extracts were dried over $MgSO_4$ and concentrated in vacuo. The resulting orange oil was purified by flash chromatography ($SiO_2$, 25% ethyl/hexanes) followed by trituration in pentane, giving 290 mg of (RS)-4-[3-(5,5,8,8-tetramethyl-5,6,7,8-tetrahydronaphthalen-2-yl)-oct-1-ynyl]-benzoic acid as a white solid, m.p. 115–116° C.

EXAMPLE 13
Preparation of 2-(1,1,3,3-tetramethyl-indan-5-yl)-acetic Acid 10.0 g of 1,1,3,3,5-pentamethylindane were dissolved in 125 ml of carbontetrachloride and were added to the resulting solution, 9.92 g of N-bromosuccinimide and 35 mg of 2,2'-azobisisobutyronitrile (AIBN). The reaction mixture was heated to reflux for 5 hours. The reaction was cooled to 0° C. and the succinimide was filtered off. The resulting solution was concentrated in vacuo and the residue (14.7 g) was further dissolved in 150 ml of hexane. The precipitate was again removed by filtration and the solution was concentrated in vacuo, giving 13.8 g of 5-bromomethyl-1,1,3,3-tetramethylindane as a yellow oil.

The bromide (13.8 g) was dissolved in 120 ml of acetonitrile and 0.4 g of 18-crown-ether-6 was added, followed by 6.73 g of pulverized potassium cyanide. The reaction mixture was heated to 50° C. for 2 hours. The mixture was cooled to 0° C. and filtered. The solution was concentrated in vacuo. The solid residue was treated with a solution of sodium hypochlorite to destroy the excess cyanide. After concentration in vacuo, 12.05 g of a yellow oil was obtained. The product was purified by flash chromatography ($SiO_2$, 10% ethyl acetate/hexanes), giving 7.99 g of 2-(1,1,3,3-tetramethylindan)-acetonitrile as a light yellow oil.

Potassium hydroxide (6.5 g) was dissolved in 30 ml of ethanol 95% and added to the nitrile (3.5 g). The mixture was heated to reflux for 6 hours under a stream of argon to remove the ammonia formed. The reaction mixture was cooled and concentrated in vacuo. The residue was taken up in 100 ml water and washed with 3 portions of 50 ml of ether, which were discarded. The aqueous phase was acidified to pH 2 with HCl 25% and extracted with 3 portions of 100 ml ether. The combined organic phases were dried with $MgSO_4$, filtered and concentrated in vacuo, yielding 3.64 g of 2-(1,1,3,3-tetramethylindan-5-yl)-acetic acid as a pale yellow solid, m.p. 143° C.

EXAMPLE 14
Preparation of (RS)-4-[2-(1,1,3,3-tetramethylindan-5-yl)-heptanoyloxy]-benzoic Acid The product was prepared as described in example 1, 2 and 3, using the product of example 13, yielding (RS)-4-[2-(1,1,3,3-tetramethylindan-5-yl)-heptanoyloxy]-benzoic as a colorless solid, m.p. 132–134° C.

EXAMPLE 15
15.1. Preparation of (RS)-4-[butoxy-(5,5,8,8-tetramethyl-5,6,7,8-tetrahydro-naphthalen-2-yl)-acetoxy]-benzoic Acid a) Preparation of oxo-(5,5,8,8-tetramethyl-5,6,7,8-tetrahydro-naphthalen-2-yl)-acetic Acid Ethyl Ester 12.4 g of aluminum trichloride were suspended in 40 ml of methylene chloride, cooled to 0° C. and treated dropwise with a mixture of 10 g of 1,1,4,4-tetramethyl-1,2,3,4-tetrahydronaphthalene and 8.3 g of ethyl oxalyl chloride, dissolved in 40 ml of methylene chloride. The reaction mixture was stirred at 0° C. for 15 minutes and at room temperature for 4 hours, then poured on ice water, acidified with 10 ml of 25% hydrochloric acid and extracted with methylene chloride. The organic phase was washed with water, dried ($Na_2SO_4$) and the solvent evaporated to give a yellow oil which was purified by filtration through a short column of silica gel (eluent hexane/ethyl acetate 10%) to afford 15 g of a yellow oil.

$^1$H NMR ($CDCl_3$): §1.30 (s, 12H), 1.42 (t, 3H, J=7.1 Hz), 1.71 (s, 4H), 4.45 (qu, 2H, J=7.1 Hz), 7.43 (d, 1H, J=8.30 Hz), 7.71 (dd, 1H, J=8.30 Hz, 1.95 Hz), 7.98 (d, 1H, J=1.95 Hz)

b) Preparation of (RS)-butoxy-(5,5,8,8-tetramethyl-5,6,7,8-tetrahydro-naphthalen-2-yl)-acetic Acid Ethyl Ester 6 g of oxo-(5,5,8,8-tetramethyl-5,6,7,8-tetrahydro-naphthalen-2-yl)-acetic acid ethyl ester and 2.6 g of butoxytrimethylsilane were dissolved in 200 ml of methylene chloride. The solution was cooled to 0° C., treated with 400 mg of trimethylsilyl triflate and stirred at 0° C. for 1.5 hours. After the dropwise addition of 2 g of triethylsilane, the reaction mixture was stirred at room temperature for 26 hours, then diluted with 500 ml of water, acidified with 2N hydrochloric acid and extracted with ether. The organic phase was washed with water, dried ($Na_2SO_4$) and the solvent evaporated. The oily residue was purified with flash chromatography (silica gel, eluent hexane/tert.butyl methyl ether 3%) and preparative HPLC (YMC CN 60 Å5–15 µm, hexane) to give 3.5 g of the title product as colorless oil.

$^1$H NMR ($CDCl_3$): §0.91 (t, 3H, J=7.6 Hz), 1.23 (t, 3H, J=8.7 Hz), 1.26 (s, 12H), 1.38 (st, 2H, J=8.7 HZ), 1.55–1.66 (m, 6H), 3.44 (m, 1H), 3.54 (m, 1H), 4.18 (m, 2H), 4.79 (s, 1H), 7.19 (dd, 1H, J=8.3 Hz, 2 Hz), 7.26 (d, 1H, J=8.3 HZ), 7.35 (d, 1H, J=2 Hz)

c) (RS)-Butoxy-(5,5,8,8-tetramethyl-5,6,7,8-tetrahydro-naphthalen-2-yl)-acetic Acid 7.2 g of the ethyl ester of example 15.1b were dissolved in 100 ml of ethanol. A solution of 5.7 g of potassium hydroxide in 20 ml of water was added and the reaction mixture stirred at room temperature for 4 hours. The alkaline solution was poured on ice water, acidified with phosphoric acid and extracted with ethyl acetate. The organic phase was washed with water, dried ($Na_2SO_4$) and the solvent evaporated. The oily residue was filtered through a short pad of silica gel (eluent hexane/25% ethyl acetate) to give 6.1 g of a colorless oil which crystallized on standing in the cold. Recrystallisation from hexane gave the title compound as white crystals, m.p. 79–82° C.

d) (RS)-4-[Butoxy-(5,5,8,8-tetramethyl-5,6,7,8-tetrahydro-naphthalen-2-yl)-acetoxy]-benzoic Acid 3.5 g of the carboxylic acid from example 15.1.c were dissolved in 70 ml of methylene chloride, followed by the addition of 2.5 g of 4-hydroxy-benzoic acid benzyl ester and 134 mg of 4-dimethylamino-pyridine. The solution was cooled to 0° C. and treated dropwise with a solution of 2.3 g of dicyclohexylcarbodiimide in 30 ml of methylene chloride. The reaction mixture was stirred at room temperature for 6 hours, then poured on ice water and extracted with ethyl acetate. The organic phase was washed with water, dried ($Na_2SO_4$) and the solvent evaporated. The semi-crystalline residue was diluted with ether, stirred at 0° C. for 30 minutes and filtered. The filtrate was evaporated and the oily residue was purified with flash chromatography (silica gel, eluent hexane/ethyl acetate=4:1) to afford 6 g of (RS)-4-[butoxy-(5,5,8,8-tetramethyl-5,6,7,8-tetrahydronaphthalen-2-yl)-acetoxy]-benzoic acid benzyl ester as colorless oil. 6.4 g of this benzyl ester were dissolved in 150 ml of ethyl acetate, treated with 1.2 g of 10% Pd—C and hydrogenated at normal pressure/room temperature. After 45 minutes of vigorous stirring the theoretical amount of hydrogen has been absorbed; the catalyst was filtered off, the filtrate evaporated and the crystalline residue recrystallized from ethyl acetate/hexane to give 4 g of the title compound in white crystals, m.p. 129–130° C.

In analogy to examples 15.1. b) and c), by using different silyl ethers as starting material, the following compounds were synthesized:

- 15.2. b) and c) starting with methoxytrimethylsilane was obtained (RS)-methoxy-(5,5,8,8-tetramethyl-5,6,7,8-tetrahydro-naphthalen-2-yl)-acetic acid, m.p. 135–136° C. (hexane/ethyl acetate).
- 15.3. b) and c) starting with ethoxytrimethylsilane was obtained (RS)-ethoxy-(5,5,8,8-tetramethyl-5,6,7,8-tetrahydro-naphthalen-2-yl)-acetic acid, m.p. 106–109° C.
- 15.4. b) and c) starting with propoxytrimethylsilane was obtained (RS)-propoxy-(5,5,8,8-tetramethyl-5,6,7,8-tetrahydro-naphthalen-2-yl)-acetic acid, m.p. 84–86° C.

In analogy to examples 15.1. d), by using the appropriate acids from example 15, the following final products were synthesized:

- 15.2. d) (RS)-4-[methoxy-(5,5,8,8-tetramethyl-5,6,7,8-tetrahydro-naphthalen-2-yl)-acetoxy]-benzoic acid, m.p. 190–195° C. (ethyl acetate/hexane)
- 15.3. d) (RS)-4-[ethoxy-(5,5,8,8-tetramethyl-5,6,7,8-tetrahydro-naphthalen-2-yl)-acetoxy]-benzoic acid, m.p. 123–125° C. (acetonitril)
- 15.4. d) (RS)-4-[propoxy-(5,5,8,8-tetramethyl-5,6,7,8-tetrahydro-naphthalen-2-yl)-acetoxy]-benzoic acid, m.p. 155–156° C.

EXAMPLE 16

Preparation of (R)- and (S)-4-[butoxy-(5,5,8,8-tetramethyl-5,6,7,8-tetrahydro-naphthalen-2-yl)-acetoxy]-benzoic Acid

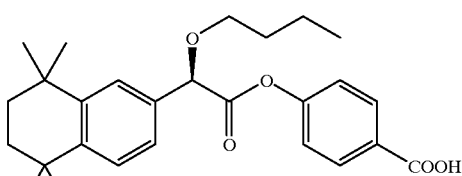

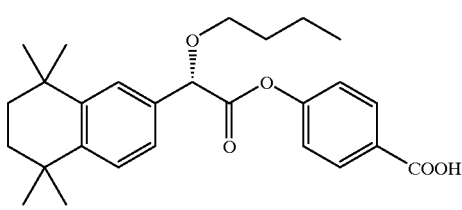

In analogy to example 15.1.d), 1.8 g of (RS)-butoxy-(5,5,8,8-tetramethyl-5,6,7,8-tetrahydro-naphthalen-2-yl)-acetic acid and 736 mg of D-pantolactone were coupled using 1.16 g of dicyclohexylcarbodiimide and 70 mg of 4-dimethylamino pyridine in 40 ml of methylene chloride. The crude product was purified with flash chromatography (silica gel, eluent hexane/ethyl acetate=4:1) to give 2.26 g of a colorless oil. The diastereomers were separated by preparative HPLC (Kromasil 100–10 CHI-DMB, hexane/tert.butylmethyl ether 0.5%) to give 0.99 g of one diastereomer I ($[\alpha]_{546}^{20}$=−3.49) and 1.0 g of the other diastereomer II ($[\alpha]_{546}^{20}$=+59.29).

711 mg of diastereomer I were dissolved in 30 ml of a 2:1 mixture of tetrahydrofuran and water and treated with 276 mg of lithium hydroxide monohydrate. The solution was stirred at room temperature for 7 hours, then poured on ice water, acidified with 0.5N hydrochloric acid and extracted with ethyl acetate. The organic phase was washed with water, dried ($Na_2SO_4$) and the solvent evaporated. The oily residue was filtered through a short pad of silica gel (eluent hexane/ethyl acetate=1:1) to give 616 mg of (R)- or (S)-butoxy-(5,5,8,8-tetramethyl-5,6,7,8-tetrahydro-naphthalen-2-yl)-acetic acid as a colorless oil, ($[\alpha]_{546}^{20}$=−76.95). 680 mg of this acid were coupled with 4-hydroxy-benzoic acid benzyl ester in analogy to example 4 to give after HPLC (eluent hexane/5% ethyl acetate) 700 mg of (R)- or (S)-4-[butoxy-(5,5,8,8-tetramethyl-5,6,7,8-tetrahydro-naphthalen-2-yl)-acetoxy]-benzoic acid benzyl ester as a colorless oil, ($[\alpha]_{546}^{20}$=−76.08).

685 mg of this benzyl ester were dissolved in 15 ml of ethyl acetate and, after the addition of 135 mg of Pd—C 10%, hydrogenated at normal pressure for 0.5 hours. The catalyst was filtered off, the filtrate evaporated and the residue recrystallized from ethyl acetate/hexane to give 444 mg of (R)- or (S)-4-[butoxy-(5,5,8,8-tetramethyl-5,6,7,8-tetrahydro-naphthalen-2-yl)-acetoxy]-benzoic acid as white crystals, m.p. 112–113° C., ($[\alpha]_{546}^{20}$=−92.55).

Treatment of the diastereomer II in the same way as described above yielded 581 mg of (S)- or (R)-4-[butoxy-(5,5,8,8-tetramethyl-5,6,7,8-tetrahydro-naphthalen-2-yl)-acetoxy]-benzoic acid as white crystals, m.p. 113–114° C., ($[\alpha]_{546}^{20}$=+88.39).

EXAMPLE 17

Preparation of (RS)-4-[3-butoxy-3-(5,5,8,8-tetramethyl-5,6,7,8-tetrahydro-naphthalen-2-yl)-propenyl]-benzoic Acid a) 3.4 g of (RS)-butoxy-(5,5,8,8-tetramethyl-5,6,7,8-tetrahydro-naphthalen-2-yl)-acetic acid ethyl ester were dissolved in 40 ml of ether. After the dropwise addition of 30 ml of a 1M solution of DIBAH in hexane at −78° C., the reaction mixture was warmed to 0° C. and stirred at this temperature for 1.5 hours. For work up, the solution was cooled to −10° C., carefully treated with 1 ml of a 2 molar solution of Rochelle salt in water followed by addition of further 7 ml of this reagent. The resulting white suspension was stirred at room temperature for 1.5 hours, filtered, the residue washed well with ether and the combined organic solution dried ($MgSO_4$) and the solvent evaporated to give 3.05 g of (RS)-2-butoxy-2-(5,5,8,8-tetramethyl-5,6,7,8-tetrahydro-naphthalen-2-yl)-ethanol as colorless oil. It was used in the next step without further purification.

b) 2 ml of oxalyl chloride were dissolved in 50 ml of methylene chloride and carefully treated with a solution of 3.4 ml of DMSO in 10 ml of methylene chloride at −60° C. The reaction mixture was warmed to −35° C. for 10 minutes, cooled to −60° C. and treated dropwise with a solution of 3.05 g of the above mentioned alcohol in 10 ml of methylene chloride. After stirring at −50° C. for 15 minutes, 7 ml of triethylamine were added dropwise. The reaction mixture was warmed to room temperature and stirred at this temperature for 2.5 hours. The resulting white suspension was poured on ice water, extracted with methylene chloride, the organic phase washed with water, dried ($MgSO_4$) and the solvent evaporated. Flash chromatography of the oily residue (silica gel, eluent hexane/5% ethyl acetate) yielded 1.8 g of (RS)-butoxy-(5,5,8,8-tetramethyl-5,6,7,8-tetrahydro-naphthalen-2-yl)-acetaldehyde as a slightly yellow oil.

c) 3 g of diethyl (4-carbethoxybenzyl)phosphonate were dissolved in 30 ml of tetra-hydrofuran, cooled to −20° C. and treated dropwise with 9.25 ml of a 1M solution of lithium bis(trimethylsilyl)amide in hexane. After 15 minutes, a solution of 1.8 g of the above mentioned aldehyde in 10 ml of tetrahydrofuran was added dropwise. The reaction mixture was warmed to room temperature, stirred for 3 hours, then poured on ice water, saturated ammonium chloride solution and extracted with ethyl acetate. The organic solution was washed with water, dried ($MgSO_4$) and the solvent evaporated. Flash chromatography of the resulting orange oil (silica gel, eluent hexane/5% ethyl acetate) afforded 1.6 g of (RS)-4-[3-butoxy-3-(5,5,8,8-tetramethyl-5,6,7,8-tetrahydro-naphthalen-2-yl)-propenyl]-benzoic acid ethyl ester as slightly yellow oil.

d) It was dissolved in 5 ml of ethanol and 2 ml of tetrahydrofuran and treated with a solution of 2 g of potassium hydroxide in 5 ml of water. The reaction mixture was stirred at 40° C. for 3 hours, then poured on ice water, acidified with 3N HCl and extracted with ethyl acetate. The organic phase was washed with water, dried ($MgSO_4$) and the solvent evaporated. The resulting foam was filtered through a short pad of silica gel (eluent hexane/ethyl acetate=1:1). Recrystallisation from acetonitril gave 1.1 g of the title compound as white crystals, m.p. 78–80° C.

EXAMPLE 18

Preparation of 4-[pentyl-(5,5,8,8-tetramethyl-5,6,7,8-tetrahydro-naphthalen-2-yl)-carbamoyloxy]-benzoic Acid a) 10 g of 5,6,7,8-tetrahydro-5,5,8,8-tetramethyl-2-naphthylamine were dissolved in 140 ml of methylene chloride. After the addition of 50 ml of pyridine, the reaction mixture was cooled to 0° C., treated dropwise with 34 ml of trifluoroacetic anhydride, stirred at 0° C. for 2 hours, poured on ice water and extracted with ether. The organic phase was washed with water, dried ($Na_2SO_4$) and the solvent evaporated to give an orange oil which was purified with flash chromatography (silica gel, eluent hexane/ethyl acetate=4:1) and crystallized from hexane to yield 15 g of white crystals, m.p. 154–155° C. The compound was dissolved in 100 ml of DMSO and treated with 3.4 g of potassium hydroxide. The reaction mixture was cooled to 0° C., treated dropwise with 12 g of iodopentane dissolved in 15 ml of DMSO and stirred at room temperature for 24 hours. The crude product which was received after the usual workup (ice water/ether), was purified by column chromatography (silica gel, hexane/10% ethyl acetate) to give 13.9 g of a colorless oil.

The crude oil was dissolved in 140 ml of ethanol, treated with a solution of 10 g of potassium hydroxide in 20 ml of water and stirred at room temperature for 2 hours. The reaction mixture was poured on ice water, extracted with ether, dried ($Na_2SO_4$) and the solvent evaporated. The oily residue was filtered through silica gel (eluent hexane/10% ethyl acetate) to give 9.8 g of pentyl-(5,5,8,8-tetramethyl-5,6,7,8-tetrahydro-naphthalen-2-yl)-amine as a slightly yellow oil. A solution of 1 g of this amine in 20 ml of tetrahydrofuran was treated with 380 mg of triphosgene, heated to reflux for 3 hours, then poured on ice water and extracted with ethyl acetate. The organic phase was washed with water, dried ($MgSO_4$) and the solvent evaporated. The oily residue was crystallized in pentane to give 1.2 g of pentyl-(5,5,8,8-tetramethyl-5,6,7,8-tetrahydro-naphthalen-2-yl)-carbamoyl chloride in white crystals, m.p. 79–81° C.

b) 376 mg of sodium hydride (50% suspension in mineral oil) were suspended in 20 ml of DMF and treated at 0° C. with a solution of 4-hydroxy-benzoic acid benzyl ester in 10 ml of DMF. The reaction mixture was stirred at 0° C. until a clear solution was formed (about 15 minutes) and then treated with a solution of 1.2 g of the above mentioned carbamoyl chloride in 10 ml of DME After stirring at room temperature for 1 hour, the resulting suspension was poured on ice-cold, saturated aqueous ammonium chloride solution and extracted with ethyl acetate. The organic phase was washed with water, dried ($Na_2SO_4$) and the solvent evaporated. The oily residue was purified with flash chromatography (silica gel, eluent hexane/10% ethyl acetate) to give 1.4 g of 4-[pentyl-(5,5,8,8-tetramethyl-5,6,7,8-tetrahydro-naphthalen-2-yl)-carbamoyloxy]-benzoic acid benzyl ester as colorless oil.

It was dissolved in 50 ml of ethyl acetate and after addition of 400 mg of Pd—C, 10%, hydrogenated under normal pressure. After 30 minutes, the catalyst was filtered off, the filtrate evaporated, and the oily residue filtered through silica gel (eluent hexane/ethyl acetate=2:1) to give a colorless oil which crystallized in pentane. 750 mg of the title compound were received as white crystals, m.p. 100–102° C.

EXAMPLE 19

Preparation of (R,S)-4-[3-butoxy-3-(5,5,8,8-tetramethyl-5,6,7,8-tetrahydro-naphthalen-2-yl)-prop-1-ynyl]benzoic Acid a) A solution of 19.5 g of carbon tetrabromid in 300 ml of methylene chloride was cooled to −20° C. and treated with a solution of 30.8 g of triphenyl phosphine in 250 ml of methylene chloride. After stirring for 15 minutes at 0° C., a solution of 8.9 g of (RS)-butoxy-(5,5,8,8-tetramethyl-5,6,7,8-tetrahydro-naphthalen-2-yl)-acetaldehyde (synthesized according to example 17.b) in 100 ml of methylene chloride was added dropwise. The reaction mixture was stirred for 3.5 hours at room temperature, poured on ice water/saturated sodium bicarbonate solution and extracted with methylene chloride. The organic phase was washed with water, dried ($Na_2SO_4$) and evaporated. The brown residue was suspended in 300 ml of hexane, stirred for 30 minutes, filtered and the filtrate evaporated. The oily residue was purified with flash chromatography (silica gel, eluent hexane/ethyl acetate 5%) to give 11.5 g of 6-(3,3-dibromo-1-butoxy-allyl)-1,1,4,4-tetramethyl-1,2,3,4-tetrahydro-naphtahalene as a slightly yellow oil.

b) A solution of 11.2 g of this dibromide in 400 ml of tetrahydrofuran was cooled to −78° C. and treated dropwise with 31,4 ml of a 1.6 M solution of butyl lithium in hexane. The reaction mixture was stirred for one hour at room temperature, poured on ice/saturated aqueous ammonium chloride solution and extracted with ethyl acetate. The combined organic extracts were washed with water, dried ($MgSO_4$) and evaporated. The oily residue was purified with flash chromatography (silica gel, eluent hexane/ethyl acetate 2.5%) to give 3.6 g of 6-(1-butoxy-prop-2-ynyl)-1,1,4,4-tetramethyl-1,2,3,4-tetrahydronaphtahalene as colorless oil.

c) 3.8 g of 4-iodobenzoic acid methyl ester were dissolved in 50 ml of dimethylformamide (DMF) and treated successively with 8.2 ml of triethylamine, 414 mg of dichloro-bis (triphenylphosphine) palladium and 224 mg of cuprous iodide. The solution was evacuated and ventilated with argon, then treated with a solution of 3.5 g of the alkyne in 20 ml of DMF. The reaction mixture was stirred for 2 hours at room temperature under argon, poured on ice/saturated aqueous ammonium chloride solution and extracted with ether. The combined organic extracts were washed with water, dried ($MgSO_4$) and evaporated. The residue was purified by chromatography (silica gel, eluent hexane/ethyl acetate 3%) to give 3.3 g of 4-[3-butoxy-3-(5,5,8,8-tetramethyl-5,6,7,8-tetrahydronaphthalen-2-yl)-prop-1-ynyl]-benzoic acid methyl ester as slightly yellow oil.

The oil was dissolved in 25 ml of ethanol and treated with a solution of 4.3 g of potassium hydroxide in 10 ml of water. The reaction mixture was stirred for 5 hours at room temperature, poured on ice water, acidified with 3NHCl and extracted with ethyl acetate. The combined organic extracts were washed with water, dried ($MgSO_4$) and evaporated. The solid residue was recrystallized from acetonitrile to give 1.2 g of the title compound as yellow crystals, m.p. 140–143° C.

EXAMPLE 20

Preparation of (R,S)-4-[(5,5,8,8-tetramethyl-5,6,7,8-tetrahydro-naphthalen-2-yl)-p-tolyloxy-acetoxy]-benzoic Acid a) A solution of 5.7 g of oxo-(5,5,8,8-tetramethyl-5,6,7,8-tetrahydro-naphthalen-2-yl)-acetic acid ethyl ester (prepared according to example 15a) in 80 ml of ethanol was cooled to −10° C. and treated with 380 mg of sodium borohydride. The reaction mixture was stirred for 0.5 hours at −10° C., poured on ice water, acidified with 0.1 N HCl and extracted with ethyl acetate. The combined organic extracts were washed twice with water, dried ($MgSO_4$) and evaporated. The residue was purified by flash chromatography (silica gel, eluent hexane/ethyl acetate=4:1) to give 5.6 g of (R,S)-hydroxy-(5,5,8,8-tetramethyl-5,6,7,8-tetrahydro-naphthalen-2-yl)-acetate acid ethyl ester as slightly yellow oil.

b) A mixture of 1 g of the hydroxy compound, 1.1 g of thionyl bromide and 3 drops of DMF was stirred for 0.5 hours at room temperature, poured on ice water and extracted with ethyl acetate. The combined organic extracts were washed with water, dried ($MgSO_4$) and evaporated. The brown, oily residue was purified with flash chromatography (silica gel, eluent hexane/ethyl acetate 5%) to give 1.2 g of (RS)-bromo-(5,5,8,8-tetramethyl-5,6,7,8-tetrahydro-naphthalen-2-yl)-acetic acid ethyl ester as slightly yellow oil.

c) A solution of 184 mg of p-cresol in 3 ml of THF was added dropwise to a suspension of 82 mg of sodium hydride (ca 50% of mineral oil) in 2 ml of THF at 0° C. After 15 minutes of stirring at 0° C., hydrogen development stopped and a solution of 500 mg of bromo-ester in 5 ml of THF was added dropwise. The reaction mixture was stirred at room temperature for 4 hours, then poured on ice/saturated aqueous ammonium chloride solution and extracted with ether. The combined organic extracts were washed with water, dried ($MgSO_4$) and evaporated. The oily residue was purified with flash chromatography (silica gel, eluent hexane/ethyl acetate 3%) to give 430 mg of (RS)-(5,5,8,8-tetramethyl-5,6,7,8-tetrahydro-naphthalen-2-yl)-p-tolyloxy-acetic acid ethyl ester as yellow oil.

d) 395 mg of this ester were hydrolyzed in analogy to example 15.1.c) to give after recrystallisation from hexane 300 mg of (RS)-(5,5,8,8-tetramethyl-5,6,7,8-tetrahydro-2-yl)-p-tolyloxy-acetic acid as white crystals, m.p. 128–130° C.

e) 270 ml of this acid were coupled with 174 mg of 4-hydroxy-benzoic acid benzyl ester in analogy to example 15.1.d) using 158 mg of dicyclohexylcarbodiimide and 10 mg of 4-dimethylamino-pyridine to give after purification with flash chromatography (silica gel, eluent hexane/ethyl acetate 15%) 392 mg of (R,S)-4-[(5,5,8,8-tetra-methyl-5,6,7,8-tetrahydro-naphthalen-2-yl)-p-tolyloxy-acetoxy]-benzoic acid benzyl ester as colorless oil.

f) 376 mg of this benzyl ester were dissolved in 10 ml of ethyl acetate and, after the addition of 80 mg of 10% Pd—C, hydrogenated at normal pressure/room temperature. After 0.5 hours, the catalyst was filtered off, the filtrate evaporated and the oily residue purified with flash chromatography (silica gel, eluent hexane/ethyl acetate 15%) to give, after recrystallisation from acetonitrile, 161 mg of the tile compound as white crystals, m.p. 174–176° C.

EXAMPLE 21

Preparation of (RS)-4-[3-benzyloxy-3-(5,5,8,8-tetramethyl-5–6-7-8-tetrahydro-naphthalen-2-yl)-propenyl]-benzoic Acid 2.5 g of oxo-(5,5,8,8-tetramethyl-5,6,7,8-tetrahydro-naphthalen-2-yl)-acetic acid ethyl ester (example 15.1.a) were reacted with 1.5 g of benzyloxytrimethylsilane according to the procedure given in example 15.1.b) to give 1.2 g of (RS)-benzyloxy-(5,5,8,8-tetramethyl-5,6,7,8-tetrahydro-naphthalen-2-yl)-acetic acid ethyl ester as slightly yellow oil.

It was reduced with DIBAH in analogy to the procedure given in example 17a) to (RS)-2-benzyloxy-2-(5,5,8,8-tetramethyl-5–6-7-8-tetrahydro-naphthalen-2-yl)-ethanol (yield 1.05 g, colorless oil), oxidized to (RS)-benzyloxy-(5,5,8,8-tetramethyl-5,6,7,8-tetrahydro-naphthalen-2-yl)-acetaldehyde (yield 420 mg, slightly yellow oil) in analogy to example 17b), reacted with diethyl (4-carbethoxybenzyl) phosphate in analogy to example 17c) and hydrolyzed to the title compound according to example 17d). 312 mg were obtained as amorphous, colorless foam.

$^1$H NMR ($CDCl_3$): §1.28 (s, 12H), 1.68 (s, 4H, 4.55 qu, 2H, J=12 Hz), 4.97 (d, 1H, J=6.4 Hz), 6.48 (dd, 1H, J=16 Hz, 6.8 Hz), 6.69 (d, 1H, J=16 Hz), 7.15–7.46 (m, 8H), 7.46 (d, 2H, J=8 Hz), 8.02 (d, 2H, J=8 Hz)

EXAMPLE 22

22.1 Preparation of (R,S)-4-[3-(4-chloro-phenoxy)-3-(5,5,8,8-tetramethyl-5,6,7,8-tetrahydro-naphthalen-2-yl)-propenyl]-benzoic Acid:

a) 326 mg of sodium hydride (50% in mineral oil) were suspended in 10 ml of THF and treated dropwise at 0° C. with a solution of 734 mg of 4-chlorophenol in 10 ml of THF. After stirring for 15 minutes at 0° C., a solution of 2 g of (R, S)-bromo-(5,5,8,8-tetramethyl-5,6,7,8-tetrahydro-naphthalen-2-yl)-acetic acid ethyl ester (synthesized according to example 20b) in 20 ml of THF was added dropwise to the gray suspension. The reaction mixture was stirred for 4 hours at room temperature, then poured on 200 ml of ice water and extracted with ethyl acetate. The organic phase was washed with water, dried ($MgSO_4$) and evaporated. The yellow, oily residue was purified by flash chromatography (silica gel, eluent hexane/ethyl acetate=9:1) to give 1,8 g of (R,S)-5,5,8,8-tetramethyl-5,6,7,8-tetrahydro-naphthalen-2-yl)-p-chlorophenoxy-acetic acid ethyl ester as colorless oil.

b) This ester (1.8 g) was dissolved in 25 ml of ether and treated dropwise at −78° C. with 13.4 ml of a 1 M solution of DIBAH in hexane. The reaction mixture was stirred for 1.5 hours at 0° C., cooled to −10° C. and carefully treated with 1 ml of a 2 M solution of Rochelle salt in water, followed by addition of further 4 ml of this reagent. The resulting white suspension was stirred at room temperature for 1.5 hours, filtered, the residue washed well with ether and the combined organic solution dried ($MgSO_4$), and the solvent evaporated. The oily residue was filtered through a pad of silica gel (eluent hexane/ethyl acetate=9:1) to give 1.47 g of (R,S)-2-(p-chlorophenoxy)-2-(5,5,8,8-tetramethyl-5,6,7,8-tetrahydronaphthalen-2-yl)-ethanol as colorless oil.

c) 1.25 g of this alcohol were dissolved in 30 ml of methylene chloride and added to a solution of 1.7 g of Dess-Martin reagent in 100 ml of methylene chloride at room temperature. The reaction mixture was stirred for 2 hours, diluted with 100 ml of ether, washed with water, dried (MgSO$_4$) and evaporated. The oily residue was further purified by flash chromatography (silica gel, eluent hexane/ 5% ethyl acetate) to give 940 mg of (R,S)-p-chloro-phenoxy-(5,5,8,8-tetramethyl-5,6,7,8-tetrahydro-naphthalen-2-yl)-acetaldehyde as pale yellow oil.

d) 1.2 g of diethyl (4-carbethoxybenzyl) phosphonate were dissolved in 10 ml of THF, cooled to −20° C. and treated dropwise with 3.9 ml of a 1M solution of lithium bis(trimethylsilyl)amide in hexane. After 15 minutes, a solution of 940 mg of the above mentioned aldehyde in 5 ml of THF was added dropwise. The reaction mixture was warmed to room temperature, stirred for 2 hours, then poured on saturated, aqueous ammonium chloride solution and extracted with ethyl acetate. The combined organic phases were dried (MgSO$_4$) and evaporated. The oily residue was purified by flash chromatography (silica gel, eluent hexane/5% ethyl acetate) to give 590 mg of (R,S)-4-[3-(4-chlorophenoxy)-3-(5,5,8,8-tetramethyl-5,6,7,8-tetrahydro-naphthalen-2-yl)-propenyl]-benzoic acid ethyl ester as a colorless foam.

e) It was dissolved in 5 ml of ethanol and treated with a solution of 246 mg of LiOH.H$_2$O in 2 ml of water. The reaction mixture was stirred at room temperature for 4 hours, then poured on ice water, acidified with 1N HCl and extracted with ethyl acetate. The organic phase was washed with water, dried (MgSO$_4$) and the solvent evaporated. The oily residue was purified by flash chromatography (silica gel, eluent hexane/ethyl acetate=4:1) to give after recrystallisation from ethyl acetate/hexane 200 mg of (R,S)-4-[3-(4-chloro-phenoxy)-3-(5,5,8,8,-tetramethyl-5,6,7,8-tetrahydro-naphthalen-2-yl)-propenyl]-benzoic acid as white crystals, m.p. 115–116° C.

In analogy to example 22.1, by using 4-trifluoromethyl-phenol, p-cresol and 4-methoxyphenol respectively as starting material, the following compounds were synthesized:

22.2. (R,S)-4-[3-(5,5,8,8-tetramethyl-5,6,7,8-tetrahydro-naphthalen-2-yl)-3-(4-trifluoromethyl-phenoxy)-propenyl]-benzoic acid, m.p. 97–99° C.

22.3. (R,S)-4-[3-(5,5,8,8-tetramethyl-5,6,7,8-tetrahydro-naphthalen-2-yl)-3-p-tolyloxy-propenyl]-benzoic acid, m.p. 141–142° C.

22.4. (R,S)-4-[3-(5,5,8,8-tetramethyl-5,6,7,8-tetrahydro-naphthalen-2-yl)-3-(4-methoxy-phenoxy)-propenyl]-benzoic acid, m.p. 178–183° C.

EXAMPLE 23

Preparation of (R,S)-4-[3-(4,4-Dimethyl-chroman-6-yl)-oct-1-enyl]-benzoic Acid.

a) A mixture of 4.7 g of 6-acetyl-4,4-dimethyl-chroman, 2.7 g of morpholine, 740 mg of sulfur and 97 mg of p-toluenesulfonic acid was refluxed under argon for 22 hours. The darkbrown reaction mixture was cooled to room temperature, treated dropwise with 11 ml of methanol, stirred at 0° C. for 2 hours and evaporated to dryness. The brown, oily residue was purified by column chromatography (silica gel, eluent hexane/ethyl acetate=4:1) to give 3.3 g of a colorless oil. It was dissolved in a mixture of 25 ml of acetic acid, 2.3 ml of water and 3.8 ml of concentrated sulfuric acid. The reaction mixture was refluxed under argon for 15 hours (oilbath temperature 150° C.), cooled to room temperature, poured on 100 ml of ice water and extracted with ethyl acetate. The organic phase was dried (MgSO$_4$) and evaporated. The brown, oily residue was chromatographed (silica gel, eluent hexane/ethyl acetate=1:1) to give after recrystallisation from hexane 2.0 g of (4,4-dimethyl-chroman-6-yl)-acetic acid as slightly beige crystals, m.p. 108–109° C.

b) 1.2 g of diisopropylamine were dissolved in 30 ml of THF, cooled to 0° C. and treated under argon with 7.2 ml of n-butyl lithium, 1.6 molar in hexane. After stirring for 30 minutes, a solution of 1 g of (4,4-dimethyl-chroman-6-yl)-acetic acid in 10 ml of THF was dropped in. The reaction mixture was stirred at 0° C. for 30 minutes, then at room temperature for 30 minutes, recooled to 0° C. and treated dropwise with 1.4 g of pentyl iodide. The reaction mixture was stirred at room temperature for 1 hour, then poured on ice water, acidified with 3 N HCl and extracted 3 times with ethyl acetate. The combined organic extracts were dried (MgSO$_4$) and evaporated. The resulting yellow oil was purified by chromatography (silica gel, eluent hexane/ethyl acetate=4:1) to give 930 mg of (R,S)-2-(4,4-dimethyl-chroman-6-yl)-heptanoic acid as colorless oil, which solidified on standing in the refrigerator.

c) The whole amount of this acid (930 mg) was dissolved in 20 ml of THF, cooled to 0° C. and treated under argon with 16 ml of borane-dimethylsulfide, 1 N in THF. The reaction mixture was stirred for 2 hours at 0° C., carefully quenched with 3 N HCl and stirred at 0° C. for 30 minutes, followed by extraction with ethyl acetate. The organic phases were dried (MgSO$_4$) and evaporated. The resulting yellow oil was purified by flash chromatography (silica gel, eluent hexane/ethyl acetate=4:1) to give 708 mg of (R,S)-2-(4,4-dimethyl-chroman-6-yl)-heptanol as slightly yellow oil.

d) 0.5 ml of oxalyl chloride were dissolved in 20 ml of methylene chloride and carefully treated with 0.6 ml of DMSO at −70° C. After 5 minutes of stirring at −70° C., 700 mg of (R,S)-2-(4,4-dimethyl-chroman-6-yl)-heptanol dissolved in 10 ml of methylene chloride, were added dropwise. The reaction mixture was stirred at −78° C. for 15 minutes, treated with 1.8 ml of triethylamine, warmed to room temperature, stirred for 1 hour at this temperature, poured on ice water and extracted several times with methylene chloride. The combined organic extracts were washed with water, dried (MgSO$_4$) and evaporated. The resulting oil was purified by flash chromatography (silica gel, eluent hexane/15% ethyl acetate) to give 680 mg of (R,S)-2-(4,4-dimethyl-chroman-6-yl)-heptanal as slightly beige oil.

e) A solution of 1.1 g of diethyl (4-carbethoxybenzyl) phosphonate in 10 ml of THF was treated at −20° C. with 3.7 ml of lithium bis(trimethylsilyl)amide, 1N in hexane. After 15 minutes, a solution of 670 mg of (R,S)-2-(4,4-dimethyl-chroman-6-yl)-heptanal in 5 ml of THF was added dropwise. The reaction mixture was stirred at −20° C. for 15 minutes and at room temperature for 1.5 hours, then poured on a mixture of ice and saturated aqueous ammonium chloride solution and extracted with ethyl acetate. The organic extracts were washed with water, dried (MgSO$_4$) and evaporated. The resulting yellow oil was purified by flash chromatography (silica gel, eluent hexane/3% ethyl acetate) to give 940 mg of (R,S)-4-[3-(4,4-dimethyl-chroman-6-yl)-oct-1-enyl]-benzoic acid ethyl ester as colorless oil.

f) It was dissolved in 15 ml of ethanol and treated with a solution of 1.25 g of potassium hydroxyde in 3 ml of water. The reaction mixture was stirred at room temperature for 3 hours, then poured on ice water, acidified with 2 N HCl and extracted with ethyl acetate. The organic phase was washed with water, dried (MgSO$_4$) and evaporated. The resulting white foam was purified by flash chromatography (silica gel, eluent hexane/ethyl acetate=1:1) to give after recrystallisation from acetonitril 620 mg of (R,S)-4-[3-(4,4,-dimethyl-chroman-6-yl)-oct-1-enyl]-benzoic acid as white crystals, m.p. 88–91° C.

EXAMPLE 24

Preparation of (R,S)-4-[2-(4,4-Dimethyl-chroman-6-yl)-heptanoyloxy]-benzoic Acid.

a) 925 mg of (R,S)-2-(4,4-dimethyl-chroman-6-yl)-heptanoic acid (synthesized according to example 23b) were dissolved in 20 ml of methylene chloride followed by the addition of 730 mg of 4-hydroxy-benzoic acid benzyl ester and 36 mg of 4-dimethylamino-pyridine. The solution was cooled to 0° C. and treated dropwise with a solution of 660 mg of dicyclohexylcarbodiimide in 10 ml of methylene chloride. The reaction mixture was stirred at room temperature for 5 hours, then poured on ice water and extracted with 3 portions of 100 ml of ethyl acetate. The combined organic extracts were washed with water, dried (MgSO$_4$) and evaporated. The remaining yellow oil was purified by flash chromatography (silica gel, eluent hexane/ethyl acetate=4:1) to give 1.5 g of (R,S)-4-[2-(4,4-dimethyl-chroman-6-yl) heptanoyloxy]benzoic acid benzyl ester as slightly yellow oil.

b) It was dissolved in 20 ml of ethyl acetate and, after the addition of 300 mg of 10% Pd—C, hydrogenated at normal pressure and room temperature. After 1.5 hours of vigorous stirring, 85 ml of hydrogen were absorbed. The catalyst was filtered off, the filtrate evaporated and the remaining colorless oil purified by flash chromatography (silica gel, eluent hexane/ethyl acetate=4:1) to give after recrystallization from pentane 800 mg of (R,S)-4-[2-(4,4-dimethyl-chroman-6-yl)-heptanoyloxy]-benzoic acid as white crystals, m.p. 85–87° C.

EXAMPLE 25

Preparation of (RS)-4-[3-(5,5,8,8-tetramethyl-5,6,7,8-tetrahydronaphthalen-2-yl)-oct-1-yl]-benzoic Acid 200 mg of (RS)-4-[3-(5,5,8,8-tetramethyl-5,6,7,8-tetrahydronaphthalen-2-yl)-oct-1-enyl]-benzoic acid were dissolved in 20 ml of absolute ethanol and 60 mg of 30% Pd on carbon were added. The reaction flask was purged from the oxygen by vacuum and hydrogen filling (two times). The mixture was subjected to atmospheric H$_2$ pressure for 6 hours. The reaction mixture was filtered on a pad of Celite and concentrated in vacuo. The product was purified by preparative tlc (SiO$_2$, 5% methanol/methylene chloride), giving 140 mg of the titled compound as a white solid. 1H NMR (CDCl$_3$): 7.99 (d, J=8.3 Hz, 2H), 7.21 (d, J=8.1 Hz, 1H), 7.19 (d, J=8.3 Hz, 2H), 7.02 (d, J=1.8 Hz, 1H), 6.89 (dd, J=8.1, 1.8 Hz, 1H), 2.60–2.35 (m, 3H), 2.05–1.80 (m, 2H), 1.68 (s, 4H), 1.60–1.45 (m, 2H), 1.28 (s, 3H), 1.27 (s, 9H), 1.30–1.10 (m, 6H), 0.82 (t, J=6.7 Hz, 3H).

EXAMPLE 26

26.1. Preparation of (R)-4-(1-methylethyl)-3-[(R)-2-(5,5,8,8-tetramethyl-5,6,7,8-tetrahydronaphthalen-2-yl)-heptanoyl]-5,5-diphenyloxazolidin-2-one 2.0 g of (RS)-2-(5,5,8,8-tetramethyl-5,6,7,8-tetrahydronaphthalen-2-yl)-heptanoic acid were dissolved in 30 ml of THF and cooled to −30° C. To the cooled mixture, were added successively, 2.3 ml of triethylamine and 780 µl of trimethylacetyl chloride. The mixture was kept at −30° C. for two hours. 308 mg of lithium chloride were added followed by 978 mg of (R)-4-(1-methylethyl)-5,5-diphenyloxazolidin-2-one (Hintermann T., Seebach D., *Helv. Chim. Acta*, 1998, 81, 2093). The mixture was allowed to warm to room temperature and was kept at that temperature for 18 hours. The reaction mixture was quenched by the addition of one portion of 30 ml of a saturated aqueous ammonium chloride solution. The resulting mixture was extracted with three portions of 30 ml of ether. The combined organic extracts were washed with two portions of 30 ml of 1N hydrochloric solution, one portion of 30 ml of water and one portion of 30 ml of saturated aqueous sodium chloride solution. The organic phase was dried over MgSO$_4$ and the solvent evaporated. The residual yellow oil was purified by flash chromatography (SiO$_2$, 3% ethyl acetate/hexanes to 20% ethyl acetate/hexanes, dry pack), yielding 1.8 g of the titled compound and 0.8 g of the starting acid, 1H NMR (CDCl$_3$): 7.40–7.20 (m, 6H), 7.15–6.95 (m, 6H), 6.77 (dd, J=8.2, 2.0 Hz, 1H), 5.26 (d, J=3.4 Hz, 1H), 4.92 (dd, J=8.8, 6.2 Hz, 1H), 2.15 (m, 1H), 1.97 (m, 1H), 1.70 (m, 1H), 1.58 (br. s, 4H), 1.35–1.25 (m, 6H), 1.23 (s, 3H), 1.20 (s, 3H), 1.17 (s, 3H), 1.03 (s, 3H), 0.92 (d, J=7.0 Hz, 3H), 0.85 (t, J=6.8 Hz, 3H), 0.80 (d, J=6.8 Hz, 3H).

[α]$_D$=+63.5 (c=0.502, in CHCl$_3$).

In analogy to example 26.1, the opposite enantiomer was also prepared, using the (S)-4-(1-methylethyl)-5,5-diphenyloxazolidin-2-one:

26.2. (S)-4-(1-Methylethyl)-3-(S)-2-(5,5,8,8-tetramethyl-5,6,7,8-tetrahydronaphthalen-2-yl)-heptanoyl]-5,5-diphenyloxazolidin-2-one, [α]$_D$=−63.5 (c=0.492, in CHCl$_3$).

EXAMPLE 27

27.1. Preparation of (R)-2-(5,5,8,8-tetramethyl-5,6,7,8-tetrahydronaphthalen-2-yl)-heptanol 1.8 g of (R)-4-(1-methylethyl)-3-[(R)-2-(5,5,8,8-tetramethyl-5,6,7,8-tetrahydronaphthalen-2-yl)-heptanoyl]-5,5-diphenyloxazolidin-2-one were dissolved in 40 ml of ether and treated with 945 mg of lithium aluminium hydride. The reaction mixture was kept at room temperature for 4 hours. The mixture was quenched at 0° C. with 0.95 ml of water, followed by 0.95 ml of a 15% sodium hydroxide solution and 3 ml of water. The mixture was vigorously stirred for 30 min. at room temperature. MgSO$_4$ was added and the mixture was filtered. Concentration in vacuo yielded a yellow oil which was purified by flash chromatography (SiO$_2$, 10% ethyl acetate/hexanes, dry pack). [α]$_D$=−11.0 (c=0.258, in CHCl$_3$).

In analogy to example 27.1. the opposite enantiomer was also prepared, using the (S)-4-(1-methylethyl)-3-[(S)-2-(5,5,8,8-tetramethyl-5,6,7,8-tetrahydronaphthalen-2-yl)-heptanoyl]-5,5-diphenyloxazolidin-2-one.

27.2. (S)-2-(5,5,8,8-Tetramethyl-5,6,7,8-tetrahydronaphthalen-2-yl)-heptanol, [α]$_D$=+11.5 (c=0.307, in CHCl$_3$).

EXAMPLE 28

28.1. Preparation of [(R)-4-[2-(5,5,8,8-tetramethyl-5,6,7,8-tetrahydronaphthalen-2-yl)-heptyloxy]-benzoic Acid]

850 mg of (R)-2-(5,5,8,8-tetramethyl-5,6,7,8-tetrahydronaphthalen-2-yl)-heptanol dissolved in 50 ml THF were treated with 810 mg of triphenylphosphine, 470 mg of methyl 4-hydroxybenzoate and 0.49 ml of diethyl azodicarboxylate. The reaction mixture was heated to reflux for 6 hours. The mixture was diluted with 100 ml of ether and washed with two portions of 25 ml of water and one portion of 25 ml of sat. aq. sodium chloride solution. The organic phase was dried over MgSO$_4$. The solvents were removed in vacuo and the resulting yellow oil was purified by flash chromatography (SiO$_2$, 3% ethyl acetate/hexanes), giving 1 g of (R)-methyl 4-[2-(5,5,8,8-tetramethyl-5,6,7,8-tetrahydronaphthalen-2-yl)-heptyloxy]-benzoate as a colorless oil, [α]$_D$=−23.3 (c=0.307, in CHCl$_3$).

The ester (1 g), dissolved in 20 ml THF/5 ml H$_2$O/5 ml methanol, was treated with 380 mg of lithium hydroxide hydrate. The mixture was stirred at room temperature 4 hours. The mixture was diluted with 50 ml water and acidified to pH 2 with 1N hydrochloric. The resulting suspension was taken in 100 ml ether and the phases were separated. The aqueous phase was extracted with three portions of 50 ml ether. The combined extracts were dried over $MgSO_4$. The solvent was removed in vacuo and the crude product was purified recrystalization from acetonitrile/water, yielding 796 mg of product as shining platelets. M.p. 74–76° C., $[\alpha]_D$=−22.2 (c=0.500, in $CHCl_3$).

In analogy to example 28.1., the opposite enantiomer was also prepared:

28.2. [(S)-4-[2-(5,5,8,8-Tetramethyl-5,6,7,8-tetrahydronaphthalen-2-yl)-heptyloxy]-benzoic acid], m.p. 76–77° C., $[\alpha]_D$=+23.1 (c=0.506, in $CHCl_3$).

EXAMPLE 29

29.1. Preparation of 2-methyl-2-(5,5,8,8-tetramethyl-5,6,7,8-tetrahydronaphthalen-2-yl)-propanoic Acid 2 g of (RS)-2-(5,5,8,8-tetramethyl-5,6,7,8-tetrahydronaphthalen-2-yl)-propanoic acid dissolved in 100 ml THF were treated with 9.6 ml of a 2M lithium diisopropylamide solution, at −23° C. The mixture was kept at that temperature for 15 min. then, 1.19 ml of methyl iodide were added dropwise. The reaction mixture was kept at 0° C. for 4 hours then allowed to warm at room temperature for several days. The mixture was quenched with 100 ml of 1N hydrochloric acid solution. The mixture was extracted with three portions of 100 ml of ethyl acetate. The combined organic extracts were washed with 100 ml of a saturated aqueous sodium chloride solution. The organic phase was dried with $MgSO_4$, and the solvent was evaporated. The yellow oil was purified by flash chromatography ($SiO_2$, 20% ethyl acetate/hexanes). 1H NMR ($CDCl_3$): 7.31 (d, J=2.2 Hz, 1H), 7.24 (d, J=8.3 Hz, 1H), 7.15 (dd, J=8.3, 2.2 Hz, 1H), 1.67 (s, 4H), 1.58 (s, 6H), 1.27 (s, 6H), 1.26 (s, 6H).

In analogy to example 29.1., by using the appropriate alkyl iodide and appropriate substrate, the following compounds were synthesized:

29.2. 2-Propyl-2-(5,5,8,8-tetramethyl-5,6,7,8-tetrahydronaphthalen-2-yl)-pentanoic acid, 1H NMR ($CDCl_3$): 7.25–7.15 (m, 2H), 7.04 (dd, J=8.4, 2.1 Hz, 1H), 2.05–1.85 (m, 4H), 1.66 (s, 4H), 1.26 (s, 6H), 1.25 (s, 6H), 1.25–1.05 (m, 4H), 0.90 (t, J=7.0 Hz, 6H).

EXAMPLE 30

30.1. Preparation of 2-methyl-2-(5,5,8,8-tetramethyl-5,6,7,8-tetrahydronaphthalen-2-yl)-propanol 0.66 g of 2-methyl-2-(5,5,8,8-tetramethyl-5,6,7,8-tetrahydronaphthalen-2-yl)-propanoic acid dissolved in 14 ml THF were treated with 24 ml of 1M lithium aluminium hydride solution in ether. The mixture was stirred at room temperature for 18 hours. The mixture was quenched by slowly adding $Na_2SO_4 \cdot H_2O$ until no more $H_2$ evolved. The solid was filtered off and the solvent was evaporated, giving a pale yellow oil which was purified by flask chromatography ($SiO_2$, 10% ethyl acetate/hexanes). 1H NMR ($CDCl_3$): 7.29 (d, J=2.2 Hz, 1H), 7.25 (d, J=8.3 Hz, 1H), 7.12 (dd, J=8.3, 2.2 Hz, 1H), 3.55 (br. d, J=5.4 Hz, 2H), 1.67 (s, 4H), 1.31 (s, 6H), 1.28 (s, 6H), 1.27 (s, 6H).

In analogy to example 30.1., the following compound was synthesized:

30.2. 2-Propyl-2-(5,5,8,8-tetramethyl-5,6,7,8-tetrahydronaphthalen-2-yl)-pentanol, 1H NMR ($CDCl_3$): 7.40–7.30 (m, 2H), 7.05 (dd, J=8.4, 2.1 Hz, 1H), 3.66 (s, 2H), 1.75–1.55 (m, 4H), 1.67 (s, 4H), 1.27 (s, 6H), 1.26 (s, 6H), 1.35–1.05 (m, 4H), 0.88 (t, J=7.0 Hz, 6H).

EXAMPLE 31

31.1. Preparation of 4-[2-methyl-2-(5,5,8,8-tetramethyl-5,6,7,8-tetrahydronaphthalen-2-yl)-propyloxy]-benzoic Acid 305 mg of 2-methyl-2-(5,5,8,8-tetramethyl-5,6,7,8-tetrahydronaphthalen-2-yl)-propanol dissolved in 15 ml THF were treated with 338 mg of triphenylphosphine, 196 mg of methyl 4-hydroxybenzoate and 0.21 ml of diethyl azodicarboxylate. The reaction mixture was heated to reflux for 6 hours. The mixture was partitioned in 100 ml of 1:1 ethyl acetate/sat. aq. sodium chloride solution. The phases were separated and the organic phase was dried over $MgSO_4$. The solvents were removed in vacuo and the resulting oil was purified by flash chromatography ($SiO_2$, 20% ethyl acetate/hexanes), giving 160 mg of methyl 4-[2-methyl-2-(5,5,8,8-tetramethyl-5,6,7,8-tetrahydronaphthalen-2-yl)-propyloxy]-benzoate as a colorless oil. The ester (160 mg), dissolved in 4 ml THF/0.8 ml $H_2O$, was treated with 50 mg of lithium hydroxide hydrate. The mixture was heated at 60° C. for two hours. The mixture was acidified to pH 2 with 1N hydrochloric acid then partitioned in 10 ml ethyl acetate/10 ml sat. aq. sodium chloride solution. The phases were separated and the organic phase was dried over $MgSO_4$. The solvent was removed in vacuo and the crude product was purified by preparation tlc ($SiO_2$, 40% ethyl acetate/hexanes), giving a white foam. 1H NMR ($CDCl_3$): 8.03 (d, J=8.8 Hz, 2H), 7.35 (d, J=2.1 Hz, 1H), 7.26 (d, J=8.4 Hz, 1H), 7.17 (dd, J=8.4, 2.1 Hz, 1H), 6.91 (d, J=8.8 Hz, 2H), 3.96 (s, 2H), 1.67 (s, 4H), 1.46 (s, 6H), 1.27 (s, 12H).

In analogy to example 31.1., the following compound was synthesized:

31.2. 4-[2-Propyl-2-(5,5,8,8-tetramethyl-5,6,7,8-tetrahydronaphthalen-2-yl)-pentyloxy]-benzoic acid, 1H NMR ($CDCl_3$): 8.05 (d, J=8.9 Hz, 2H), 7.21 (d, J=8.3 Hz, 1H), 7.11 (d, J=2.1 Hz, 1H), 7.03 (dd, J=8.3, 2.1 Hz, 1H), 6.98 (d, J=8.9 Hz, 2H), 4.14 (s, 2H), 1.67 (s, 4H), 1.60–1.40 (m, 4H), 1.30–1.10 (m, 4H), 1.27 (s, 3H), 1.26 (s, 3H), 1.25 (s, 3H), 1.22 (s, 3H), 0.88 (t, J=7.1 Hz, 6H).

EXAMPLE 32

32.1. Preparation of 2-methyl-2-(5,5,8,8-tetramethyl-5,6,7,8-tetrahydronaphthalen-2-yl)-propionitrile 1.02 g of (5,5,8,8-tetramethyl-5,6,7,8-tetrahydronaphthalen-2-yl)-acetonitrile (Farmer, L. et al., Bioorg. Med. Chem. Lett., 1997, 7, 2747), dissolved in 12 ml THF, were treated with 2.9 ml of t-butyl lithium (1.7 M) at −78° C. The reaction mixture was stirred at −78° C. for 10 min. then 0.31 ml of methyl iodide were added. The mixture was stirred at 45° C. for 30 min. After cooling to −78° C., 2.9 ml of t-butyl lithium (1.7M) were added followed by 0.31 ml of methyl iodide 15 min. later. The mixture was stirred at room temperature for 30 min. The mixture quenched by the addition of 15 ml of water and the resulting mixture was partitioned in 25 ml ethyl acetate/25 ml sat. aq. sodium chloride solution. The phases were separated and the organic phase was dried over $MgSO_4$. The solvent was removed in vacuo and the crude product was purified by flash chromatography ($SiO_2$, 10% ethyl acetate/hexanes), giving 1.12 g of the titled compound. 1H NMR ($CDCl_3$): 7.40 (d, J=2.2 Hz, 1H), 7.31 (d, J=8.3 Hz, 1H), 7.18 (dd, J=8.3, 2.2 Hz, 1H), 1.71 (s, 6H), 1.69 (s, 4H), 1.30 (s, 6H), 1.27 (s, 6H).

In analogy to example 32.1., the following compounds were synthesized:

32.2. 2-Ethyl-2-(5,5,8,8-tetramethyl-5,6,7,8-tetrahydronaphthalen-2-yl)-butyronitrile, 1H NMR (CDCl₃): 7.28 (d, J=2.2 Hz, 1H), 7.27 (d, J=8.3 Hz, 1H), 7.06 (dd, J=8.3, 2.2 Hz, 1H), 2.07–1.80 (m, 4H), 1.68 (s, 4H), 1.30 (s, 6H), 1.27 (s, 6H), 0.92 (t, J=7.4 Hz, 6H).

32.3. 2-Propyl-2-(5,5,8,8-tetramethyl-5,6,7,8-tetrahydronaphthalen-2-yl)-pentanenitrile, 1H NMR (CDCl₃): 7.29 (d, J=2.2 Hz, 1H), 7.25 (d, J=8.3 Hz, 1H), 7.06 (dd, J=8.3, 2.2 Hz, 1H), 2.00–1.70 (m, 4H), 1.68 (s, 4H), 1.55–1.45 (m, 2H), 1.30–1.10 (m, 2H), 1.28 (s, 6H), 1.27 (s, 6H), 0.88 (t, J=7.4 Hz, 6H).

EXAMPLE 33

33.1. Preparation of 2-methyl-2-(5,5,8,8-tetramethyl-5,6,7,8-tetrahydronaphthalen-2-yl)-propanal 1.12 g of 2-methyl-2-(5,5,8,8-tetramethyl-5,6,7,8-tetrahydronaphthalen-2-yl)-propionitrile, dissolved in 8 ml of dry toluene, was treated with 8.8 ml of a 1M diisobutylaluminium hydride solution in toluene. The mixture was heated to relux for 18 hours. The mixture quenched by the addition of 10 ml of water and the resulting mixture was partitioned in 25 ml ethyl acetate/25 ml sat. aq. sodium chloride solution. The phases were separated and the organic phase was dried over MgSO₄. The solvent was removed in vacuo and the crude product was purified by flash chromatography (SiO₂, 10% ethyl acetate/hexanes), giving 521 mg of the titled compound. 1H NMR (CDCl₃): 9.47 (s, 1H), 7.31 (d, J=8.3 Hz, 1H), 7.16 (d, J=2.2 Hz, 1H), 7.04 (dd, J=8.3, 2.2 Hz, 1H), 1.68 (s, 4H), 1.44 (s, 6H), 1.27 (s, 12H).

In analogy to example 33.1., the following compounds were synthesized:

33.2. 2-Ethyl-2-(5,5,8,8-tetramethyl-5,6,7,8-tetrahydronaphthalen-2-yl)-butanal, 1H NMR (CDCl₃): 9.46 (s, 1H), 7.28 (d, J=8.3 Hz, 1H), 7.09 (d, J=2.1 Hz, 1H), 6.95 (dd, J=8.3, 2.1 Hz, 1H), 1.94 (q, J=7.6 Hz, 4H), 1.67 (s, 4H), 1.27 (s, 6H), 1.26 (s, 6H), 0.76 (t, J=7.5 Hz, 6H).

33.3. 2-Propyl-2-(5,5,8,8-tetramethyl-5,6,7,8-tetrahydronaphthalen-2-yl)-pentanal, 1H NMR (CDCl₃): 9.45 (s, 1H), 7.27 (d, J=8.3 Hz, 1H), 7.08 (d, J=2.1 Hz, 1H), 6.96 (dd, J=8.3, 2.1 Hz, 1H), 1.95–1.85 (m, 4H), 1.67 (s, 4H), 1.27 (s, 6H), 1.26 (s, 6H), 1.20–1.05 (m, 4H), 0.91 (t, J=7.2 Hz, 6H).

EXAMPLE 34

34.1. Preparation of [(E)-4-[3-methyl-3-(5,5,8,8-tetramethyl-5,6,7,8-tetrahydronaphthalen-2-yl)-but-1-enyl]-benzoic Acid]

1.21 g of ethyl 4-(diethoxyphosphorylmethyl)-benzoate were dissolved in 18 ml THF and treated, at −20° C., with 4.23 ml of a 1M solution of lithium bis(trimethylsilyl)amide in hexane. After 15 min. at −20° C., a solution of 521 mg of 2-methyl-2-(5,5,8,8-tetramethyl-5,6,7,8-tetrahydronaphthalen-2-yl)-propanal in 14 ml THF was added. The reaction mixture was stirred at room temperature for 1.5 hour. The mixture quenched by the addition of 10 ml of water and the resulting mixture was partitioned in 50 ml ethyl acetate/25 ml sat. aq. sodium chloride solution. The phases were separated and the organic phase was dried over MgSO₄. The solvent was removed in vacuo and the crude product was purified by flash chromatography (SiO₂, 10% ethyl acetate/hexanes), giving 743 mg of the corresponding ester.

The ester (743 mg) were dissolved in 37 ml THF/7.5 ml water and 772 mg of lithium hydroxide hydrate were added. The reaction mixture was heated to 40° C. for 18 hours. The mixture was acidified to pH 2 with 1N hydrochloric acid then partitioned in 100 ml ethyl acetate/50 ml sat. aq. sodium chloride solution. The phases were separated and the organic phase was dried over MgSO₄. The solvent was removed in vacuo and the crude product was purified by flash chromatography (SiO₂, 40% ethyl acetate/hexanes), giving 691 mg of the titled compound as a white foam, m.p. 219–220° C.

In analogy to example 34.1., the following compounds were synthesized:

34.2. [E)-4-[3-Ethyl-3-(5,5,8,8-tetramethyl-5,6,7,8-tetrahydronaphthalen-2-yl)-pent-1-enyl]-benzoic acid], m.p. 144–145° C.

34.3. [(E)-4-[3-Propyl-3-(5,5,8,8-tetramethyl-5,6,7,8-tetrahydronaphthalen-2-yl)-hex-1-enyl]-benzoic acid], m.p. 65–68° C.

EXAMPLE 35

35.1. Preparation of (4,4-dimethyl-thiochroman-6-yl)-acetic Acid 9.7 g of 6-acetyl-4,4-dimethylthiochromane (J. Med. Chem., 1985, 28, 116) were dissolved in 5.25 ml of morpholine. 1.41 g of sulfur (S₈) were added, followed by 184 mg of p-toluenesulfonic acid hydrate. The mixture was heated to reflux for 22 hours. After cooling, 23 ml of methanol were added. The mixture was stirred at 0° C. for two hours then, the volatiles were removed in vacuo, giving a dark brown oil which was purified by flash chromatography (SiO₂, 10% ethyl acetate/hexanes), yielding 7.4 g of a golden oil.

The thioamide (6.5 g) was dissolved in 54 ml glacial acetic acid/8.3 ml water and then was treated with 5 ml of concentrated sulfuric acid. The mixture was heated to reflux for 14 hours. After cooling, the reaction mixture was poured onto 300 ml of iced water and then was extracted with three portions of 100 ml of ethyl acetate. The combined extracts were washed with one portion of 100 ml of water and one portion of 100 ml of saturated aqueous sodium chloride solution. The organic phase was dried over MgSO₄ and concentrated in vacuo, giving a black solid. The crude product was purified by flash chromatography (SiO₂, 10% methanol/methylene chloride), yielding 4.5 g of a beige solid. 1H NMR (CDCl₃): 7.24 (d, J=1.9 Hz, 1H), 7.04 (d, J=8.1 Hz, 1H), 6.96 (dd, J=8.1, 1.9 Hz, 1H), 3.56 (s, 2H), 3.05–2.95 (m, 2H), 2.00–1.90 (m, 2H), 1.31 (s, 6H).

EXAMPLE 36

36.1. Preparation of (RS)-2-(4,4-dimethyl-thiochroman-6-yl)-heptanoic Acid 1.12 ml of diisopropylamine were dissolved in 24 ml THF and treated dropwise, at 0° C., with 3.2 ml of butyl lithium (2.5M). After 30 min. at 0° C., a solution of 0.6 g of (4,4-dimethyl-thiochroman-6-yl)-acetic acid in 4 ml of THF was dropped in. The reaction mixture was stirred at 0° C. for one hour then at room temperature for 30 min. After cooling back to 0° C., a solution of 0.5 ml of pentyl iodide in 2 ml THF was added dropwise. The mixture was kept at 0° C. for one hour then at room temperature for two hours. The mixture was quenched with the addition of 25 ml of water and the pH was adjusted to 2 with HCl 1N. The mixture was extracted with three portions of 25 ml of ether. The combined organic extracts were washed with two portions of 25 ml of water and one portion of 25 ml of saturated aqueous sodium chloride solution. The organic phase was dried over MgSO₄ and concentrated in vacuo. The crude product was purified by flash chromatography (SiO₂, 10% methanol/methylene chloride), yielding 0.65 g of a pale yellow oil. 1H NMR (CDCl₃): 7.27 (d, J=1.8 Hz, 1H), 7.04 (d, J=8.1 Hz, 1H), 6.99 (dd, J=8.1, 1.8 Hz, 1H), 3.46 (t, J=7.7 Hz, 1H), 3.05–2.95 (m, 2H), 2.15–1.95 (m, 3H), 1.85–1.60 (m, 1H), 1.32 (s, 3H), 1.31 (s, 3H), 1.35–1.20 (m, 6H), 0.86 (t, J=6.7 Hz, 3H).

In analogy to example 36.1., by using a corresponding alkyl halide or benzyl halide, the following compounds were synthesized:

36.2. (RS)-2-(4,4-Dimethyl-thiochroman-6-yl)-3-phenylpropanoic acid, 1H NMR (CDCl$_3$): 7.30–7.00 (m, 8H), 3.77 (t, J=7.7 Hz, 1H), 3.36 (dd, J=13.8,8.3 Hz, 1H), 3.05–2.90 (m, 3H), 1.95–1.90 (m, 2H), 1.29 (s, 3H), 1.22 (s, 3H).

36.3. (RS)-2-(4,4-Dimethyl-thiochroman-6-yl)-4-phenylbutanoic acid, 1H NMR (CDCl$_3$): 7.30–7.10 (m, 6H), 7.04 (d, J=8.1 Hz, 1H), 6.99 (dd, J=8.1, 1.8 Hz, 1H), 3.45 (t, J=7.7 Hz, 1H), 3.05–2.95 (m, 2H), 2.65–2.50 (m, 2H), 2.45–2.30 (m, 1H), 2.15–2.00 (m, 1H), 1.95–1.90 (m, 2H), 1.31 (s, 3H), 1.30 (s, 3H).

EXAMPLE 37

37.1. Preparation of (RS)-N-methoxy-N-methyl-2-(4,4-dimethyl-thiochroman-6-yl)-heptanoic Amide 0.44 g of (RS)-2-(4,4-dimethyl-thiochroman-6-yl)-heptanoic acid was dissolved in a mixture of 2.1 ml DMF/ 4.2 ml of methylene chloride, and 1.35 g of MeO(Me)NH.HCl was added followed by 2.47 ml of diisopropylethylamine and 0.53 g of 1-[3-(dimethylamino)propyl]-3-ethylcarbodiimide hydrochloride. The reaction mixture was stirred at room temperature for 4 hours, then the volatiles were removed in vacuo. The residue was taken up in 100 ml ethyl acetate and washed with one portion of 50 ml of water, one portion of 50 ml of 1N hydrochloric acid, one portion of 50 ml of saturated aqueous sodium bicarbonate solution and one portion of 50 ml of saturated aqueous sodium chloride solution. The organic phase was dried over MgSO$_4$ and concentrated in vacuo, giving 0.49 g of a yellow oil. The crude product was used without purification. 1H NMR (CDCl$_3$): 7.27 (d, J=1.8 Hz, 1H), 7.02 (d, J=8.1 Hz, 1H), 6.95 (dd, J=8.1, 1.8 Hz, 1H), 3.48 (s, 3H), 3.35–3.20 (m, 1H), 3.15 (s, 3H), 3.05–2.95 (m, 2H), 2.00–1.90 (m, 2H), 1.75–1.55 (m, 2H), 1.32 (s, 3H), 1.26 (s, 3H), 1.35–1.20 (m, 6H), 0.85 (t, J=6.9 Hz, 3H).

In analogy to example 37.1., the following compounds were synthesized:

37.2. (RS)-N-Methoxy-N-methyl-2-(4,4-dimethyl-thiochroman-6-yl)-3-phenylpropanoic acid, 1H NMR (CDCl$_3$): 7.30–6.95 (m, 8H), 4.25–4.15 (m, 1H), 3.40 (dd, J=13.5,8.3 Hz, 1H), 3.27 (br. s, 3H), 3.10 (s, 3H), 3.05–2.85 (m, 3H), 2.00–1.85 (m, 2H), 1.28 (s, 3H), 1.21 (s, 3H).

37.3. (RS)-N-Methoxy-N-methyl-2-(4,4-dimethyl-thiochroman-6-yl)-4-phenylbutanoic acid, 1H NMR (CDCl$_3$): 7.30–7.10 (m, 6H), 7.05–6.90 (m, 2H), 3.90–3.80 (m, 1H), 3.38 (br. s, 3H), 3.14 (s, 3H), 3.05–2.95 (m, 2H), 2.56 (t, J=7.7 Hz, 2H), 2.45–2.30 (m, 1H), 2.15–2.00 (m, 1H), 1.95–1.90 (m, 2H), 1.30 (s, 6H).

EXAMPLE 38

38.1. Preparation of (RS)-2-(4,4-dimethyl-thiochroman-6-yl)-heptanal 0.49 g of (RS)-N-methoxy-N-methyl-2-(4,4-dimethyl-thiochroman-6-yl)-heptanoic amide was dissolved in 5 ml THF and treated with 1.6 ml of 1M lithium aluminium hydride solution in THF at −40° C. The mixture was stirred at −40° C. for 30 min. then allowed to warm to room temperature over 1.5 hour. The mixture was cooled back to −40° C. and 3.5 ml of 20% aqueous KHSO$_4$ solution was added over 5 min. The mixture was stirred at room temperature for one hour. The reaction mixture was partitioned in 100 ml ethyl acetate/50 ml water and the phases were separated. The aqueous phase was extracted with three portions of 15 ml of ethyl acetate. The combined organic extracts were washed with one portion of 25 ml of water, one portion of 25 ml of 1 N hydrochloric acid, one portion of 25 ml of saturated aqueous sodium bicarbonate solution and one portion of 25 ml of saturated aqueous sodium chloride solution. The organic phase was dried over MgSO$_4$ and concentrated in vacuo, giving 0.35 g of the titled compound which was used without purification. 1H NMR (CDCl$_3$): 9.61 (d, J=2.2 Hz, 1H), 7.13 (d, J=2.0 Hz, 1H), 7.08 (d, J=8.1 Hz, 1H), 6.86 (dd, J=8.1, 2.0 Hz, 1H), 3.45–3.35 (m, 1H), 3.05–3.00 (m, 2H), 2.10–1.90 (m, 3H), 1.70–1.50 (m, 1H), 1.32 (s, 6H), 1.35–1.20 (m, 6H), 0.86 (br.t, J=6.7 Hz, 3H).

In analogy to example 38.1., the following compounds were synthesized:

38.2. (RS)-2-(4,4-Dimethyl-thiochroman-6-yl)-3-phenylpropanal, 1H NMR (CDCl$_3$): 9.72 (d, J=1.5 Hz, 1H), 7.25–7.00 (m, 6H), 6.97 (d, J=2.0 Hz, 1H), 6.80 (dd, J=8.1, 2.0 Hz, 1H), 3.74 (td, J=6.6, 1.5 Hz, 1H), 3.44 (dd, J=13.9, 6.5 Hz, 1H), 3.05–2.95 (m, 2H), 2.90 (dd, J=13.9, 8.0 Hz, 1H), 1.95–1.85 (m, 2H), 1.27 (s, 3H), 1.20 (s, 3H).

38.3. (RS)-2-(4,4-Dimethyl-thiochroman-6-yl)-4-phenylbutanal, 1H NMR (CDCl$_3$): 9.62 (d, J=1.8 Hz, 1H), 7.35–7.05 (m, 7H), 6.86 (dd, J=8.1, 2.0 Hz, 1H), 3.41 (td, J=8.3, 1.7 Hz, 1H), 3.10–3.00 (m, 2H), 2.70–2.30 (m, 3H), 2.10–1.90 (m, 3H), 1.33 (s, 3H), 1.32 (s, 3H).

EXAMPLE 39

39.1. Preparation of (RS)-(E)-methyl 4-[3-(4,4-dimethyl-thiochroman-6-yl)-oct-1-enyl]-benzoate 0.51 g of methyl 4-(diethoxyphosphorylmethyl)-benzoate were dissolved in 7.5 ml THF and treated, at −20° C., with 1.8 ml of a 1M solution of lithium bis(trimethylsilyl)amide in hexane. After 15 min. at −20° C., a solution of 350 mg of (RS)-2-(4,4-dimethyl-thiochroman-6-yl)-heptanal in 7.5 ml THF was added. The reaction mixture was stirred at room temperature for 1.5 hour. The mixture quenched by the addition of 10 ml of water and the resulting mixture was partitioned in 25 ml ethyl acetate/15 ml sat. aq. sodium chloride solution. The phases were separated and the organic phase was dried over MgSO$_4$. The solvent was removed in vacuo and the crude product was purified by flash chromatography (SiO$_2$, 10% ethyl acetate/hexanes), giving 200 mg of the corresponding ester. 1H NMR (CDCl$_3$): 7.94 (d, J=8.5 Hz, 2H), 7.38 (d, J=8.5 Hz, 2H), 7.19 (d, J=1.8 Hz, 1H), 7.03 (d, J=8.1 Hz, 1H), 6.91 (dd, J=8.1, 1.8 Hz, 1H), 6.45 (d, J=15.9 Hz, 1H), 6.38 (d, J=15.9 Hz, 1H), 3.90 (s, 3H), 3.30 (m, 1H), 3.05–3.00 (m, 2H), 2.00–1.90 (m, 2H), 1.85–1.75 (m, 2H), 1.33 (s, 6H), 1.40–1.30 (m, 6H), 0.86 (t, J=6.5 HZ, 3H).

In analogy to example 39.1., the following compounds were synthesized:

39.2. (RS)-(E)-Methyl 4-[3-(4,4-dimethyl-thiochroman-6-yl)-4-phenylbut-1-enyl]-benzoate, 1H NMR (CDCl$_3$): 7.94 (d, J=8.4 Hz, 2H), 7.34 (d, J=8.3 Hz, 2H), 7.25–7.00 (m, 7H), 6.92 (dd, J=8.1, 1.9 Hz, 1H), 6.52 (dd, J=15.9, 7.3 Hz, 1H), 6.33 (d, J=15.9 Hz, 1H), 3.90 (s, 3H), 3.65 (m, 1H), 3.20–2.95 (m, 4H), 2.00–1.90 (m, 2H), 1.28 (s, 3H), 1.21 (s, 3H).

39.3. (RS)-(E)-Methyl 4-[3-(4,4-dimethyl-thiochroman-6-yl)-5-phenylpent-1-enyl]-benzoate, 1H NMR (CDCl$_3$): 7.95 (d, J=8.6 Hz, 2H), 7.38 (d, J=8.5 Hz, 2H), 7.35–7.25 (m, 2H), 7.25–7.10 (m, 4H), 7.05 (d, J=8.1 Hz, 1H), 6.93 (dd, J=8.1, 1.9 Hz, 1H), 6.47 (d, J=15.9 Hz, 1H), 6.39 (d, J=16.0 Hz, 1H), 3.89 (s, 3H), 3.36 (m, 1H), 3.05–2.95 (m, 2H), 2.60 (t, J=7.8 Hz, 2H), 2.2–2.05 (m, 2H), 2.00–1.90 (m, 2H), 1.34 (s, 3H), 1.32 (s, 3H).

EXAMPLE 40

40.1. Preparation of (RS)-(E)-4-[3-(4,4-dimethyl-thiochroman-6-yl)-oct-1-enyl]-benzoic Acid 200 mg of (RS)-(E)-methyl 4-[3-(4,4-dimethyl-thiochroman-6-yl)-oct-1-enyl]-benzoate were dissolved in 10 ml THF/3 ml water/3 ml methanol and 200 mg of lithium hydroxide hydrate were added. The mixture was stirred at room temperature 4 hours. The mixture was diluted with 10 ml water and acidified to pH 2 with 1N hydrochloric. The resulting suspension was taken in 50 ml ether and the phases were separated. The aqueous phase was extracted with three portions of 25 ml ether. The combined extracts were dried over $MgSO_4$. The solvent was removed in vacuo and the crude product was purified by flash chromatography (SiO2, 10% methanol/methylene chloride) followed by recrystalization from hexanes, yielding 185 mg of product as white solid. M.p. 146–146.5° C.

In analogy to example 40.1., the following compounds were synthesized:

40.2. (RS)-(E)-4-[3-(4,4-Dimethyl-thiochroman-6-yl)-4-phenylbut-1-enyl]-benzoic acid, as a white solid, m.p. 183–184° C.

40.3. (RS)-(E)-4-[3-(4,4-Dimethyl-thiochroman-6-yl)-5-phenylpent-1-enyl]-benzoic acid, as a white solid, m.p. 63–76° C.

EXAMPLE 41

Preparation of ethyl 4-nitrophenylacetate 10 g of 4-nitrophenylacetic acid dissolved in 100 ml of ethanol were treated with 3 ml of concentrated sulfuric acid. The mixture was heated to reflux for 18 hours. After cooling to room temperature, the mixture was neutralized with 2 N sodium hydroxide solution then was extracted with two portions of 200 ml ethyl acetate. The combined extracts were washed with one portion of 100 ml of saturated aqueous sodium chloride solution then dried over $MgSO_4$ and concentrated in vacuo, yielding 11.5 g of a white solid that was used without purification. 1H NMR ($CDCl_3$): 8.19 (d, J=8.8 Hz, 2H), 7.47 (d, J=8.8 Hz, 2H), 4.18 (q, J=7.1 Hz, 2H), 3.73 (s, 2H), 1.27 (t, J=7.1 Hz, 3H).

EXAMPLE 42

Preparation of (RS)-ethyl 2-(4-nitrophenyl)-heptanoate 1 g of ethyl 4-nitrophenylacetate dissolved in 20 ml of dimethylformamide was treated with 3.12 g of cesium carbonate and 0.68 ml of iodopentane. The mixture was stirred at room temperature for 18 hours. The mixture was poured onto 50 ml of iced water and the resulting mixture was extracted with two portions of 50 ml ether. The combined organic extracts were dried over $MgSO_4$ and concentrated in vacuo. The product was purified by flash chromatography ($SiO_2$, 20% ethyl acetate/hexanes), yielding a pale yellow oil. 1H NMR ($CDCl_3$): 8.18 (d, J=8.6 Hz, 2H), 7.49 (d, J=8.8 Hz, 2H), 4.25–4.00 (m, 2H), 3.64 (t, J=7.7 Hz, 1H), 2.20–2.00 (m, 1H), 1.85–1.70 (m, 1H), 1.45–1.15 (m, 6H), 1.22 (t, J=7.2 Hz, 3H), 0.90–0.80 (m, 3H).

EXAMPLE 43

Preparation of (RS)-ethyl 2-(4-aminophenyl)-heptanoate 12 g of (RS)-ethyl 2-(4-nitrophenyl)-heptanoate dissolved in 100 ml of ethanol was treated with 2.4 g of 10% palladium on carbon. The mixture was stirred at room temperature for 18 hours under 40 psi of hydrogen. The mixture was filtered on a pad of Celite and concentrated in vacuo. The product was purified by flash chromatography ($SiO_2$, 25% ethyl acetate/hexanes), yielding 10.4 g of a pale yellow oil. 1H NMR ($CDCl_3$): 7.10 (d, J=8.4 Hz, 2H), 6.63 (d, J=8.5 Hz, 2H), 4.20–4.00 (m, 2H), 3.61 (br. s, 2H), 3.40 (t, J=7.7 Hz, 1H), 2.05–1.90 (m, 1H), 1.75–1.60 (m, 1H), 1.30–1.15 (m, 6H), 1.20 (t, J=7.2 Hz, 3H), 0.85 (t, J=6.7 Hz, 3H).

EXAMPLE 44

Preparation of (RS)-ethyl 2-[4-(3,3-dimethylacrylamido)-phenyl]-heptanoate 10.4 g of (RS)-ethyl 2-(4-aminophenyl)-heptanoate dissolved in 100 ml of chloroform was treated dropwise with 4.64 ml of 3,3-dimethylacryloyl chloride. The mixture was heated to reflux for 6 hours. After cooling to room temperature, 100 ml of water were added. The phases were separated and the aqueous phase was extracted with two portions of 50 ml of chloroform. The combined organic extracts were washed with two portions of 100 ml of saturated aqueous sodium bicarbonate solution and one portion of 100 ml of saturated aqueous sodium chloride solution. The organic phase was dried over $MgSO_4$ and concentrated in vacuo. The product was used without purification. 1H NMR ($CDCl_3$): 7.48 (br. d, J=8.4 Hz, 2H), 7.39 (br. s, 1H), 7.24 (d, J=8.5 Hz, 2H), 5.71 (br. s, 1H), 4.20–4.00 (m, 2H), 3.48 (t, J=7.7 Hz, 1H), 2.21 (br. s, 3H), 2.15–1.95 (m, 1H), 1.87 (s, 3H), 1.80–1.65 (m, 1H), 1.35–1.15 (m, 6H), 1.20 (t, J=7.1 Hz, 3H), 0.85 (t, J=6.7 Hz, 3H).

EXAMPLE 45

Preparation of (RS)-ethyl 2-(4,4-dimethyl-2-oxo-1,2,3,4-tetrahydroquinolin-6-yl)-heptanoate 1 g of (RS)-ethyl 2-[4-(3,3-dimethylacrylamido)-phenyl]-heptanoate was dissolved in 10 ml of methylene chloride and treated with 1.2 g of aluminium chloride. The mixture was heated to reflux for 6 hours. The mixture was poured onto 25 ml of iced water and then was extracted with two portions of 25 ml of methylene chloride. The combined extracts were washed with two portion of 25 ml of saturated aqueous sodium bicarbonate solution and one portion of 25 ml of saturated aqueous sodium chloride solution. The organic phase was dried over $MgSO_4$ and concentrated in vacuo. The product was purified by flash chromatography ($SiO_2$, 20% ethyl acetate/hexanes). 1H NMR ($CDCl_3$): 8.92 (br. s, 1H), 7.21 (d, J=1.9 Hz, 1H), 7.13 (dd, J=8.1, 1.9 Hz, 1H), 6.78 (d, J=8.1 Hz, 1H), 4.20–4.00 (m, 2H), 3.48 (t, J=7.7 Hz, 1H), 2.48 (s, 2H), 2.10–1.90 (m, 1H), 1.80–1.65 (m, 1H), 1.35–1.15 (m, 6H), 1.33 (s, 3H), 1.32 (s, 3H), 1.22 (t, J=7.1 Hz, 3H), 0.86 (t, J=6.6 Hz, 3H).

EXAMPLE 46

Preparation of (RS)-2-(4,4-dimethyl-1,2,3,4-tetrahydroquinolin-6-yl)-heptanol 7 g of (RS)-ethyl 2-(4,4-dimethyl-2-oxo-1,2,3,4-tetrahydroquinolin-6-yl)-heptanoate were dissolved in 70 ml of toluene and treated, at 0° C., with 4.4 ml of a 10M solution of borane-dimethyl sulfide complex solution in toluene. The mixture was heated to 90° C. for 7 hours. After cooling to room temperature, the mixture was quenched by slow addition of 50 ml of 10% aqueous sodium carbonate solution. The mixture was stirred at room temperature for 30 min. and the phases were separated. The aqueous phase was extracted with two portion of 50 ml of ethyl acetate. The combined extracts were dried over $MgSO_4$ and concentrated in vacuo. The product was purified by flash chromatography ($SiO_2$, 25% ethyl acetate/hexanes). 1H NMR ($CDCl_3$): 6.97 (d, J=2.0 Hz, 1H), 6.76 (dd, J=8.2, 2.0 Hz, 1H), 6.41 (d, J=8.2 Hz, 1H), 3.65 (dd, J=10.6, 5.9 Hz, 1H), 3.57 (dd, J=10.6, 7.9 Hz, 1H), 3.30–3.20 (m, 2H), 2.65–2.55 (m, 1H), 1.80–1.70 (m, 2H), 1.65–1.40 (m, 2H), 1.30–1.15 (m, 6H), 1.27 (s, 6H), 0.86 (t, J=6.6 Hz, 3H).

EXAMPLE 47

Preparation of (RS)-2-(N-ethyl-4,4-dimethyl-1,2,3,4-tetrahydroquinolin-6-yl)-heptanol 1.5 g of (RS)-2-(4,4-dimethyl-1,2,3,4-tetrahydroquinolin-6-yl)-heptanol, dissolved in 25 ml of methylene chloride, were treated at 0° C. with 0.46 ml of acetaldehyde and 3.46 g of sodium triacetoxyborohydride, then 0.62 ml of acetic acid was added. The mixture was stirred at room temperature for 18 hours. The reaction mixture was quenched with the addition of one portion of 25 ml of water and then, was extracted with two portions of 25 ml of methylene chloride. The combined organic phases were dried over $MgSO_4$ and concentrated in vacuo. The product was purified by flash chromatography ($SiO_2$, 25% ethyl acetate/hexanes). 1H NMR ($CDCl_3$): 6.98 (d, J=2.2 Hz, 1H), 6.85 (dd, J=8.4, 2.2 Hz, 1H), 6.56 (d, J=8.4 Hz, 1H), 3.75–3.55 (m, 2H), 3.33 (q, J=7.1 Hz, 2H), 3.30–3.20 (m, 2H), 2.70–2.55 (m, 1H), 1.80–1.70 (m, 2H), 1.70–1.45 (m, 2H), 1.45–1.20 (m, 6H), 1.26 (s, 6H), 1.14 (t, J=7.1 Hz, 3H), 0.84 (t, J=6.5 Hz, 3H).

EXAMPLE 48

Preparation of (RS)-4-[2-(N-ethyl-4,4-dimethyl-1,2,3,4-tetrahydroquinolin-6-yl)-heptyloxy]-benzoic Acid 1 g of (RS)-2-(N-ethyl-4,4-dimethyl-1,2,3,4-tetrahydroquinolin-6-yl)-heptanol dissolved in 20 ml THF were treated with 950 mg of triphenylphosphine, 550 mg of methyl 4-hydroxybenzoate and 0.57 ml of diethyl azodicarboxylate. The reaction mixture was heated to reflux for 6 hours. The mixture was diluted with 100 ml of ether and washed with two portions of 25 ml of water and one portion of 25 ml of sat. aq. sodium chloride solution. The organic phase was dried over $MgSO_4$. The solvents were removed in vacuo and the resulting yellow oil was purified by flash chromatography ($SiO_2$, 3% ethyl acetate/hexanes), giving 670 mg (RS)-methyl 4-[2-(N-ethyl-4,4-dimethyl-1,2,3,4-tetrahydroquinolin-6-yl)-heptyloxy]-benzoate as a pale yellow oil. The ester (670 mg), dissolved in 5 ml THF/5 ml $H_2O$/5 ml methanol, was treated with 260 mg of lithium hydroxide hydrate. The mixture was stirred at 40° C. for 6 hours. The mixture was diluted with 5 ml water and acidified to pH 2 with 1N hydrochloric. The resulting suspension was taken in 20 ml ether and the phases were separated. The aqueous phase was extracted with three portions of 10 ml ether. The combined extracts were dried over $MgSO_4$. The solvent was removed in vacuo and the crude product was purified by preparative tlc (10% methanol/methylene chloride), yielding 320 mg of a pale yellow oil. 1H NMR ($CDCl_3$): 8.01 (d, J=9.0 HZ, 2H), 6.98 (d, J=2.1 Hz, 1H), 6.95–6.85 (m, 3H), 6.52 (d, J=8.4 Hz, 1H), 4.64 (quint, J=5.8 Hz, 1H), 3.32 (q, J=7.1 Hz, 2H), 3.25–3.15 (m, 2H), 2.88 (dd, J=14.1, 5.9 Hz, 1H), 2.78 (dd, J=14.1, 5.9 Hz, 1H), 1.80–1.65 (m, 4H), 1.55–1.25 (m, 6H), 1.24 (s, 3H), 1.18 (s, 3H), 1.11 (t, J=7.1 Hz, 3H), 0.86 (t, J=6.7 Hz, 3H).

EXAMPLE 49

Preparation of (RS)-2-(4,4-dimethyl-thiochroman-6-yl)-heptanol 0.32 g of (RS)-2-(4,4-dimethyl-thiochroman-6-yl)-heptanoic acid were dissolved in 5 ml THF and treated dropwise, at 0° C., with 5.23 ml of 1M $BH_3$.THF in THF. The mixture was stirred at 0° C. for two hours and then was quenched at 0° C. with careful addition of one portion of 5 ml of 3N HCl. The mixture was stirred at room temperature for 30 min. then was extracted with three portion of 25 ml of ethyl acetate. The combined organic extracts were dried over $MgSO_4$ and concentrated in vacuo, giving a yellow oil. The product was purified by flash chromatography ($SiO_2$, 10% ethyl acetate/hexanes), yielding 0.31 g of a colorless oil. 1H NMR ($CDCl_3$): 7.10 (d, J=1.9 Hz, 1H), 6.97 (d, J=8.1 Hz, 1H), 6.81 (dd, J=8.1, 1.9 Hz, 1H), 3.65 (dd, J=10.7, 5.9 Hz, 1H), 3.57 (dd, J=10.7, 8.4 Hz, 1H), 3.00–2.90 (m, 2H), 2.65–2.55 (m, 1H), 1.95–1.85 (m, 2H), 1.65–1.35 (m, 2H), 1.26 (s, 6H), 1.25–1.05 (m, 6H), 0.87 (t, J=7.6 Hz, 3H).

EXAMPLE 50

Preparation of (RS)-methyl 4-[2-(4,4-dimethyl-thiochroman-6-yl)-heptyloxy]-benzoate 0.25 g of (RS)-2-(4,4-dimethyl-thiochroman-6-yl)-heptanol dissolved in 15 ml THF were treated with 250 mg of triphenylphosphine, 150 mg of methyl 4-hydroxybenzoate and 0.15 ml of diethyl azodicarboxylate. The reaction mixture was heated to reflux for 6 hours. The mixture was diluted with 50 ml of ether and washed with two portions of 15 ml of water and one portion of 15 ml of sat. aq. sodium chloride solution. The organic phase was dried over $MgSO_4$. The solvents were removed in vacuo and the resulting yellow oil was purified by flash chromatography ($SiO_2$, 3% ethyl acetate/hexanes), giving 280 mg of (RS)-methyl 4-[2-(4,4-dimethyl-thiochroman-6-yl)-heptyloxy]-benzoate as a pale yellow oil. 1H NMR ($CDCl_3$): 7.95 (d, J=8.9 Hz, 2H), 7.21 (d, J=1.9 Hz, 1H), 7.03 (d, J=8.1 Hz, 1H), 6.91 (dd, J=8.1, 1.9 Hz, 1H), 6.87 (d, J=8.9 Hz, 2H), 4.10–4.00 (m, 2H), 3.87 (s, 3H), 3.05–2.90 (m, 3H), 2.00–1.80 (m, 3H), 1.70–1.60 (m, 1H), 1.32 (s, 3H), 1.31 (s, 3H), 1.35–1.15 (m, 6H), 0.90–0.80 (m, 3H).

EXAMPLE 51

Preparation of (RS)-4-[2-(4,4-dimethyl-thiochroman-6-yl)-heptyloxy]-benzoic Acid 140 mg of (RS)-methyl 4-[2-(4,4-dimethyl-thiochroman-6-yl)-heptyloxy]-benzoate, dissolved in 20 ml THF/5 ml $H_2O$/5 ml methanol, was treated with 200 mg of lithium hydroxide hydrate. The mixture was stirred at 40° C. for 6 hours. The mixture was diluted with 5 ml water and acidified to pH 2 with 1N hydrochloric. The resulting suspension was taken in 20 ml ether and the phases were separated. The aqueous phase was extracted with three portions of 10 ml ether. The combined extracts were dried over $MgSO_4$. The solvent was removed in vacuo and the crude product was purified by flash chromatography (10% methanol/methylene chloride), yielding a colorless oil. Trituration in hexanes provided a white solid, m.p. 168–169° C.

EXAMPLE 52

Preparation of (RS)-4-[2-(4,4-dimethyl-1-oxide-thiochroman-6-yl)-heptyloxy]-benzoic Acid 140 mg of (RS)-methyl 4-[2-(4,4-dimethyl-thiochroman-6-yl)-heptyloxy]-benzoate, dissolved in 5 ml THF/12 ml $H_2O$/13 ml methanol, was treated with 122 mg of "Oxone". The mixture was stirred at room temperature for 20 hours. The mixture was diluted with 25 ml water and was taken in 20 ml ethyl acetate and the phases were separated. The aqueous phase was extracted with three portions of 10 ml ethyl acetate. The combined extracts were dried over $MgSO_4$. The solvent was removed in vacuo and the crude product was purified by flash chromatography (10% methanol/methylene chloride), yielding 110 mg of a colorless oil.

110 mg of (RS)-methyl 4-[2-(4,4-dimethyl-1-oxide-thiochroman-6-yl)-heptyloxy]-benzoate, dissolved in 20 ml THF/5 ml $H_2O$/5 ml methanol, was treated with 200 mg of lithium hydroxide hydrate. The mixture was stirred at 40° C. for 6 hours. The mixture was diluted with 5 ml water and acidified to pH 2 with 1N hydrochloric. The resulting suspension was taken in 20 ml ether and the phases were separated. The aqueous phase was extracted with three portions of 10 ml ether. The combined extracts were dried over $MgSO_4$. The solvent was removed in vacuo and the crude product was purified by flash chromatography (10% methanol/methylene chloride), yielding a colorless oil. Trituration in acetonitrile provided 90 mg of white solid, m.p. 146–146.5° C.

EXAMPLE 53
Preparation of (RS)-(E)-4-[3-(4,4-dimethyl-1,1-dioxide-thiochroman-6-yl)-oct-1-enyl]-benzoic Acid 230 mg of (RS)-(E)-methyl 4-[3-(4,4-dimethyl-thiochroman-6-yl)-oct-1-enyl]-benzoate, dissolved in 15 ml THF/18 ml $H_2O$/20 ml methanol, was treated with 1.86 g of "Oxone". The mixture was stirred at room temperature for 4 hours. The mixture was diluted with 25 ml water and was taken in 50 ml ethyl acetate and the phases were separated. The aqueous phase was extracted with three portions of 20 ml ethyl acetate. The combined extracts were dried over $MgSO_4$. The solvent was removed in vacuo and the crude product was purified by flash chromatography (10% ethyl acetate/hexanes), yielding 190 mg of a colorless oil.

190 mg of (RS)-(E)-methyl 4-[3-(4,4-dimethyl-1,1-dioxide-thiochroman-6-yl)-oct-1-enyl]-benzoate, dissolved in 20 ml THF/5 ml $H_2O$/5 ml methanol, was treated with 200 mg of lithium hydroxide hydrate. The mixture was stirred at 40° C. for 6 hours. The mixture was diluted with 5 ml water and acidified to pH 2 with 1N hydrochloric. The resulting suspension was taken in 20 ml ether and the phases were separated. The aqueous phase was extracted with three portions of 10 ml ether. The combined extracts were dried over $MgSO_4$. The solvent was removed in vacuo and the crude product was purified trituration in hexanes, yielding a pale yellow solid, m.p. 195–206° C.

EXAMPLE 54
Preparation of (2,2,4,4-tetramethyl-chroman-6-yl)-acetic Acid 5.03 g of 6-acetyl-2,2,4,4-tetramethylchromane (U.S. Pat. No. 5,006,550) were dissolved in 2.67 ml of morpholine. 0.69 g of sulfur ($S_8$) were added, followed by 91 mg of p-toluenesulfonic acid hydrate. The mixture was heated to reflux for 22 hours. After cooling, 12 ml of methanol were added. The mixture was stirred at 0° C. for two hours then, the volatiles were removed in vacuo, giving a dark brown oil which was purified by flash chromatography ($SiO_2$, 10% ethyl acetate/hexanes), yielding 2.9 g of a golden oil.

The thioamide (2.9 g) was dissolved in 24 ml glacial acetic acid/3.5 ml water and then was treated with 2.5 ml of concentrated sulfuric acid. The mixture was heated to reflux for 14 hours. After cooling, the reaction mixture was poured onto 300 ml of iced water and then was extracted with three portions of 100 ml of ethyl acetate. The combined extracts were washed with one portion of 100 ml of water and one portion of 100 ml of saturated aqueous sodium chloride solution. The organic phase was dried over $MgSO_4$ and concentrated in vacuo, giving a black solid. The crude product was purified by flash chromatography ($SiO_2$, 20% ethyl acetate/hexanes), yielding a beige solid, which was recrystallized from hexanes (1.9 g). 1H NMR ($CDCl_3$): 7.16 (d, J=2.2 Hz, 1H), 6.99 (dd, J=8.3, 2.2 Hz, 1H), 6.75 (d, J=8.3 Hz, 1H), 3.57 (s, 2H), 1.82 (s, 2H), 1.34 (s, 6H), 1.33 (s, 6H).

EXAMPLE 55
Preparation of (RS)-2-(2,2,4,4-tetramethyl-chroman-6-yl)-heptanoic Acid 2.55 ml of diisopropylamine were dissolved in 60 ml THF and treated dropwise, at 0° C., with 7.2 ml of butyl lithium (2.5M). After 30 min. at 0° C., a solution of 1.8 g of (2,2,4,4-tetramethyl-chroman-6-yl)-acetic acid in 8 ml of THF was dropped in. The reaction mixture was stirred at 0° C. for one hour then at room temperature for 30 min. After cooling back to 0° C., a solution of 1.42 ml of pentyl iodide in 4 ml THF was added dropwise. The mixture was kept at 0° C. for one hour then at room temperature for two hours. The mixture was quenched with the addition of 50 ml of water and the pH was adjusted to 2 with HCl 1N. The mixture was extracted with three portions of 50 ml of ether. The combined organic extracts were washed with two portions of 50 ml of water and one portion of 50 ml of saturated aqueous sodium chloride solution. The organic phase was dried over $MgSO_4$ and concentrated in vacuo. The crude product was purified by flash chromatography ($SiO_2$, 20% ethyl acetate/hexanes), yielding 1.2 g of a pale yellow oil. 1H NMR ($CDCl_3$): 7.17 (d, J=2.2 Hz, 1H), 7.03 (dd, J=8.4, 2.2 Hz, 1H), 6.73 (d, J=8.4 Hz, 1H), 3.45 (t, J=7.7 Hz, 1H), 2.10–1.90 (m, 1H), 1.81 (s, 2H), 1.80–1.65 (m, 1H), 1.33 (s, 6H), 1.32 (s, 6H), 1.40–1.20 (m, 6H), 0.85 (t, J=6.9 Hz, 3H).

EXAMPLE 56
Preparation of (RS)-2-(2,2,4,4-tetramethyl-chroman-6-yl)-heptanol 0.8 g of (RS)-2-(2,2,4,4-tetramethyl-chroman-6-yl)-heptanoic acid were dissolved in 15 ml THF and treated dropwise, at 0° C., with 12.3 ml of 1M $BH_3$.THF in THF. The mixture was stirred at 0° C. for two hours and then was quenched at 0° C. with careful addition of one portion of 15 ml of 3N HCl. The mixture was stirred at room temperature for 30 min. then was extracted with three portion of 75 ml of ethyl acetate. The combined organic extracts were dried over $MgSO_4$ and concentrated in vacuo, giving a yellow oil. The product was purified by flash chromatography ($SiO_2$, 10% ethyl acetate/hexanes), yielding 0.5 g of a pale yellow oil. 1H NMR ($CDCl_3$): 7.06 (d, J=2.2 Hz, 1H), 6.90 (dd, J=8.3, 2.2 Hz, 1H), 6.75 (d, J=8.3 Hz, 1H), 3.72 (dd, J=10.7, 5.7 Hz, 1H), 3.64 (dd, J=10.7, 8.0 Hz, 1H), 2.75–2.65 (m, 1H), 1.82 (s, 2H), 1.70–1.45 (m, 2H), 1.35 (s, 6H), 1.34 (s, 6H), 1.30–1.15 (m, 6H), 0.83 (t, J=6.9 Hz, 3H).

EXAMPLE 57
Preparation of (RS)-methyl 4-[2-(2,2,4,4-tetramethyl-chroman-6-yl)-heptyloxy]-benzoate 0.5 g of (RS)-2-(2,2,4,4-tetramethyl-chroman-6-yl)-heptanol dissolved in 35 ml THF were treated with 480 mg of triphenylphosphine, 275 mg of methyl 4-hydroxybenzoate and 0.28 ml of diethyl azodicarboxylate. The reaction mixture was heated to reflux for 6 hours. The mixture was diluted with 100 ml of ether and washed with two portions of 30 ml of water and one portion of 30 ml of sat. aq. sodium chloride solution. The organic phase was dried over $MgSO_4$. The solvents were removed in vacuo and the resulting yellow oil was purified by flash chromatography ($SiO_2$, 10% ethyl acetate/hexanes), giving 550 mg of (RS)-methyl 4-[2-(2,2,4,4-tetramethyl-chroman-6-yl)-heptyloxy]-benzoate as a pale yellow oil. 1H NMR ($CDCl_3$): 7.95 (d, J=8.8 Hz, 2H), 7.10 (d, J=2.2 Hz, 1H), 6.94 (dd, J=8.3, 2.2 Hz, 1H), 6.88 (d, J=8.8 Hz, 2H), 6.73 (d, J=8.3 Hz, 1H), 4.20–4.00 (m, 2H), 3.87 (s, 3H), 3.05–2.90 (m, 1H), 1.95–1.85 (m, 1H), 1.82 (s, 2H), 1.70–1.60 (m, 1H), 1.34 (s, 6H), 1.33 (s, 3H), 1.32 (s, 3H), 1.30–1.20 (m, 6H), 0.90–0.80 (m, 3H).

EXAMPLE 58
Preparation of (RS)-4-[2-(2,2,4,4-tetramethyl-chroman-6-yl)-heptyloxy]-benzoic Acid 550 mg of (RS)-methyl 4-[2-(2,2,4,4-tetramethyl-chroman-6-yl)-heptyloxy]-benzoate, dissolved in 40 ml THF/10 ml H$_2$O/10 ml methanol, was treated with 600 mg of lithium hydroxide hydrate. The mixture was stirred at 40° C. for 6 hours. The mixture was diluted with 10 ml water and acidified to pH 2 with 1N hydrochloric. The resulting suspension was taken in 40 ml ether and the phases were separated. The aqueous phase was extracted with three portions of 20 ml ether. The combined extracts were dried over MgSO$_4$. The solvent was removed in vacuo and the crude product was purified by trituration in acetonitrile, providing 510 mg of a pale yellow solid, m.p. 94–96° C.

EXAMPLE 59

Effects of RAR Selective Retinoids on Repair of Alveoli in Elastase-Induced Emphysema RAR selective agonists were evaluated for its effects on alveolar repair in the rat model of elastase-induced emphysema in rats (D. Massaro et al. *Nature Medicine* (1997, 3, 675). Animals were divided into treatment groups of approximately eight. Lung inflammation and alveolar damage was induced in male Sprague Dawley rats by a single instillation of pancreatic elastase(porcine derived, Calbiochem) 2 U/gram body mass. Three weeks post injury, all-trans retinoic acid or RAR agonist was dissolved in dimethylsulfoxide (20 mg/ml) and stored at −20 C. Fresh working stocks were prepared daily by dilution in PBS to a final concentration of 2 mg/ml. Animals were dosed once daily with the retinoid by intraperitoneal injection or orally, starting 21 days post injury. Control groups were challenged with elastase and 21 days later treated with Vehicle (DMSO/PBS) for 14 days. Animals were sacrificed 24 hours after the last dose by exsanguination under deep anesthesia.

The lungs were inflated with 10% neutral buffered formalin by intratracheal instillation at a constant rate (1 ml/gram body mass/min). The lung was excised and immersed in fixative for 24 hours prior to processing. Standard methods were used to prepare 5 um paraffin sections. Sections were stained with Hematoxylin and Eosin (H%E). Computerized Morphometric analysis was performed to determine the average alveolar size and alveolar number (Table 1).

TABLE 1

Data is given for (RS)-(E)-4-[3-(5,5,8,8-tetramethyl-5,6,7,8-tetrahydronaphthalen-2-yl)-oct-1-enyl]-benzoic acid;

| Dose [mg/kg] | | % repair area |
|---|---|---|
| 0.03 | p.o. | 32 |
| 0.01 | p.o. | 49 |
| 0.003 | p.o. | 53 |

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A compound selected from the group consisting of compounds of formula I

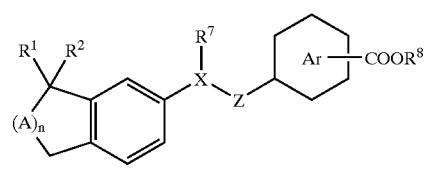

wherein
   $R^1$ and $R^2$ independently of each other are hydrogen or lower alkyl;
   A is $C(R^5R^6)$,
   n is an integer 1,2 or 3,
   B is $C(R^3R^4)$;
   X is —$CR^7$—;
   $R^3$, $R^4$, $R^5$ and $R^6$ independently of each other are hydrogen or lower alkyl;
   $R^7$ and $R^{7'}$ independently of each other are hydrogen, alkyl, alkenyl, alkoxy, alkoxyalkyl, substituted alkyl, phenyloxy or substituted phenyloxy, or $R^7$ and $R^{7'}$ together are —$(CH_2)_p$—, where p is 2–6,
   Z is —$CH_2O$—;
   Ar is phenyl; and
   $R^8$ is hydrogen, lower alkyl or benzyl;
and pharmaceutically acceptable salts of carboxylic acids of formula I.

2. The compound of claim 1, wherein the compound is 4-[2-(5,5,8,8-tetramethyl-5,6,7,8-tetrahydronaphthalen-2-yl)-ethyloxy]-benzoic acid.

3. The compound of claim 1, wherein the compound is (R)-4-[2-(5,5,8,8-tetramethyl-5,6,7,8-tetrahydronaphthalen-2-yl)-heptyloxy]-benzoic acid.

4. The compound of claim 1, wherein the compound is (S)-4-[2-(5,5,8,8-tetramethyl-5,6,7,8-tetrahydronaphthalen-2-yl)-heptyloxy]-benzoic acid.

5. The compound of claim 1, wherein the compound is 4-[2-methyl-2-(5,5,8,8-tetramethyl-5,6,7,8-tetrahydronaphthalen-2-yl)-propyloxy]-benzoic acid.

6. The compound of claim 1, wherein the compound is 4-[2-propyl-2-(5,5,8,8-tetramethyl-5,6,7,8-tetrahydronaphthalen-2-yl)-pentyloxy]-benzoic acid.

7. The compound of claim 1, wherein the compound is 4-[1-(5,5,8,8-(tetramethyl-5,6,7,8-tetrahydronaphthalen-2-yl)-cyclopentylmethoxy]-benzoic acid.

8. The compound of claim 1, wherein the compound is 4-[1-(5,5,8,8-tetramethyl-5,6,7,8-tetrahydronaphthalen-2-yl)-cyclohexylmethoxy]-benzoic acid.

9. The compound of claim 1, wherein the compound is (RS)-4-[3-(pyridin-2-yl)-2-(5,5,8,8-tetramethyl-5,6,7,8-tetrahydronaphthalen-2-yl)-propyloxy]-benzoic acid.

10. The compound of claim 1, wherein the compound is (RS)-4-[3-(pyridin-3-yl)-2-(5,5,8,8-tetramethyl-5,6,7,8-tetrahydronaphthalen-2-yl)propyloxy]-benzoic acid.

11. The compound of claim 1, wherein the compound is (RS)-4-[3-(pyridin-4-yl)-2-(5,5,8,8-tetramethyl-5,6,7,8-tetrahydronaphthalen-2-yl)-propyloxy]-benzoic acid.

12. The compound of claim 1, wherein the compound is (RS)-4-[4-(pyridin-2-yl)-2-(5,5,8,8-tetramethyl-5,6,7,8-tetrahydronaphthalen-2-yl)-butyloxy]-benzoic acid.

13. The compound of claim 1, wherein the compound is (RS)-4-[4-(pyridin-3-yl)-2-(5,5,8,8-tetramethyl-5,6,7,8-tetrahydronaphthalen-2-yl)-butyloxy]-benzoic acid.

14. The compound of claim 1, wherein the compound is (RS)-4-[4-(pyridin-4-yl)-2-(5,5,8,8-tetramethyl-5,6,7,8-tetrahydronaphthalen-2-yl)-butyloxy]-benzoic acid.

15. The compound of claim 1, wherein the compound is (RS)-4-[3-(1-(pyrazol-4-yl)-2-(5,5,8,8-tetramethyl-5,6,7,8-tetrahydronaphthalen-2-yl)-propyloxy]-benzoic acid.

16. The compound of claim 1, wherein the compound is (RS)-4-[4-(pyrazol-1-yl)-2-(5,5,8,8-tetramethyl-5,6,7,8-tetrahydronaphthalen-2-yl)-butyloxy]-benzoic acid.

17. The compound of claim 1, wherein the compound is (RS)-4-[4-(pyrrol-1-yl)-2-(5,5,8,8-tetramethyl-5,6,7,8-tetrahydronaphthalen-2-yl)-butyloxy]-benzoic acid.

18. The compound of claim 1, wherein the compound is (RS)-4-[3-(5-methyl-isoxazol-2-yl)-2-(5,5,8,8-tetramethyl-5,6,7,8-tetrahydronaphthalen-2-yl)-propyloxy]-benzoic acid.

19. The compound of claim 1, wherein the compound is (RS)-4-[3-(2-methyl-thiazol-4-yl)-2-(5,5,8,8-tetramethyl-5,6,7,8-tetrahydronaphthalen-3-yl)-propyloxy]-benzoic acid.

20. The compound of claim 1, wherein the compound is (RS)-4-[3-(1,2,4-oxadiazol-3-yl)-2-(5,5,8,8-tetramethyl-5,6,7,8-tetrahydronaphthalen-2-yl)-propyloxy]-benzoic acid.

21. The compound of claim 1, wherein the compound is (RS)-4-[3-(furan-2-yl)-2-(5,5,8,8-tetramethyl-5,6,7,8-tetrahydronaphthalen-2-yl)-propyloxy]-benzoic acid.

22. The compound of claim 1, wherein the compound is (RS)-4-[3-(tetrahydrofuran-2-yl)-2-(5,5,8,8-tetramethyl-5,6,7,8-tetrahydronaphthalen-2-yl)-propyloxy]-benzoic acid.

23. The compound of claim 1, wherein the compound is (RS)-4-[3-(cyclohexyl)-2-(5,5,8,8-tetramethyl-5,6,7,8-tetrahydronaphthalen-2-yl)-propyloxy]-benzoic acid.

24. The compound of claim 1, wherein the compound is (RS)-4-[6-hydroxy-2-(5,5,8,8-tetramethyl-5,6,7,8-tetrahydronaphthalen-2-yl)-hexyloxy]-benzoic acid.

25. The compound of claim 1, wherein the compound is (RS)-4-[4-thioethyl-2-(5,5,8,8-tetramethyl-5,6,7,8-tetrahydronaphthalen-2-yl)-butyloxy]-benzoic acid.

* * * * *

UNITED STATES PATENT AND TRADEMARK OFFICE
CERTIFICATE OF CORRECTION

PATENT NO.    : 6,603,012 B2
DATED         : August 5, 2003
INVENTOR(S)   : Paula Nanette Belloni et al.

It is certified that error appears in the above-identified patent and that said Letters Patent is hereby corrected as shown below:

<u>Column 63,</u>
Lines 17-19, delete "19.   The compound of claim 1, wherein the compound is (RS)-4-[3-(2-methyl-thiazol-4-yl)-2-(5,5,8,8-tetramethyl-5,6,7,8-tetrahydronaphthalen-3-yl)-propyloxy)-benzoic acid." and insert -- 19.   The compound of claim 1, wherein the compound is (RS)-4-[3-(2-methyl-thiazol-4-yl)-2-(5,5,8,8-tetramethyl-5,6,7,8-tetrahydronaphthalen-2-yl)-propyloxy]-benzoic acid. --

Signed and Sealed this

Twenty-seventh Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,603,012 B2  
DATED : August 5, 2003  
INVENTOR(S) : Paula Nanette Belloni et al.

It is certified that error appears in the above-identified patent and that said Letters Patent is hereby corrected as shown below:

Column 2,  
Lines 55-64, replace

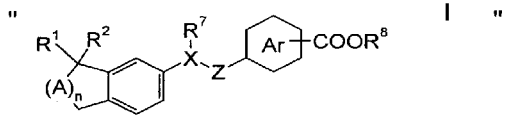

with

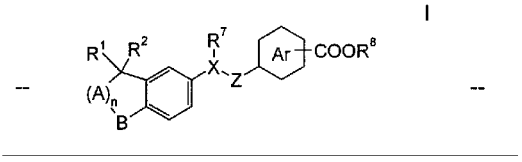

Column 3,  
Lines 36-44, replace

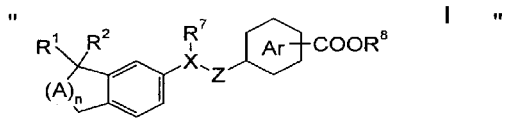

with

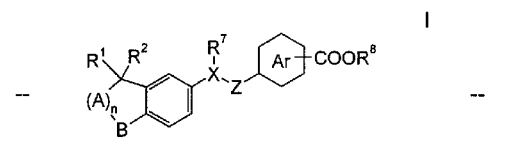

UNITED STATES PATENT AND TRADEMARK OFFICE
CERTIFICATE OF CORRECTION

PATENT NO. : 6,603,012 B2
DATED : August 5, 2003
INVENTOR(S) : Paula Nanette Belloni et al.

It is certified that error appears in the above-identified patent and that said Letters Patent is hereby corrected as shown below:

Column 62,
Line 5-12, replace

" 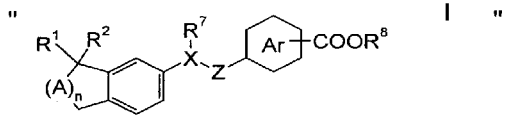 | "

with

-- 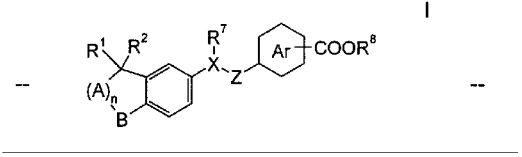 --

Signed and Sealed this

Twenty-seventh Day of July, 2004

JON W. DUDAS
*Acting Director of the United States Patent and Trademark Office*